(12) United States Patent
Bolea

(10) Patent No.: US 11,383,083 B2
(45) Date of Patent: Jul. 12, 2022

(54) SYSTEMS AND METHODS OF DETECTING AND TREATING OBSTRUCTIVE SLEEP APNEA

(71) Applicant: LivaNova USA, Inc., Houston, TX (US)

(72) Inventor: Stephen L. Bolea, Watertown, MN (US)

(73) Assignee: LivaNova USA, Inc., Houston, TX (US)

( * ) Notice: Subject to any disclaimer, the term of this patent is extended or adjusted under 35 U.S.C. 154(b) by 437 days.

(21) Appl. No.: 14/620,131

(22) Filed: Feb. 11, 2015

(65) Prior Publication Data

US 2015/0224307 A1 Aug. 13, 2015

Related U.S. Application Data

(60) Provisional application No. 61/938,615, filed on Feb. 11, 2014, provisional application No. 61/940,314, (Continued)

(51) Int. Cl.
| | |
|---|---|
| *A61N 1/00* | (2006.01) |
| *A61N 1/36* | (2006.01) |

(Continued)

(52) U.S. Cl.
CPC .......... *A61N 1/3601* (2013.01); *A61B 5/0036* (2018.08); *A61B 5/4818* (2013.01);
(Continued)

(58) Field of Classification Search
None
See application file for complete search history.

(56) References Cited

U.S. PATENT DOCUMENTS

| 758,030 A | 4/1904 | Carence |
|---|---|---|
| 1,520,930 A | 12/1924 | Calhoun |

(Continued)

FOREIGN PATENT DOCUMENTS

| EP | 0 892 926 B1 | 6/2002 |
|---|---|---|
| EP | 0 900 102 B1 | 7/2004 |

(Continued)

OTHER PUBLICATIONS

Spence et al., "High-flow nasal cannula as a device to provide continuous positive airway pressure in infants," *Journal of Perinatology*, Dec. 2007, pp. 772-775, vol. 27 (12), Nature Publishing Group.
(Continued)

*Primary Examiner* — Jennifer Pitrak McDonald
*Assistant Examiner* — Elizabeth K So
(74) *Attorney, Agent, or Firm* — Foley & Lardner LLP

(57) ABSTRACT

A method of providing a sleep apnea nerve stimulation therapy to a subject may include detecting a respiratory waveform of the subject with a sensor. The sensor may be configured for coupling to the subject. The respiratory waveform may include a plurality of respiratory cycles each corresponding to at least one of a breath and an attempted breath of the subject. The method may also include identifying a breathing pattern within the respiratory waveform over a period of time. The breathing pattern may include a repeating pattern of a plurality of respiratory cycles followed by at least one respiratory cycle corresponding to a disordered breathing event. The method may also include generating a series of stimulation pulses with an implantable nerve stimulator configured for coupling to a hypoglossal nerve of the subject. The series of stimulation pulses may be coordinated with the breathing pattern.

8 Claims, 30 Drawing Sheets

Related U.S. Application Data filed on Feb. 14, 2014, provisional application No. 61/940,764, filed on Feb. 17, 2014, provisional application No. 61/942,616, filed on Feb. 20, 2014.

(51) Int. Cl.
*A61N 1/05* (2006.01)
*A61B 5/00* (2006.01)

(52) U.S. Cl.
CPC .......... *A61B 5/4836* (2013.01); *A61N 1/0556* (2013.01); *A61N 1/3611* (2013.01); *A61N 1/36057* (2013.01); *A61N 1/36139* (2013.01); *A61N 1/36167* (2013.01); *A61N 1/36192* (2013.01); *A61N 1/36196* (2013.01)

(56) References Cited

U.S. PATENT DOCUMENTS

| | | |
|---|---|---|
| 1,701,277 A | 2/1929 | Shindel |
| 1,914,418 A | 6/1933 | Goyena |
| 2,046,664 A | 7/1936 | Weaver |
| 2,151,227 A | 3/1939 | Pawelek |
| 2,237,954 A | 4/1941 | Wilson |
| 2,243,360 A | 5/1941 | Slatis |
| 2,274,886 A | 3/1942 | Carroll |
| 2,526,586 A | 10/1950 | Shuff |
| 2,693,799 A | 11/1954 | Herman |
| 2,777,442 A | 1/1957 | Zelano |
| 2,928,388 A | 3/1960 | Jaroslaw |
| 3,457,917 A | 7/1969 | Mercurio |
| 3,513,839 A | 5/1970 | Vacante |
| 3,680,555 A | 8/1972 | Warncke |
| 3,722,509 A | 3/1973 | Nebel |
| 3,774,618 A | 11/1973 | Avery |
| 3,865,106 A | 2/1975 | Palush |
| 3,884,223 A | 5/1975 | Keindl |
| 3,893,463 A | 7/1975 | Williams |
| 3,906,936 A | 9/1975 | Habal |
| 4,220,150 A | 9/1980 | King |
| 4,221,217 A | 9/1980 | Amezcua |
| 4,267,831 A | 5/1981 | Aguilar |
| 4,374,527 A | 2/1983 | Iversen |
| 4,414,986 A | 11/1983 | Dickhudt et al. |
| 4,506,666 A | 3/1985 | Durkan |
| 4,567,892 A | 2/1986 | Plicchi et al. |
| 4,573,481 A | 3/1986 | Bullara |
| 4,602,624 A | 7/1986 | Kauer |
| 4,612,934 A | 9/1986 | Borkan |
| 4,777,963 A | 10/1988 | McKenna |
| 4,830,008 A | 5/1989 | Meer |
| 4,899,750 A | 2/1990 | Eckwall |
| 4,915,105 A | 4/1990 | Lee |
| 4,919,136 A | 4/1990 | Alt |
| 4,934,368 A | 6/1990 | Lynch |
| 4,940,065 A | 7/1990 | Tanagho et al. |
| 4,960,133 A | 10/1990 | Hewson |
| 4,979,511 A | 12/1990 | Reese |
| 4,996,983 A | 3/1991 | AmRhein |
| 5,016,808 A | 5/1991 | Heil, Jr. et al. |
| 5,036,862 A | 8/1991 | Pohndorf |
| 5,095,905 A | 3/1992 | Klepinski |
| 5,105,826 A | 4/1992 | Smits et al. |
| 5,121,754 A | 6/1992 | Mullett |
| 5,133,354 A | 7/1992 | Kallock |
| 5,146,918 A | 9/1992 | Kallok et al. |
| 5,158,080 A | 10/1992 | Kallock |
| 5,174,287 A | 12/1992 | Kallok et al. |
| 5,178,156 A | 1/1993 | Takishima et al. |
| 5,190,053 A | 3/1993 | Meer |
| 5,211,173 A | 5/1993 | Kallok et al. |
| 5,215,082 A | 6/1993 | Kallok et al. |
| 5,277,193 A | 1/1994 | Takishima et al. |
| 5,281,219 A | 1/1994 | Kallok et al. |
| 5,282,468 A | 2/1994 | Klepinksi |
| 5,300,094 A | 4/1994 | Kallok et al. |
| 5,324,321 A | 6/1994 | Pohndorf et al. |
| 5,335,657 A | 8/1994 | Terry, Jr. et al. |
| 5,344,438 A | 9/1994 | Testerman et al. |
| 5,388,578 A | 2/1995 | Yomtov et al. |
| 5,392,773 A | 2/1995 | Bertrand |
| 5,417,205 A | 5/1995 | Wang |
| 5,425,359 A | 6/1995 | Liou |
| 5,458,629 A | 10/1995 | Baudino et al. |
| 5,483,969 A | 1/1996 | Testerman et al. |
| 5,485,836 A | 1/1996 | Lincoln |
| 5,485,851 A | 1/1996 | Erickson |
| 5,487,756 A | 1/1996 | Kallesoe et al. |
| 5,511,543 A | 4/1996 | Shirley |
| 5,522,382 A | 6/1996 | Sullivan et al. |
| 5,522,862 A | 6/1996 | Testerman et al. |
| 5,531,778 A | 7/1996 | Maschino et al. |
| 5,540,731 A | 7/1996 | Testerman |
| 5,540,732 A | 7/1996 | Testerman |
| 5,540,733 A | 7/1996 | Testerman et al. |
| 5,540,734 A | 7/1996 | Zabara |
| 5,546,938 A | 8/1996 | McKenzie |
| 5,549,655 A | 8/1996 | Erickson |
| 5,568,808 A | 10/1996 | Rimkus |
| 5,591,216 A | 1/1997 | Testerman et al. |
| 5,630,411 A | 5/1997 | Holscher |
| 5,682,881 A | 11/1997 | Winthrop et al. |
| 5,697,105 A | 12/1997 | White |
| 5,697,363 A | 12/1997 | Hart |
| 5,730,122 A | 3/1998 | Lurie |
| 5,740,798 A | 4/1998 | McKinney |
| 5,752,511 A | 5/1998 | Simmons et al. |
| 5,787,884 A | 8/1998 | Tovey |
| 5,848,589 A | 12/1998 | Welnetz |
| 5,855,552 A | 1/1999 | Houser et al. |
| 5,890,491 A | 4/1999 | Rimkus |
| 5,895,360 A | 4/1999 | Christopherson et al. |
| 5,919,220 A | 7/1999 | Stieglitz et al. |
| 5,922,014 A | 7/1999 | Warman et al. |
| 5,938,596 A | 8/1999 | Woloszko et al. |
| 5,944,680 A | 8/1999 | Christopherson et al. |
| 5,947,119 A | 9/1999 | Reznick |
| 6,010,459 A | 1/2000 | Silkoff et al. |
| 6,015,389 A | 1/2000 | Brown |
| 6,021,352 A | 2/2000 | Christopherson et al. |
| 6,021,354 A | 2/2000 | Warman et al. |
| 6,029,667 A | 2/2000 | Lurie |
| 6,041,780 A | 3/2000 | Richard |
| 6,066,165 A | 5/2000 | Racz |
| 6,098,624 A | 8/2000 | Utamaru |
| 6,109,262 A | 8/2000 | Tovey |
| 6,119,690 A | 9/2000 | Pentaleo |
| 6,126,611 A | 10/2000 | Bourgeois et al. |
| 6,132,384 A | 10/2000 | Christopherson et al. |
| 6,198,970 B1 | 3/2001 | Freed et al. |
| 6,201,994 B1 | 3/2001 | Warman et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,240,316 B1 | 5/2001 | Richmond et al. |
| 6,244,267 B1 | 6/2001 | Eifrig |
| 6,251,126 B1 | 6/2001 | Ottenhoff et al. |
| 6,269,269 B1 | 7/2001 | Ottenhoff et al. |
| 6,292,703 B1 | 9/2001 | Meier et al. |
| 6,345,202 B2 | 2/2002 | Richmond et al. |
| 6,366,815 B1 | 4/2002 | Haugland et al. |
| 6,460,539 B1 | 10/2002 | Japuntich et al. |
| 6,484,725 B1 | 11/2002 | Chi |
| 6,511,458 B2 | 1/2003 | Milo et al. |
| 6,514,217 B1 | 2/2003 | Selmon et al. |
| 6,542,776 B1 | 4/2003 | Gordon et al. |
| 6,561,188 B1 | 5/2003 | Ellis |
| 6,587,725 B1 | 7/2003 | Durand et al. |
| 6,600,956 B2 | 7/2003 | Maschino et al. |
| 6,606,521 B2 | 8/2003 | Paspa et al. |
| 6,609,031 B1 | 8/2003 | Law et al. |
| 6,626,179 B1 | 9/2003 | Pedley |
| 6,636,767 B1 | 10/2003 | Knudson et al. |
| 6,641,542 B2 | 11/2003 | Cho et al. |

(56) References Cited

U.S. PATENT DOCUMENTS

| | | |
|---|---|---|
| 6,647,289 B2 | 11/2003 | Prutchi |
| 6,651,652 B1 | 11/2003 | Ward |
| 6,718,982 B2 | 4/2004 | Smith et al. |
| 6,719,725 B2 | 4/2004 | Milo et al. |
| 6,721,603 B2 | 4/2004 | Zabara et al. |
| 6,772,015 B2 | 8/2004 | Dahl et al. |
| 6,776,162 B2 | 8/2004 | Wood |
| 6,799,575 B1 | 10/2004 | Carter |
| 6,819,958 B2 | 11/2004 | Weiner et al. |
| 6,829,503 B2 | 12/2004 | Alt |
| 6,829,508 B2 | 12/2004 | Schulman et al. |
| RE38,705 E | 2/2005 | Hill et al. |
| 6,876,885 B2 | 4/2005 | Swoyer et al. |
| 6,881,192 B1 | 4/2005 | Park |
| 6,883,518 B2 | 4/2005 | Mittelstadt et al. |
| 6,890,306 B2 | 5/2005 | Poezevera |
| 6,904,320 B2 | 6/2005 | Park et al. |
| 6,907,295 B2 | 6/2005 | Gross et al. |
| 6,928,324 B2 | 8/2005 | Park et al. |
| 6,978,171 B2 | 12/2005 | Goetz et al. |
| 6,997,177 B2 | 2/2006 | Wood |
| 7,027,869 B2 | 4/2006 | Danek et al. |
| 7,054,692 B1 | 5/2006 | Whitehurst et al. |
| 7,065,410 B2 | 6/2006 | Bardy et al. |
| 7,082,331 B1 | 7/2006 | Park et al. |
| 7,087,053 B2 | 8/2006 | Vanney |
| 7,089,932 B2 | 8/2006 | Dodds |
| 7,094,206 B2 | 8/2006 | Hoffman |
| 7,117,036 B2 | 10/2006 | Florio |
| 7,128,717 B1 | 10/2006 | Thatch et al. |
| 7,142,919 B2 | 11/2006 | Hine et al. |
| 7,149,573 B2 | 12/2006 | Wang |
| 7,152,604 B2 | 12/2006 | Hickle et al. |
| 7,155,278 B2 | 12/2006 | King et al. |
| 7,156,098 B2 | 1/2007 | Dolezal et al. |
| 7,160,252 B2 | 1/2007 | Cho |
| 7,160,255 B2 | 1/2007 | Saadat |
| 7,178,524 B2 | 2/2007 | Noble |
| 7,200,440 B2 | 4/2007 | Kim et al. |
| 7,225,034 B2 | 5/2007 | Ries et al. |
| 7,239,918 B2 | 7/2007 | Strother et al. |
| 7,242,987 B2 | 7/2007 | Holleman et al. |
| 7,263,996 B2 | 9/2007 | Seoul |
| 7,277,749 B2 | 10/2007 | Gordon et al. |
| 7,283,867 B2 | 10/2007 | Strother et al. |
| 7,302,951 B2 | 12/2007 | Mittelstadt et al. |
| 7,313,442 B2 | 12/2007 | Velasco et al. |
| 7,343,202 B2 | 3/2008 | Mrva et al. |
| 7,346,398 B2 | 3/2008 | Gross et al. |
| 7,366,572 B2 | 4/2008 | Heruth et al. |
| 7,396,333 B2 | 7/2008 | Stahmann et al. |
| 7,438,686 B2 | 10/2008 | Cho et al. |
| 7,463,928 B2 | 12/2008 | Lee et al. |
| 7,473,227 B2 | 1/2009 | Hsu et al. |
| 7,515,968 B2 | 4/2009 | Metzler et al. |
| 7,524,292 B2 | 4/2009 | Cho et al. |
| 7,561,922 B2 | 7/2009 | Cohen et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,627,375 B2 | 12/2009 | Bardy et al. |
| 7,630,771 B2 | 12/2009 | Cauller |
| 7,634,315 B2 | 12/2009 | Cholette |
| 7,636,602 B2 | 12/2009 | Baru Fassio et al. |
| 7,657,311 B2 | 2/2010 | Bardy et al. |
| 7,660,632 B2 | 2/2010 | Kirby et al. |
| 7,662,105 B2 | 2/2010 | Hatlestad |
| 7,672,728 B2 | 3/2010 | Libbus et al. |
| 7,672,729 B2 | 3/2010 | Koh et al. |
| 7,680,537 B2 | 3/2010 | Stahmann et al. |
| 7,680,538 B2 | 3/2010 | Durand et al. |
| 7,684,869 B2 | 3/2010 | Bradley et al. |
| 7,697,968 B2 | 4/2010 | Moore |
| 7,697,984 B2 | 4/2010 | Hill et al. |
| 7,697,990 B2 | 4/2010 | Ujhazy et al. |
| 7,717,848 B2 | 5/2010 | Heruth et al. |
| 7,720,534 B2 | 5/2010 | Bardy et al. |
| 7,725,195 B2 | 5/2010 | Lima et al. |
| 7,725,198 B2 | 5/2010 | Cross, Jr. et al. |
| 7,734,340 B2 | 6/2010 | De Ridder |
| 7,734,348 B2 | 6/2010 | Zhang et al. |
| 7,738,952 B2 | 6/2010 | Yun et al. |
| 7,747,323 B2 | 6/2010 | Libbus et al. |
| 7,751,880 B1 | 7/2010 | Cholette |
| 7,751,885 B2 | 7/2010 | Bardy et al. |
| 7,758,384 B2 | 7/2010 | Alexander et al. |
| 7,765,000 B2 | 7/2010 | Zhang et al. |
| 7,769,461 B2 | 8/2010 | Whitehurst et al. |
| 7,783,353 B2 | 8/2010 | Libbus et al. |
| 7,785,262 B2 | 8/2010 | Melker et al. |
| 7,787,959 B1 | 8/2010 | Morgan |
| 7,792,590 B1 | 9/2010 | Pianca et al. |
| 7,797,050 B2 | 9/2010 | Libbus et al. |
| 7,797,057 B2 | 9/2010 | Harris |
| 7,797,058 B2 | 9/2010 | Mrva et al. |
| 7,805,195 B2 | 9/2010 | Zealear |
| 7,809,442 B2 | 10/2010 | Bolea et al. |
| 7,813,797 B2 | 10/2010 | Bardy et al. |
| 7,813,802 B2 | 10/2010 | Tcheng et al. |
| 7,813,809 B2 | 10/2010 | Strother et al. |
| 7,818,063 B2 | 10/2010 | Wallace et al. |
| 7,822,486 B2 | 10/2010 | Foster et al. |
| 7,860,570 B2 | 12/2010 | Whitehurst et al. |
| 7,979,128 B2 | 7/2011 | Tehrani et al. |
| 8,249,723 B2 | 8/2012 | McCreery |
| 8,311,645 B2 | 11/2012 | Bolea et al. |
| 8,386,046 B2 | 2/2013 | Tesfayesus et al. |
| 8,428,727 B2 | 4/2013 | Bolea et al. |
| 8,498,712 B2 | 7/2013 | Bolea et al. |
| 8,545,416 B1 | 10/2013 | Kayyali et al. |
| 8,626,304 B2 | 1/2014 | Bolea et al. |
| 8,639,354 B2 | 1/2014 | Bolea et al. |
| 8,718,783 B2 | 5/2014 | Bolea et al. |
| 8,744,584 B2 | 6/2014 | Bolea et al. |
| 8,855,771 B2 | 10/2014 | Tesfayesus et al. |
| 9,913,982 B2 * | 3/2018 | Bolea .................. A61N 1/0556 |
| 2001/0010010 A1 | 7/2001 | Richmond et al. |
| 2001/0031929 A1 | 10/2001 | O'Toole |
| 2002/0010495 A1 | 1/2002 | Freed et al. |
| 2002/0049479 A1 | 4/2002 | Pitts |
| 2002/0092527 A1 | 7/2002 | Wood |
| 2002/0128700 A1 | 9/2002 | Cross |
| 2002/0156507 A1 | 10/2002 | Lindenthaler |
| 2002/0165462 A1 | 11/2002 | Westbrook et al. |
| 2002/0166556 A1 | 11/2002 | Jacob |
| 2002/0195108 A1 | 12/2002 | Mittelstadt et al. |
| 2002/0195109 A1 | 12/2002 | Mittelstadt et al. |
| 2003/0034031 A1 | 2/2003 | Lev et al. |
| 2003/0078643 A1 | 4/2003 | Schulman et al. |
| 2003/0083696 A1 | 5/2003 | Avital |
| 2003/0093128 A1 | 5/2003 | Freed et al. |
| 2003/0106555 A1 | 6/2003 | Tovey |
| 2003/0106556 A1 | 6/2003 | Alperovich et al. |
| 2003/0114895 A1 | 6/2003 | Gordon et al. |
| 2003/0114905 A1 | 6/2003 | Kuzma |
| 2003/0153953 A1 | 8/2003 | Park et al. |
| 2003/0167018 A1 | 9/2003 | Wyckoff |
| 2003/0195571 A1 | 10/2003 | Burnes et al. |
| 2003/0209145 A1 | 11/2003 | Soper |
| 2003/0216789 A1 | 11/2003 | Deem et al. |
| 2004/0015204 A1 | 1/2004 | Whitehurst et al. |
| 2004/0020489 A1 | 2/2004 | Gillispie et al. |
| 2004/0049241 A1 | 3/2004 | Campos |
| 2004/0055603 A1 | 3/2004 | Bruce |
| 2004/0073272 A1 | 4/2004 | Knudson et al. |
| 2004/0089303 A1 | 5/2004 | Chien |
| 2004/0111139 A1 | 6/2004 | McCreery |
| 2004/0116819 A1 | 6/2004 | Alt |
| 2004/0138581 A1 | 7/2004 | Frei et al. |
| 2004/0153127 A1 | 8/2004 | Gordon et al. |
| 2004/0162499 A1 | 8/2004 | Nagai et al. |
| 2004/0194784 A1 | 10/2004 | Bertrand |
| 2004/0215288 A1 | 10/2004 | Lee et al. |
| 2004/0215290 A1 | 10/2004 | Zealer |

(56) References Cited

U.S. PATENT DOCUMENTS

| | | |
|---|---|---|
| 2004/0230278 A1 | 11/2004 | Dahl et al. |
| 2004/0233058 A1 | 11/2004 | Dodds |
| 2004/0260310 A1 | 12/2004 | Harris |
| 2004/0261791 A1 | 12/2004 | Horian |
| 2005/0004610 A1 | 1/2005 | Kim et al. |
| 2005/0010265 A1 | 1/2005 | Fassio et al. |
| 2005/0038490 A1 | 2/2005 | Gross et al. |
| 2005/0039757 A1 | 2/2005 | Wood |
| 2005/0043644 A1 | 2/2005 | Stahmann et al. |
| 2005/0043772 A1 | 2/2005 | Stahmann et al. |
| 2005/0076908 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0098176 A1 | 5/2005 | Hoffrichter |
| 2005/0101833 A1 | 5/2005 | Hsu et al. |
| 2005/0119711 A1 | 6/2005 | Cho et al. |
| 2005/0139216 A1 | 6/2005 | Mittelstadt et al. |
| 2005/0165457 A1 | 7/2005 | Benser et al. |
| 2005/0209513 A1 | 9/2005 | Heruth et al. |
| 2005/0209643 A1 | 9/2005 | Heruth et al. |
| 2005/0234523 A1 | 10/2005 | Levin et al. |
| 2005/0235992 A1 | 10/2005 | Djupesland |
| 2005/0240241 A1 | 10/2005 | Yun et al. |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004429 A1 | 1/2006 | Mrva et al. |
| 2006/0005842 A1 | 1/2006 | Rashad et al. |
| 2006/0025828 A1 | 2/2006 | Armstrong et al. |
| 2006/0030919 A1 | 2/2006 | Mrva et al. |
| 2006/0032497 A1 | 2/2006 | Doshi |
| 2006/0041295 A1 | 2/2006 | Osypka |
| 2006/0052836 A1 | 3/2006 | Kim et al. |
| 2006/0058588 A1 | 3/2006 | Zdeblick |
| 2006/0058852 A1 | 3/2006 | Koh et al. |
| 2006/0064029 A1 | 3/2006 | Arad |
| 2006/0064138 A1 | 3/2006 | Velasco et al. |
| 2006/0079802 A1 | 4/2006 | Jensen et al. |
| 2006/0095088 A1 | 5/2006 | De Ridder |
| 2006/0111755 A1 | 5/2006 | Stone et al. |
| 2006/0116739 A1 | 6/2006 | Betser et al. |
| 2006/0129189 A1 | 6/2006 | George et al. |
| 2006/0135886 A1 | 6/2006 | Lippert et al. |
| 2006/0136024 A1 | 6/2006 | Cohen et al. |
| 2006/0142815 A1 | 6/2006 | Tehrani et al. |
| 2006/0144398 A1 | 7/2006 | Doshi et al. |
| 2006/0149345 A1 | 7/2006 | Boggs et al. |
| 2006/0150978 A1 | 7/2006 | Doshi et al. |
| 2006/0150979 A1 | 7/2006 | Doshi et al. |
| 2006/0150980 A1 | 7/2006 | Kim |
| 2006/0167497 A1 | 7/2006 | Armstrong et al. |
| 2006/0184204 A1 | 8/2006 | He |
| 2006/0195170 A1 | 8/2006 | Cohen et al. |
| 2006/0211951 A1 | 9/2006 | Milajasevic et al. |
| 2006/0224209 A1 | 10/2006 | Meyer |
| 2006/0224211 A1 | 10/2006 | Durand |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271118 A1 | 11/2006 | Libbus et al. |
| 2006/0271137 A1 | 11/2006 | Stanton-Hicks |
| 2006/0282127 A1 | 12/2006 | Zealear |
| 2006/0293720 A1 | 12/2006 | DiLorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0043411 A1 | 2/2007 | Foster et al. |
| 2007/0095347 A1 | 5/2007 | Lampotang et al. |
| 2007/0125379 A1 | 6/2007 | Pierro et al. |
| 2007/0150006 A1 | 6/2007 | Libbus |
| 2007/0175478 A1 | 8/2007 | Brunst |
| 2007/0227542 A1 | 10/2007 | Kashmakov et al. |
| 2007/0239243 A1 | 10/2007 | Moffitt et al. |
| 2007/0277832 A1 | 12/2007 | Doshi et al. |
| 2007/0282410 A1 | 12/2007 | Cross et al. |
| 2007/0283962 A1 | 12/2007 | Doshi et al. |
| 2007/0295338 A1 | 12/2007 | Loomas et al. |
| 2008/0023007 A1 | 1/2008 | Dolezal et al. |
| 2008/0027480 A1 | 1/2008 | van der Burg et al. |
| 2008/0027502 A1 | 1/2008 | Ransom |
| 2008/0041373 A1 | 2/2008 | Doshi et al. |
| 2008/0099029 A1 | 5/2008 | Lamberg |
| 2008/0103407 A1 | 5/2008 | Bolea et al. |
| 2008/0103545 A1 | 5/2008 | Bolea et al. |
| 2008/0147142 A1 | 6/2008 | Testerman et al. |
| 2008/0163875 A1 | 7/2008 | Aarestad et al. |
| 2008/0183254 A1 | 7/2008 | Bly et al. |
| 2009/0044814 A1 | 2/2009 | Iancea et al. |
| 2009/0270707 A1 | 10/2009 | Alfoqaha et al. |
| 2009/0276024 A1 | 11/2009 | Bonde et al. |
| 2009/0308395 A1 | 12/2009 | Lee et al. |
| 2009/0318986 A1 | 12/2009 | Alo et al. |
| 2009/0326408 A1 | 12/2009 | Moon et al. |
| 2010/0016749 A1 | 1/2010 | Atsma et al. |
| 2010/0036285 A1 | 2/2010 | Govari et al. |
| 2010/0047376 A1 | 2/2010 | Imbeau et al. |
| 2010/0076536 A1 | 3/2010 | Merz et al. |
| 2010/0094379 A1 | 4/2010 | Meadows et al. |
| 2010/0100150 A1 | 4/2010 | Kirby et al. |
| 2010/0125310 A1 | 5/2010 | Wilson et al. |
| 2010/0131029 A1 | 5/2010 | Durand et al. |
| 2010/0137931 A1 | 6/2010 | Hopper et al. |
| 2010/0137949 A1 | 6/2010 | Mazgalev et al. |
| 2010/0137956 A1 | 6/2010 | Osypka et al. |
| 2010/0152553 A1 | 6/2010 | Ujhazy et al. |
| 2010/0174341 A1 | 7/2010 | Bolea et al. |
| 2010/0228133 A1 | 9/2010 | Averina et al. |
| 2010/0228317 A1 | 9/2010 | Libbus et al. |
| 2010/0241207 A1 | 9/2010 | Bluger |
| 2010/0257729 A1 | 10/2010 | Alexander et al. |
| 2010/0262209 A1 | 10/2010 | King et al. |
| 2011/0071591 A1 | 3/2011 | Bolea et al. |
| 2012/0017920 A1 | 1/2012 | Sanders |
| 2012/0022389 A1 | 1/2012 | Sanders |
| 2012/0192874 A1 | 8/2012 | Bolea et al. |
| 2013/0085546 A1 | 4/2013 | Bolea et al. |
| 2013/0197376 A1 | 8/2013 | Alt et al. |
| 2014/0228905 A1 | 8/2014 | Bolea |
| 2014/0243629 A1* | 8/2014 | Syroid ............... A61B 5/14552 600/324 |
| 2015/0038867 A1* | 2/2015 | Armitstead ............ A61B 5/091 600/538 |
| 2015/0223699 A1* | 8/2015 | Yoon ................... A61B 5/0816 600/484 |

FOREIGN PATENT DOCUMENTS

| | | |
|---|---|---|
| EP | 1 404 221 B1 | 2/2007 |
| EP | 1 854 494 A1 | 11/2007 |
| EP | 1 322 384 B1 | 12/2007 |
| JP | 53118893 | 10/1978 |
| JP | 9-294819 | 11/1997 |
| JP | 2000-506601 | 5/2000 |
| JP | 2000-508562 | 7/2000 |
| JP | 2003-305135 | 10/2003 |
| JP | 2004-508908 | 3/2004 |
| JP | 2004-532707 | 10/2004 |
| JP | 3688301 | 6/2005 |
| JP | 2005-521485 | 7/2005 |
| JP | 2007-21156 | 2/2007 |
| WO | WO 98/20938 | 5/1998 |
| WO | WO 02/024279 | 3/2002 |
| WO | WO 03/000133 | 1/2003 |

(56) References Cited

FOREIGN PATENT DOCUMENTS

| WO | WO 03/000347 A1 | 1/2003 |
|---|---|---|
| WO | WO 03/082393 A1 | 10/2003 |
| WO | WO 2005/004993 A1 | 1/2005 |
| WO | WO 2006/045251 A1 | 5/2006 |
| WO | WO 2006/063339 A2 | 6/2006 |
| WO | WO 2007/134458 A1 | 11/2007 |
| WO | WO 2008/046190 | 4/2008 |
| WO | WO 2010/039853 A1 | 4/2010 |
| WO | WO 2012/103196 A2 | 8/2012 |

OTHER PUBLICATIONS

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

De Almeida et al., "Nasal pressure recordings to detect obstructive sleep apnea," *Sleep and Breathing*, Feb. 25, 2006, pp. 62-69, vol. 10 (2), Springer Heidelberg.

Saslow et al., "Work of breathing using high-flow nasal cannula in preterm infants," *Journal of Perinatology*, May 11, 2006, pp. 476-480, vol. 26 (8), Nature Publishing Group.

Campbell et al., "Nasal Continuous positive airway pressure from high flow cannula versus Infant Flow for preterm infants," *Journal of Perinatology*, Jul. 2006, pp. 546-549, vol. 26 (9), Nature Publishing Group.

Trevisanuto et al., "A new device for administration of continuous positive airway pressure in preterm infants: comparison with a standard nasal CPAP continuous positive airway pressure system," *Intensive Care Medicine*, Apr. 2005, pp. 859-864, vol. 31 (6), Springer-Verlag.

Verse et al., "New developments in the therapy of obstructive sleep apnea," *European Archives of Oto-Rhino-Laryngology*, Jan. 2001, pp. 31-37, vol. 258 (1), Springer-Verlag.

Paquereau et al., "Positive pressure titration in the treatment of obstructive sleep apnea syndrome using continuous airway positive pressure," *Revue Des Maladies Respiratoires*, Apr. 2000, pp. 459-465, vol. 17 (2), Masson Editeur.

Mahadevia et al., "Effects of expiratory positive airway pressure on sleep-induced respiratory abnormalities in patients with hypersomnia-sleep apnea syndrome," *Am. Rev. Respir. Dis.*, Feb. 1983, vol. 128, pp. 708-711.

Tiran et al., "An Improved Device for Posterior Rhinomanometry to Measure Nasal Resistance," *Journal of Biomechnical Engineering*, Nov. 2005, vol. 127, pp. 994-997.

Noseda et al., "Compliance with nasal continuous positive airway pressure assessed with a pressure monitor: pattern of use and influence of sleep habits," Chest Clinics and Sleep Laboratories, Hôpitaux Erasme et Brugmann, Université Libre de Bruxelles, Brussels, Belgium, 2000, vol. 94, pp. 76-81.

Goding Jr. et al., "Relief of Upper Airway Obstruction With Hypoglossal Nerve Stimulation in the Canine," *The Laryngoscope*, Feb. 1998, pp. 162-169, vol. 108, Lippincott-Raven Publishers, U.S.A.

Sahin et al., "Chronic recordings of hypoglossal nerve activity in a dog model of upper airway obstruction," *Journal of Applied Physiology* 87(6), 1999, The American Physiological Society, pp. 2197-2206.

Ferguson et al., "Effect of Mandibular and Tongue Protrusion on Upper Airway Size During Wakefulness." *American Journal of Respiratory and Critical Care Medicine*, 1997, pp. 1748-1754, vol. 1553.

Isono et al., "Interaction of cross-sectional area, driving pressure, and airflow of passive velopharvnx." *American Physiological Society*, 1997, pp. 851-859, vol. 83.

Oliven et al., "Effect of genioglossus contraction on pharyngeal lumen and airflow in sleep apnoea patients," *European Respiratory Journal*, 2007, pp. 748-758, vol. 30, No. 4.

Huang et al. "Dilation of the oropharynx via selective stimulation of the hypoglossal nerve." J. Neural Eng. 2005; 2:73-80.

Schwartz et al. "Therapeutic Electrical Stimulation of the Hypoglossal Nerve in Obstructive Sleep Apnea." Arch Otolaryngol Head Neck Surg/vol. 127, Oct. 2001 (8 pages).

Aziz, L. and Ejnell, H. "Obstructive Sleep Apnea Caused by Bilateral Vocal Fold Paralysis." Ear Nose Throat J. Apr. 2003; 82(4): 326-7.

Eckert, D. and Malhotra, A. "Pathophysiology of Adult Obstructive Sleep Apnea." Proceedings of the American Thoracic Society/vol. 5, 2008 (10 pages).

International Search Report and Written Opinion for corresponding Application No. PCT/US2015/015508, dated Jul. 13, 2015, (19 pages).

Examination Report on European Application No. 15706127.6 dated Jul. 28, 2017. 3 pages.

Examination Report on European Application No. 15706127.6 dated Mar. 22, 2019. 4 pages.

EP Office Action on EP Appl. Ser. No. 15706127.6 dated Apr. 26, 2022 (4 pages).

EP Office Action on EP Appl. Ser. No. 15706127.6 dated Mar. 29, 2022 (3 pages).

\* cited by examiner

SYSTEMS AND METHODS OF DETECTING AND TREATING OBSTRUCTIVE SLEEP APNEA

PRIORITY

This application claims priority to U.S. Provisional Application No. 61/938,615 filed on Feb. 11, 2014; 61/940,314 filed on Feb. 14, 2014; 61/940,764 filed on Feb. 17, 2014; and 61/942,616 filed on Feb. 20, 2014, the entire disclosures of which are hereby incorporated by reference in their entireties.

FIELD

The embodiments described herein relate to devices, systems and associated methods for treating sleeping disorders. More particularly, the embodiments described herein relate to devices, systems and methods for treating obstructive sleep apnea.

BACKGROUND

Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc.

Continuous positive airway pressure (CPAP) is a standard treatment for OSA. While CPAP is non-invasive and highly effective, it is not well tolerated by patients. Patient compliance for CPAP is often reported to be between 40% and 60%. Surgical treatment options for OSA are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibular advancement), and/ or they may be socially stigmatic (e.g., tracheostomy).

Hypoglossal nerve stimulation (HGNS) has been proposed for the treatment of obstructive sleep apnea. An example of an implantable hypoglossal nerve stimulation system is described in U.S. Pat. No. 7,809,442 to Bolea et al. Published data suggest that response to hypoglossal nerve stimulation varies across subjects. Before undergoing a surgical procedure to implant a hypoglossal nerve stimulation system, it would be desirable to understand the likelihood of therapeutic success, and make clinical judgments accordingly. It would also be desirable to consider various stimulation methodologies and adjunct therapies to hypoglossal nerve stimulation to improve outcomes thereof.

SUMMARY

To address these and other unmet needs, the present disclosure provides, in exemplary non-limiting embodiments, systems, devices, and methods for effective detection and treatment of obstructive sleep apnea. In particular, the present disclosure is directed to, among other things, implantable devices that stimulate the hypoglossal nerve to improve the function of the upper airway during sleep. The present disclosure is also directed to analysis techniques and the use of those techniques to identify and treat sleep apnea. Some of those techniques include analyzing a respiratory waveform to identify features and characteristics of multiple respiratory waveforms, individual respiratory waveforms, and portions of respiratory waveforms to identify the presence of airway obstruction and the presence of an obstructive sleep apnea event.

The present disclosure further provides, in one example embodiment, a method for treating obstructive sleep apnea by first performing an assessment of the patient that involves observing the patient's upper airway during a tongue protrusion maneuver. The assessment may, for example, be done using endoscopy to observe the upper airway while the patient is awake in the supine position. The tongue protrusion maneuver may, for example, involve the patient volitionally protruding the tongue to its maximal extent with the mouth open or the lips loosely touching the tongue. The tongue protrusion maneuver may mimic the effect of genioglossus activation by hypoglossal nerve stimulation (HGNS). Thus, an adequate increase in airway size during the tongue protrusion maneuver may be indicative of likely therapeutic success with HGNS. If the assessment shows an adequate increase in airway size during the maneuver, a HGNS device may be implanted in the patient with a higher confidence in a successful outcome. The principles of the present disclosure may be applied to other therapeutic interventions for OSA involving the upper airway. Alternative methods of screening patients to identify candidates suitable for therapies disclosed herein are contemplated. Such alternative methods include, but are not limited to Drug Induced Sleep Endoscopy as well as ways/mechanisms for imaging, visualizing or otherwise monitoring the upper airway anatomy of a candidate with the candidate subject to the influences of drugs or otherwise conducting said imaging, visualizing, or other monitoring while the patient is asleep.

According to one aspect of the present disclosure, a method of providing a sleep apnea nerve stimulation therapy to a subject may include detecting a respiratory waveform of the subject with a sensor. The sensor may be configured for coupling to the subject. The respiratory waveform may include a plurality of respiratory cycles each corresponding to at least one of a breath and an attempted breath of the subject. The method may also include identifying a breathing pattern within the respiratory waveform over a period of time. The breathing pattern may include a repeating pattern of a plurality of respiratory cycles followed by at least one respiratory cycle corresponding to a disordered breathing event. The method may also include generating a series of stimulation pulses with an implantable nerve stimulator configured for coupling to a hypoglossal nerve of the subject. The series of stimulation pulses may be coordinated with the breathing pattern.

According to aspects of the present disclosure, the method above may also include one or more of the following features. The subject may be a simulated subject and the respiratory waveform of the subject may be provided by a respiratory waveform simulator configured to generate the breathing pattern. The generating of the series of stimulation pulses coordinated with the breathing pattern may include the generating of a first stimulation pulse during the plurality of respiratory cycles and the generating of a second stimulation pulse during the at least one respiratory cycle corresponding to the disordered breathing event. The first stimulation pulse may be at a first amplitude and the second stimulation pulse may be at a second amplitude that is greater than the first amplitude. Receiving a command to initiate the nerve stimulation therapy and commencing an initial period when no stimulation is provided so as to allow the subject to fall asleep. The breathing pattern may be determined from a detection of at least one of a signal peak, a signal minimum, an expiration detection, and an inspiration detection. The breathing pattern may include a trend defined by at least one of the plurality of respiratory cycles, a plurality of peak magnitudes of the plurality of respiratory cycles, a plurality of minima magnitudes of the plurality of respiratory cycles, a plurality of expiration detections of the plurality of respiratory cycles, and a plurality of inspiration detections of the plurality of respiratory cycles. Identifying repetitions of the breathing pattern within the respiratory waveform to confirm the occurrence of the disordered breathing event.

According to another aspect of the present disclosure, an implantable nerve stimulation system may be configured to deliver a stimulation therapy. The system may include a sensor configured to detect a respiration signal of the subject. The respiration signal may define a respiratory waveform of the subject. The system may also include a stimulation electrode configured to deliver the stimulation therapy to a hypoglossal nerve of the subject. The system may also include a processor communicating with the sensor and the stimulation electrode. The processor may be configured to receive an input including the respiratory waveform and further configured to generate a therapy signal responsive to the input. The therapy signal may include the stimulation therapy. The respiratory waveform may include a plurality of respiratory cycles each corresponding to at least one of a breath and an attempted breath of the subject. The respiratory waveform may further include a breathing pattern over a period of time. The breathing pattern may include a repeating pattern of a plurality of respiratory cycles followed by at least one respiratory cycle corresponding to a disordered breathing event. The therapy signal may include a series of stimulation pulses. The series of stimulation pulses may be coordinated with the breathing pattern.

According to aspects of the present disclosure, the system above may include one or more of the following features. The subject may be a simulated subject. The respiratory waveform of the subject may be provided by a respiratory waveform simulator configured to generate the breathing pattern. The series of stimulation pulses coordinated with the breathing pattern may include a first stimulation pulse timed with the plurality of respiratory cycles and a second stimulation pulse timed with the at least one respiratory cycle corresponding to the disordered breathing event. The first stimulation pulse may be at a first amplitude and the second stimulation pulse may be at a second amplitude that is greater than the first amplitude. Prior to the generation of the therapy signal, the stimulation therapy may further include an initial period when no stimulation is provided so as to allow the subject to fall asleep. The initial period may subsequently be followed by the therapy signal. The breathing pattern may be determined from a detection of at least one of a signal peak, a signal minimum, an expiration detection, and an inspiration detection. The breathing pattern may include a trend defined by at least one of the plurality of respiratory cycles, a plurality of peak magnitudes of the plurality of respiratory cycles, a plurality of minima magnitudes of the plurality of respiratory cycles, a plurality of expiration detections of the plurality of respiratory cycles, and a plurality of inspiration detections of the plurality of respiratory cycles. A nerve cuff, the nerve cuff including the stimulation electrode.

According to another aspect of the present disclosure, a method of providing a sleep apnea nerve stimulation therapy to a subject may include detecting a respiratory waveform of the subject with a sensor configured for coupling to the subject. The respiratory waveform may include a plurality of respiratory cycles each corresponding to at least one of a breath and an attempted breath of the subject. The method may also include commencing a first therapy of the nerve stimulation therapy. The first therapy may include an implantable nerve stimulator generating a series of first stimulation pulses configured for delivery to a hypoglossal nerve of the subject. Each stimulation pulse of the series of first stimulation pulses may be timed to coincide with at least one of an output of a timer and a detection of a first feature of one of the plurality of respiratory cycles. The method may also include transitioning from the first therapy to a second therapy of the nerve stimulation therapy. The second therapy may include the implantable nerve stimulator generating a series of second stimulation pulses configured for delivery to the hypoglossal nerve of the subject. Each stimulation pulse of the series of second stimulation pulses may be timed to coincide with a detection of a second feature of at least two of the plurality of respiratory cycles.

According to aspects of the present disclosure, the method above may include one or more of the following features. The subject may be a simulated subject and the respiratory waveform of the subject may be a simulated respiratory waveform provided by a respiratory waveform simulator. The series of first stimulation pulses and the series of second stimulation pulses may have a same amplitude. The series of first stimulation pulses each may have a first amplitude and the series of second stimulation pulses each may have a second amplitude, the second amplitude being greater than the first amplitude. The output of the timer may be asynchronous with subject breathing. Commencing of the first therapy may include an initial period when no stimulation is provided so as to allow the subject to fall asleep, the initial period subsequently followed by the generation of the series of first stimulation pulses. The first feature may be at least one of a signal peak, a signal minimum, an expiration detection, and an inspiration detection. The second feature may be at least one of a plurality of signal peaks, a plurality of signal minima, a plurality of expiration detections, a plurality of inspiration detections, and at least one inspiration detection and at least one expiration detection. The second feature may be a trend of the plurality of respiratory cycles. The trend may correspond to a plurality of peak magnitudes of the plurality of respiratory cycles, a plurality of minima magnitudes of the plurality of respiratory cycles, a plurality of expiration detections of the plurality of respiratory cycles, and a plurality of inspiration detections of the plurality of respiratory cycles.

According to another aspect of the present disclosure, an implantable nerve stimulation system may be configured to deliver a stimulation therapy. The system may include a sensor configured to detect a respiration signal of the subject, the respiration signal defining a respiratory waveform of the subject. The system may also include a stimulation electrode configured to deliver the stimulation therapy to a hypoglossal nerve of the subject. The system may also include a processor communicating with the sensor and the stimulation electrode. The processor may be configured to receive an input comprising the respiratory waveform and further configured to generate a therapy signal responsive to the input. The therapy signal may include the stimulation therapy. The respiratory waveform may include a plurality of respiratory cycles each corresponding to at least one of a breath and an attempted breath of the subject. The stimulation therapy may include a first therapy that transitions to a second therapy. The first therapy may include a series of first stimulation pulses with each stimulation pulse of the series of first stimulation pulses timed to coincide with at least one of an output of a timer and a detection of a first feature of one of the plurality of respiratory cycles. The second therapy may include a series of second stimulation pulses with each stimulation pulse of the series of second stimulation pulses timed to coincide with a detection of a second feature of at least two of the plurality of respiratory cycles.

According to other aspects of the present disclosure, the system above may include one or more of the following features. The subject may be a simulated subject and the respiratory waveform of the subject may be a simulated respiratory waveform provided by a respiratory waveform simulator. The series of first stimulation pulses and the series of second stimulation pulses may have a same amplitude. The series of first stimulation pulses each may have a first amplitude and the series of second stimulation pulses each may have a second amplitude, the second amplitude being greater than the first amplitude. The output of the timer may be asynchronous with subject breathing. The stimulation therapy may include an initial period prior to the first therapy when no stimulation is provided so as to allow the subject to fall asleep, the initial period subsequently followed by the first therapy. The first feature may be at least one of a signal peak, an expiration detection, and an inspiration detection. The second feature may be at least one of a plurality of signal peaks, a plurality of signal minima, a plurality of expiration detections, a plurality of inspiration detections, and at least one inspiration detection and at least one expiration detection. The second feature may be a trend of the plurality of respiratory cycles, the trend corresponding to a plurality of peak magnitudes of the plurality of respiratory cycles, a plurality of minima magnitudes of the plurality of respiratory cycles, a plurality of expiration detections of the plurality of respiratory cycles, and a plurality of inspiration detections of the plurality of respiratory cycles. A nerve cuff, the nerve cuff including the stimulation electrode.

According to another aspect of the present disclosure, a method of applying a sleep apnea nerve stimulation therapy to a subject may include detecting a respiratory waveform of the subject with a sensor coupled to the subject, the respiratory waveform including a plurality of peak magnitudes corresponding to a time period. The method may also include identifying a respiratory trend based on a comparison of the plurality of peak magnitudes over the time period. The trend may include an increase in peak magnitudes over the time period or a decrease in peak magnitudes over the time period. The method may also include projecting the trend to a future projected time subsequent to the time period when the projected trend will intersect a disordered breathing threshold. The method may also include commencing a corrective nerve stimulation therapy subsequent to the time period.

According to other aspects of the disclosure, the method above may include one or more of the following features. The subject may be a simulated subject and the respiratory waveform of the subject may be provided by a respiratory waveform simulator configured to generate the respiratory waveform. Commencing an initial nerve stimulation therapy during the time period and prior to the commencing of the corrective nerve stimulation therapy, the corrective nerve stimulation therapy having a greater amplitude than the initial stimulation therapy. Transitioning from the corrective nerve stimulation therapy to the initial nerve stimulation therapy at a time subsequent to the future projected time. Commencing an initial setting of a nerve stimulation device, the initial setting configured to withhold therapy during at least a portion of the time period prior to the commencing of the corrective nerve stimulation therapy. Transitioning from the corrective nerve stimulation therapy to recommence the initial setting at a time subsequent to the future projected time. The corrective nerve stimulation therapy may be configured to reduce a slope of the trend. The corrective nerve stimulation therapy may be configured to flatten a slope of the trend. The corrective nerve stimulation therapy may be configured to reverse the trend. The corrective nerve stimulation therapy may be configured to open an airway of the subject during a duration of a disordered breathing event. The corrective nerve stimulation therapy may be configured to terminate after a conclusion of a disordered breathing event corresponding to the intersection of the projected trend and the disordered breathing threshold. The sensor may be at least one of an impedance sensor, an airflow sensor, a pressure sensor, and an accelerometer. The disordered breathing threshold may be based on at least one of the plurality of peak magnitudes. The disordered breathing threshold may be based on parameter derived from at least one of the plurality of peak magnitudes, the disordered breathing threshold being a percentage greater or less than the parameter. The percentage may be at least one of approximately 10%, 15%, 20%, and 25%. Commencing of the corrective nerve stimulation therapy may take place before the future projected time. Commencing of the corrective nerve stimulation therapy may take place in response to a detected peak magnitude that exceeds the disordered breathing threshold.

According to another aspect of the present disclosure, an implantable nerve stimulation system may be configured to deliver a stimulation therapy. The system may include a sensor configured to detect a respiration signal of the subject, the respiration signal defining a respiratory waveform of the subject and a plurality of peak magnitudes corresponding to a time period. The respiratory waveform may include a respiratory trend based on a comparison of the plurality of peak magnitudes over the time period. The trend may include an increase in peak magnitudes over the time period or a decrease in peak magnitudes over the time period. A stimulation electrode may be configured to deliver the stimulation therapy to a hypoglossal nerve of the subject. A processor may communicate with the sensor and the stimulation electrode, the processor configured to receive an input comprising the respiratory waveform and further configured to generate a correcting therapy signal responsive to the input. The correcting therapy signal may include the stimulation therapy. The correcting therapy signal may be generated subsequent to the time period when a projection of the trend to a future projected time intersects with a disordered breath threshold.

According to other aspects of the present disclosure, the system above may include one or more of the following features. The subject may be a simulated subject and the respiratory waveform of the subject may be provided by a respiratory waveform simulator configured to generate the respiratory waveform. The correcting nerve stimulation therapy may be configured to reduce a slope of the trend. The correcting nerve stimulation therapy may be configured to flatten a slope of the trend. The correcting nerve stimulation therapy may be configured to reverse the trend. The correcting nerve stimulation therapy may be configured to open an airway of the subject during a duration of a disordered breathing event. The correcting nerve stimulation therapy may be configured to terminate after a conclusion of a disordered breathing event corresponding to the intersection of the projected trend and the disordered breathing threshold. The sensor may be at least one of an impedance sensor, an airflow sensor, a pressure sensor, and an accelerometer. The disordered breathing threshold may be based on at least one of the plurality of peak magnitudes. The disordered breathing threshold may be based on a parameter derived from at least one of the plurality of peak magnitudes, the disordered breathing threshold being a percentage greater or less than the parameter. The percentage may be at least one of approximately 10%, 15%, 20%, and 25%. The generating of the correcting nerve stimulation therapy may take place before the future projected time. The generating of the correcting nerve stimulation therapy may take place in response to a detected peak magnitude that exceeds the disordered breathing threshold. A nerve cuff, the nerve cuff including the stimulation electrode.

According to another aspect of the present disclosure, a method of applying a sleep apnea nerve stimulation therapy to a subject may include detecting a respiratory waveform of the subject with a sensor coupled to the subject. The respiratory waveform may include at least one peak magnitude and at least one respiratory cycle both corresponding to a respiratory time period. The method may also include identifying an inspiration portion of the at least one respiratory cycle corresponding to at least one of an inspiration or an attempted inspiration of the subject, the inspiration portion corresponding to an inspiratory time period. The method may also include comparing the inspiratory time period to the respiratory time period to indicate a disordered breathing event. The method may also include commencing a corrective nerve stimulation therapy.

According to other aspects of the present disclosure, the method above may include one or more of the following features. The subject may be a simulated subject and the respiratory waveform of the subject may be provided by a respiratory waveform simulator configured to generate the respiratory waveform. The inspiration may be bounded by a beginning of inspiration and an ending of inspiration indicated in the respiratory waveform, the ending of inspiration corresponding to an initial detection of a peak subsequent to the beginning of inspiration. The inspiration may be bounded by a beginning of inspiration and an ending of inspiration indicated in the respiratory waveform, the ending of inspiration corresponding to a last detection of a peak subsequent to the beginning of inspiration. The inspiration may be bounded by a beginning of inspiration and an ending of inspiration indicated in the respiratory waveform, the ending of inspiration corresponding to a plateau observed in the respiratory waveform subsequent to the beginning of inspiration. The ending of inspiration may correspond to an end of the plateau. The disordered breathing event may be indicated when the inspiratory time period is 40% or more of the respiratory time period. The disordered breathing event may be indicated when the inspiratory time period is 50% or more of the respiratory time period. The disordered breathing event may be indicated when the inspiratory time period is 60% or more of the respiratory time period.

According to another aspect of the present disclosure, an implantable nerve stimulation system configured to deliver a stimulation therapy may include a sensor configured to detect a respiration signal of the subject. The respiration signal may define a respiratory waveform of the subject including at least one peak magnitude and at least one respiratory cycle both corresponding to a respiratory time period. The at least one respiratory cycle may include an inspiration portion corresponding to at least one of an inspiration or an attempted inspiration of the subject, the inspiration portion corresponding to an inspiratory time period. The system may also include a stimulation electrode configured to deliver the stimulation therapy to a hypoglossal nerve of the subject. The system may also include a processor communicating with the sensor and the stimulation electrode. The processor may be configured to receive an input comprising the respiratory waveform and further configured to generate a corrective therapy signal responsive to the input. The corrective therapy signal may include the stimulation therapy, the corrective therapy signal being generated when a comparison of the inspiratory time period to the respiratory time period indicates a disordered breathing event.

According to other aspects of the present disclosure, the system above may include one or more of the following features. The inspiration may be bounded by a beginning of inspiration and an ending of inspiration indicated in the respiratory waveform, the ending of inspiration corresponding to an initial detection of a peak subsequent to the beginning of inspiration. The inspiration may be bounded by a beginning of inspiration and an ending of inspiration indicated in the respiratory waveform, the ending of inspiration corresponding to a last detection of a peak subsequent to the beginning of inspiration. The inspiration may be bounded by a beginning of inspiration and an ending of inspiration indicated in the respiratory waveform, the ending of inspiration corresponding to a plateau observed in the respiratory waveform subsequent to the beginning of inspiration. The ending of inspiration may correspond to an end of the plateau. The disordered breathing event may be indicated when the inspiratory time period is 40% or more of the respiratory time period. The disordered breathing event may be indicated when the inspiratory time period is 50% or more of the respiratory time period. The disordered breathing event may be indicated when the inspiratory time period is 60% or more of the respiratory time period. A nerve cuff, the nerve cuff including the stimulation electrode.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles.

DETAILED DESCRIPTION

As described in U.S. Pat. Nos. 7,809,442 and 8,417,343, both of which are incorporated by reference herein in their entireties, a hypoglossal nerve stimulation device may be implanted or disposed to interface with the hypoglossal nerve to allow effective stimulation of the nerve and the resulting movement of the tongue to open the upper airway of a human subject.

The following detailed description should be read with reference to the drawings in which similar elements in different drawings are numbered the same. The drawings, which are not necessarily to scale, depict illustrative embodiments and are not intended to limit the scope of the disclosure.

Description of Fully Implanted Neurostimulator System

Figure 1:
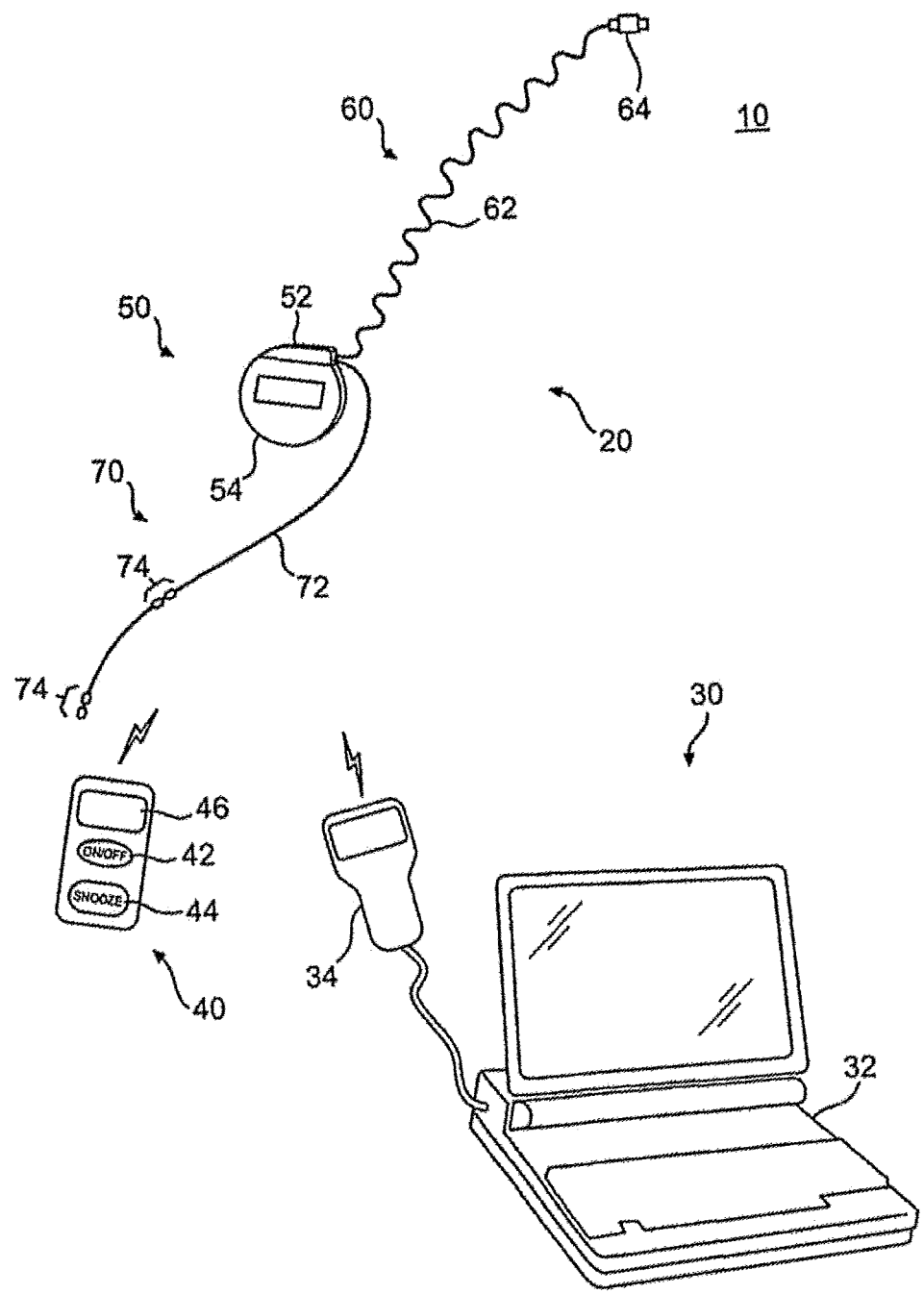
FIG. 1 is a schematic diagram showing a fully implanted neurostimulator system with associated physician programmer and patient controller for treating obstructive sleep apnea.

With reference to FIG. 1, a neurostimulator system 10 including implanted components 20, physician programmer 30 and patient controller 40 are shown schematically. The implanted components of the system 10 may generally include an implanted neurostimulator (INS) 50 (a.k.a., an implanted pulse generator (IPG)), an implanted stimulation lead (or leads) 60, and an implanted respiration sensing lead (or leads) 70. The INS 50 generally includes a header 52 for connection of the leads 60/70, and a hermetically sealed housing 54 for the associated electronics and long-life or rechargeable battery (not visible). The stimulation lead 60 generally includes a lead body 62 with a proximal connector and a distal nerve electrode cuff 64. The respiration sensing lead 70 generally includes a lead body 72 with a proximal connector and one or more sensors 74 disposed on or along a distal portion thereof. Suitable designs of the INS 50, stimulation lead 60 and respiration sensing lead 70 are described in more detail hereinafter.

Figure 2:
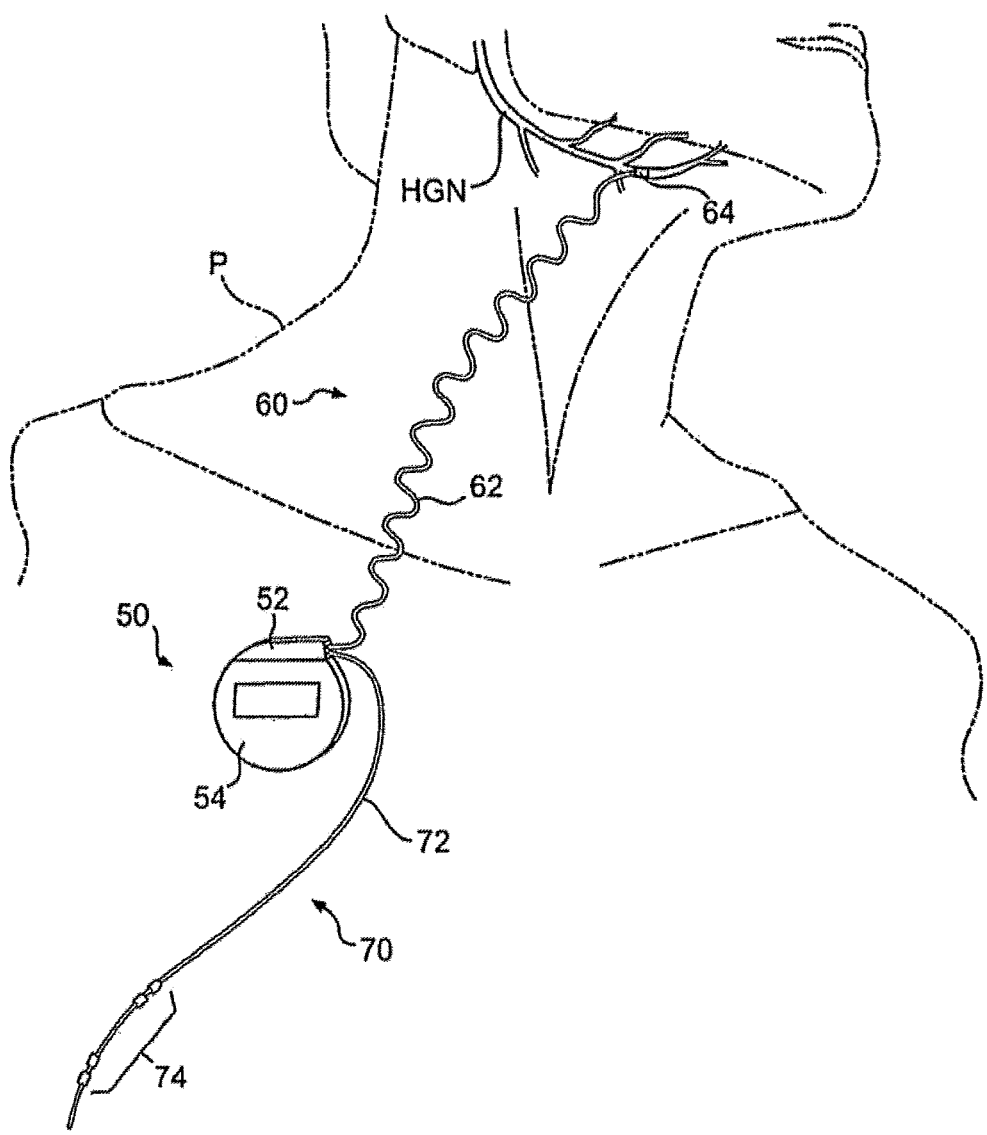
FIG. 2 is a schematic diagram showing the implantable components of FIG. 1 implanted in a patient.

As shown in FIG. 2, and by way of example, not limitation, the implanted components 20 of the neurostimulator system 10 are implanted in a patient P with the INS 50 disposed in a subcutaneous pocket, the stimulation lead body 62 disposed in a subcutaneous tunnel, the nerve cuff electrode 64 disposed on a nerve (e.g., hypoglossal nerve (HGN)) innervating a muscle (e.g., genioglossus muscle, not shown) controlling the upper airway, the respiration sensing lead body 72 disposed in a subcutaneous tunnel, and the respiration sensors 74 disposed adjacent lung tissue and/or intercostal muscles outside the pleural space. It should be appreciated that the nerve cuff electrode 64 may be replaced with another type of stimulation electrode assembly, such as a stimulation electrode assembly with a cylindrical lead having one or more stimulation electrodes positioned close to the HNG.

Generally, electrical stimulus is delivered by the INS 50 via the stimulation lead 60 to a nerve innervating a muscle controlling upper airway patency to mitigate obstruction thereof. To reduce nerve and muscle fatigue, the stimulus may be delivered for only a portion of the respiratory cycle, such as during inspiration which corresponds to negative pressure in the upper airway. Stimulation may be thus triggered as a function of respiration as detected by respiration sensing lead 70 in a closed-loop feedback system. By way of example, the stimulus may be triggered to turn on at the end of expiration (or at the beginning of inspiration), and triggered to turn off at the beginning of expiration (or at the end of inspiration). Triggering the stimulus as a function of expiration improves capture of the entire inspiratory phase, including a brief pre-inspiratory phase of about 300 milliseconds, thus more closely mimicking normal activation of upper airway dilator muscles. Over-stimulation may cause nerve and/or muscle fatigue, but a 40% to 50% duty cycle may be safely tolerated, thus enabling limited over-stimulation. As an alternative, stimulus may be delivered independent of actual respiration wherein the stimulus duty cycle is set for an average inspiratory duration at a frequency approximately equal to an average respiratory cycle.

Stimulus may be delivered to one or more of a variety of nerve sites to activate one muscle or muscle groups controlling patency of the upper airway. For example, stimulation of the genioglossus muscle via the hypoglossal nerve moves or otherwise stiffens the anterior portion of the upper airway, thereby decreasing the critical pressure at which the upper airway collapses during inspiration and reducing the likelihood of an apnea or hypopnea event occurring during sleep. Because the systems described herein work at the level of the tongue, it may be desirable to combine this therapy with a therapy (e.g., UPPP or palatal implant) that work at the level of the soft palate, thus increasing efficacy for a broader range of patients.

With reference back to FIG. 1, the physician programmer 30 may comprise a computer 32 configured to control and program the INS 50 via a wireless link to a programming wand 34. The physician programmer 30 may be resident in a sleep lab where the patient undergoes a polysomnographic (PSG) study during which the patient sleeps while the INS 50 is programmed to optimize therapy.

The patient controller 40 may comprise control circuitry and an associated user interface to allow the patient to control the system via a wireless link while at home, for example. The patient controller 40 may include a power switch 42 to turn the system on and slowly ramp up when the patient goes to sleep at night, and turn it off when the patient wakes in the morning. A snooze switch 44 may be used to temporarily put the INS 50 in a standby mode for a preprogrammed period of time to allow the patient to temporarily wake, after which the INS 50 turns back on and ramps up to the desired stimulus level. Display 46 may be configured to be a dash-board-like display, and may be any suitable display available to those of ordinary skill in the art, such as, for example, an LED or LCD display. Furthermore, information may be communicated to the patient controller 40 for display purposes by any suitable means known to those of ordinary skill in the art. For example, communication of information may be achieved through inductively coupled or radio frequency telemetry. The patient controller 40 may also have programmability to adjust stimulus parameters (e.g., amplitude) within a pre-set range determined by the physician in order to improve efficacy and/or to reduce sensory perception, for example. Optionally, the patient controller 40 may be configured to function as the programming wand 34 of the physician programmer 30. A library of electrical stimulation parameter settings can be programmed into the INS. These settings listed in the library may be selected by the patient manually using the patient programmer based on, for example: (1) direct patient perception of comfort during stimulation; (2) a log of the most successful settings compiled by the software in the INS (assumes apnea/hypopnea detection capability); (3) a sleep physician's or technician's assessment of the most effective stimulation as determined during a sleep study; and/or (4) a list of the most effective parameters produced for a particular class of patient or other. The electrical stimulation parameters described above may be adjusted based on patient position as detected by a position sensor within the INS. The best setting for a given position may be determined by, for example: (1) a log of the most successful settings compiled or learned by the software in the INS (assumes apnea/hypopnea detection capability); (2) a sleep physician's or technician's assessment of the most effective stimulation as determined during a sleep study; and/or (3) a list of the most effective parameters produced for a particular class of patient or other.

During use optimal stimulation signal parameters (e.g., stimulation intensity, respiratory phase adjustment) may be selected via, e.g., the patient controller 40. The stimulation signal parameters that may be adjusted to optimize efficacy (as measured by apnea index, hypopnea index, respiratory disturbance index, apnea-hypopnea index, and other obstructive sleep apnea efficacy measures) of the delivered stimulation may include, but not be limited to, pulse amplitude, pulse frequency, pulse width, duty cycle, phase adjust, etc.

Figure 3:
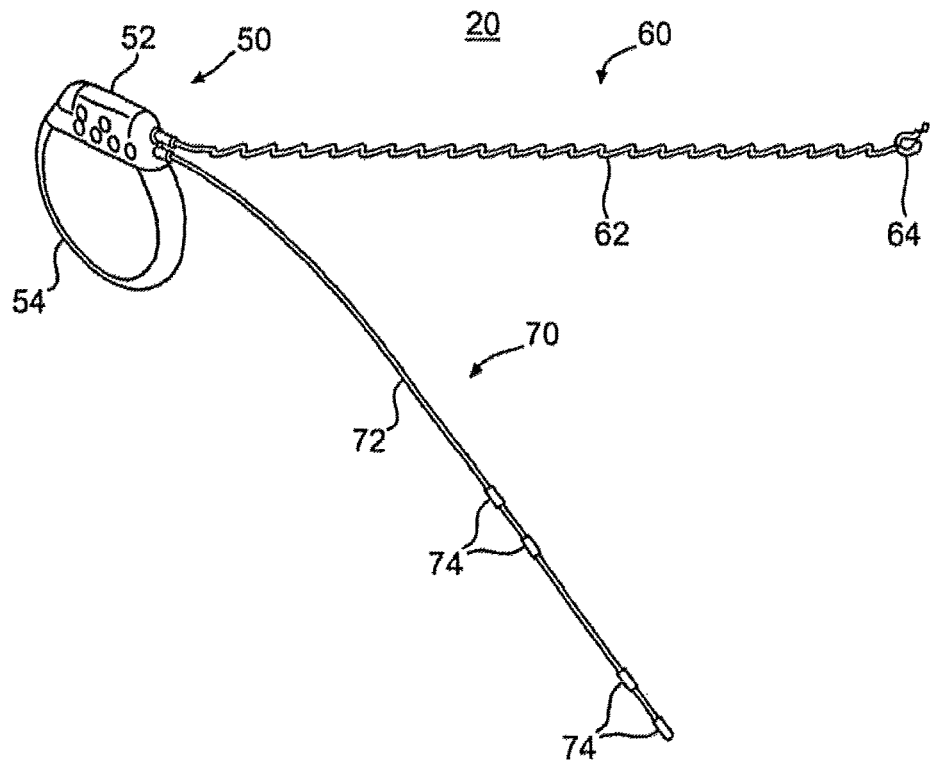
FIG. 3 is a perspective view of the implantable components shown in FIG. 1.

With reference to FIG. 3, the implanted components 20 are shown schematically with more detail. The implanted components include INS 50, stimulation lead 60, and respiration sensing lead 70. The INS 50 includes header 52 and housing 54. The stimulation lead 60 includes lead body 62 and nerve cuff electrode 64. The respiration sensing lead 70 includes lead body 72 and respiration sensors 74 (e.g., impedance sensing electrodes).

Figure 4:
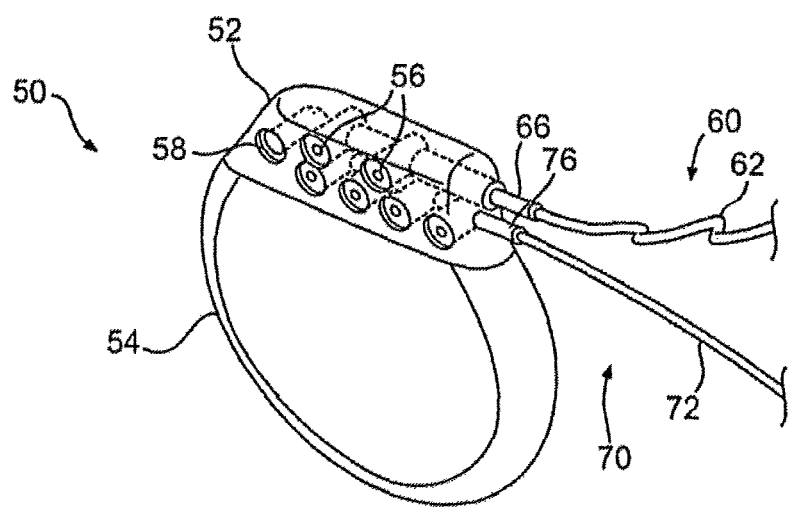
FIG. 4 is a detailed perspective view of the implantable neurostimulator (INS) shown in FIG. 3.

With reference to FIG. 4, the INS 50 is shown schematically in more detail. The INS 50 includes header 52 that may be formed using conventional molding or casting techniques and may comprise conventional materials such as epoxy or polyurethane (e.g., Tecothane brand polyurethane). The housing 54 may be formed using conventional stamping or forming techniques and may comprise conventional materials such as titanium or ceramic. The housing 54 may include one or more isolated electrodes, and/or if a conductive material is used for the housing 54, the housing 54 may comprise an electrode, which may be used for respiratory sensing, for example. The housing 54 may be hermetically sealed to the header 52 using conventional techniques. The header 52 may include two or more receptacles for receiving the proximal connectors 66/76 of the stimulation lead body 62 and respiration sensing lead body 72. The connectors 66/76 may comprise a conventional design such as IS1 or other in-line designs. The header 52 may also include set screw seals and blocks 56 for receiving set screws (not shown) that establish electrical contact between the INS 50 and the conductors of the leads 60/70 via connectors 66/76, and that establish mechanical fixation thereto. Some electrical contact may be achieved through spring type or cam-locked mechanisms. As shown, two set screw arrangements 56 are shown for the stimulation lead 60 and four set screw arrangements 56 are shown for the respiration sensing lead 70, but the number may be adjusted for the number of conductors in each lead. A hole 58 may be provided in the header 52 for securing the INS 50 to subcutaneous tissue using a suture at the time of implantation.

The INS 50 may comprise a conventional implanted neurostimulator design used in neurostimulation applications, such as those available from Texcel (US), CCC (Uruguay) and NeuroTECH (Belgium), but modified for the present clinical application in terms of stimulation signal parameters, respiratory signal processing, trigger algorithm, patient control, physician programming, etc. The INS may contain a microprocessor and memory for storing and processing data and algorithms. Algorithms may be in the form of software and/or firmware, for example. One of several different embodiments of the neurostimulator may be implemented. For example, the neurostimulator may be an internal/implanted neurostimulator (INS) powered by a long-life primary battery or rechargeable battery, or an external neurostimulator (ENS) wirelessly linked (e.g., inductive) to an implanted receiver unit connected to the leads. The INS (or the receiver unit of the ENS) may be implanted and optionally anchored in a number of different locations including a subcutaneous pocket in the pectoral region, the dorsal neck region, or cranial region behind the ear, for example.

The INS 50 may include a long-life battery (not shown) which requires periodic replacement after years of service. Alternatively, the INS may include a rechargeable power source such as a rechargeable battery or super capacitor that is used instead of the long-life battery. To facilitate recharging, the INS may include a receiver coil inductively linked to a transmitter coil that is connected to a recharging unit powered by a larger battery or line power. Because the patient is stationary while sleeping, recharging may be scheduled to occur sometime during sleep to eliminate the need to carry the recharging unit during daily activities. The transmitter coil and the receiver coil may be arranged coaxially in parallel planes to maximize energy transfer efficiency, and may be held in proximity to each other by a patch, garment, or other means as described with reference to the external neurostimulator embodiments. Other examples of neurostimulator designs will be described in more detail hereinafter.

Figure 5:
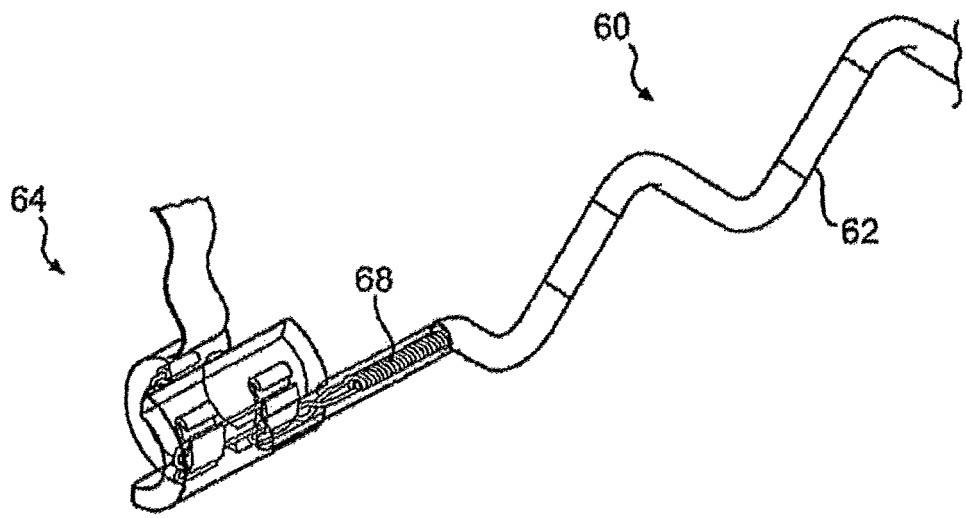
FIG. 5 is a detailed perspective view of a nerve cuff electrode and lead body shown in FIG. 3.

With reference to FIG. 5, the stimulation lead 60 may comprise a variety of different design embodiments and may be positioned at different anatomical sites. For example, a nerve cuff electrode(s) 64 may be attached to a nerve(s) innervating musculature affecting patency of the upper airway. As an alternative or in addition, the nerve cuff electrode 64 may be replaced with an intramuscular electrode and placed directly in the musculature affecting patency of the upper airway. The nerve electrode 64 may be attached to a specific branch of a nerve innervating the desired muscle(s), or may be attached to a proximal trunk of the nerve in which a specific fascicle innervating the desired muscle(s) is targeted by steering the stimulus with multiple electrodes. One or more electrodes may be used for attachment to one or more portions of nerves on one side (unilateral) of the body, or one or more electrodes may be used for attachment to one or more portions of nerves on both sides (bilateral) of the body. Variations in lead body 62 and electrode 64 design as well as variations in the target stimulation site or sites will be described in more detail hereinafter.

With continued reference to FIG. 5, the lead body 62 may be sigmoid shaped, for example, to reduce strain applied to the cuff electrode 64 when the lead body 62 is subject to movement. The sigmoid shape, which may alternatively comprise a variety of other waveform shapes, may have a wavelength of approximately 1.0 to 1.5 cm, and an amplitude of approximately 0.75 to 1.5 cm, for example. The lead body 62 may comprise a tubular jacket with electrical conductors 68 extending therein. The tubular jacket may comprise extruded silicone having an outside diameter of approximately 0.047 inches and an inside diameter of approximately 0.023 inches, for example. The tubular jacket may optionally have a covering of co-extruded polyurethane, for example, to improve durability. The conductors 68, shown in a transparent window in the jacket for purposes of illustration only, may comprise a bifilar coil of insulated (e.g., ETFE) braided stranded wire (BSW) of MP35NLT material. The number of conductors 68 is shown as two, but may be adjusted depending on the desired number of independent electrodes used.

Figure 6:
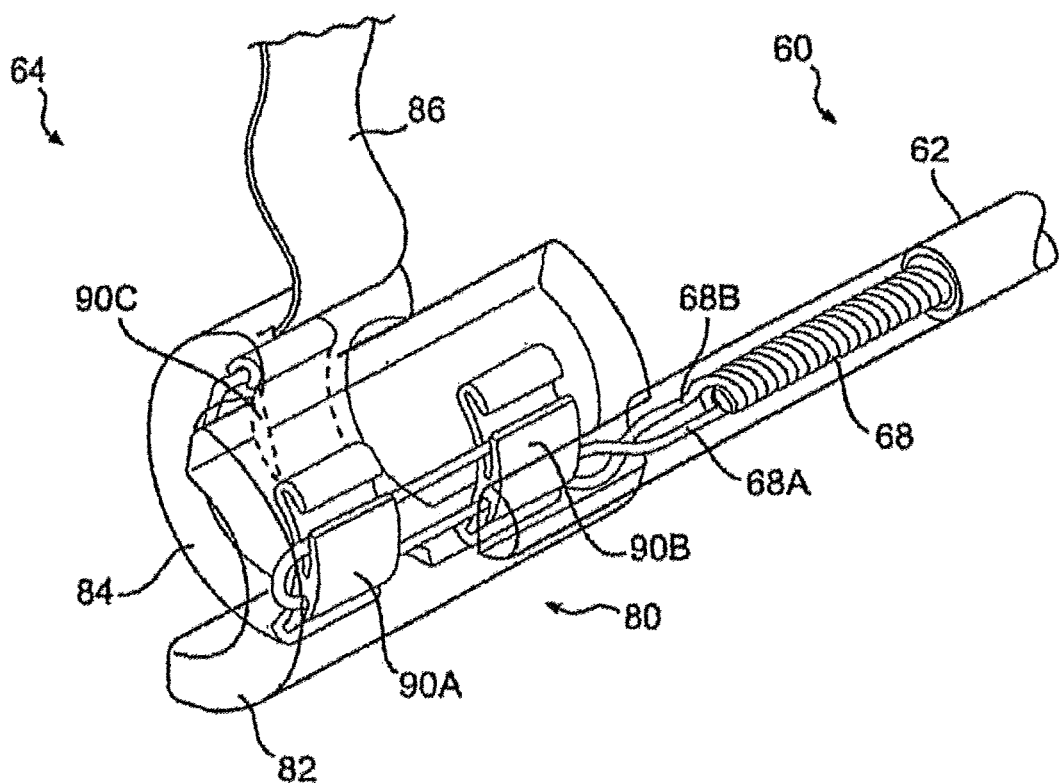
FIG. 6 is a close-up detailed perspective view of the nerve cuff electrode shown in FIG. 3.

With reference to FIG. 6, the nerve cuff electrode 64 may comprise a cuff body 80 having a lateral (or superficial) side 82 and a medial (or contralateral, or deep) side 84. The medial side 84 is narrower or shorter in length than the lateral side 82 to facilitate insertion of the medial side 84 around a nerve such that the medial side is on the deep side of the nerve and the lateral side is on the superficial side of the nerve. This configuration reduces the dissection of nerve branches and vascular supply required to get the cuff around a nerve. For the nerve cuff implant sites discussed herein, the medial side 84 may have a length of less than 6 mm, and preferably in the range of approximately 3 to 5 mm, for example. The lateral side 82 may have a length of more than 6 mm, and preferably in the range of approximately 7 to 8 mm, for example. The cuff body 80 may be compliant and may be available in different sizes with an inside diameter of approximately 2.5 to 3.0 mm or 3.0 to 3.5 mm, for example. The cuff size may also be adjusted depending on the nominal diameter of the nerve at the site of implantation. The cuff body 80 may have a wall thickness of approximately 1.0 mm and may be formed of molded silicone, for example, and may be reinforced with imbedded fibers or fabrics. An integral tow strap 86 may be used to facilitate wrapping the cuff around a nerve by first inserting the strap 86 under and around the deep side of the nerve and subsequently pulling the strap to bring the medial side 84 in position on the deep side of the nerve and the lateral side 82 on the superficial side of the nerve.

With continued reference to FIG. 6, the nerve cuff electrode 64 includes electrode contacts 90A, 90B, and 90C imbedded in the body 80 of the cuff, with their inside surface facing exposed to establish electrical contact with a nerve disposed therein. A transverse guarded tripolar electrode arrangement is shown by way of example, not limitation, wherein electrode contacts 90A and 90B comprise anodes transversely guarding electrode contact 90C which comprises a cathode.

With this arrangement, the anode electrodes 90A and 90B are connected to a common conductor 68A imbedded in the body 80, and the cathode electrode 90C is connected to an independent conductor 68B extending from the lateral side 82 to the medial side 84 and imbedded in the body 80. By using the conductors 68 to make connections within the body 80 of the cuff 64, fatigue stresses are imposed on the conductors rather than the electrode contacts 90A, 90B and 90C.

Figure 7:
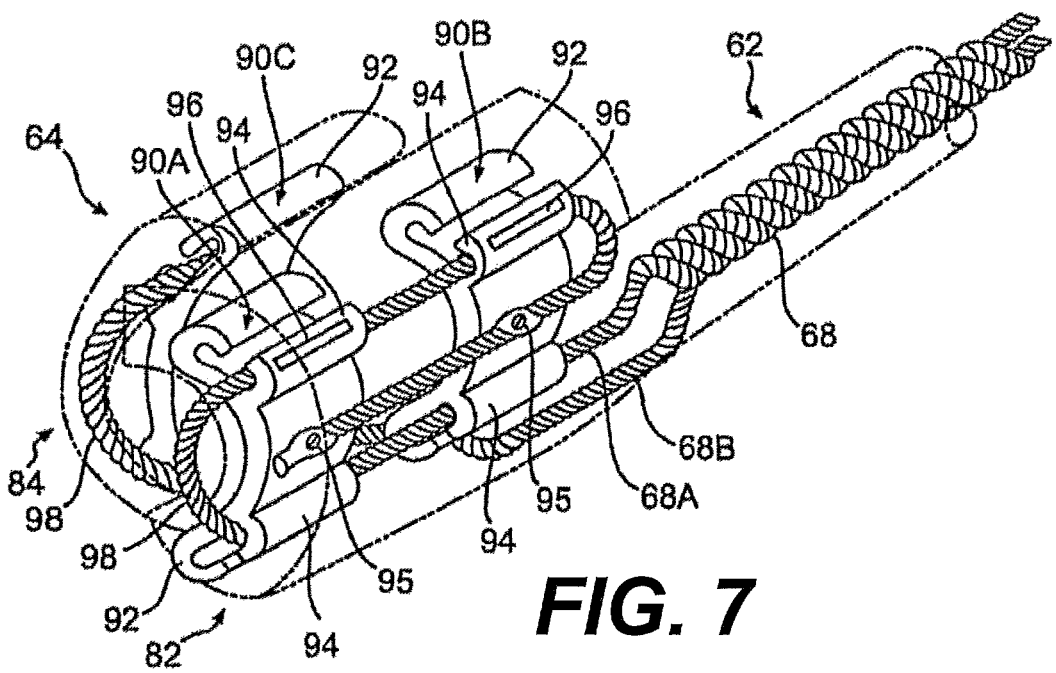
FIG. 7 is a detailed perspective view of the internal components of the nerve cuff electrode shown in FIG. 6.
Figure 8:
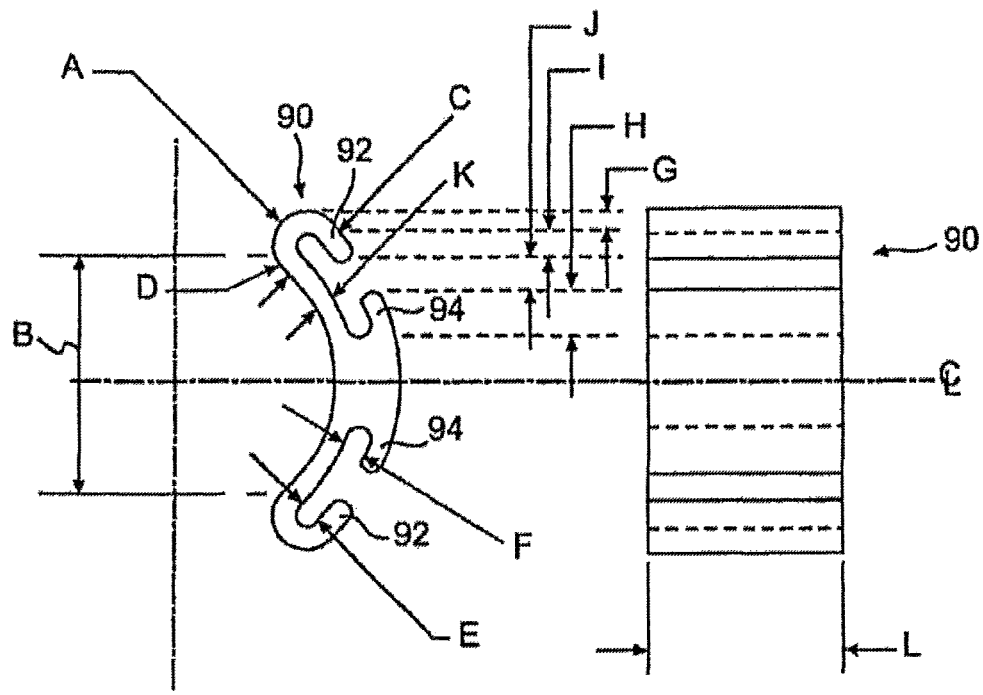
FIG. 8 shows side and end views of an electrode contact of the nerve cuff electrode shown in FIG. 7.

With additional reference to FIGS. 7 and 8, the electrode contacts 90A, 90B and 90C may thus be semi-circular shaped having an arc length of less than 180 degrees, and preferably an arc length of approximately 120 degrees, for example. Each electrode 90 may have two reverse bends (e.g., hooked or curled) portions 92 to provide mechanical fixation to the body 80 when imbedded therein. Each electrode 90 may also have two crimp tabs 94 defining grooves thereunder for crimping to the conductors 68 or for providing a pass-through. As shown in FIG. 7, conductor 68A passes through the grooves under the lower crimp tabs 94 of electrodes 90B and 90A, loops 98 around through the grooves under the upper crimp tabs 94 of electrodes 90A and 90B, is crimped 96 by the upper tabs 94 of electrodes 90A and 90B to provide mechanical and electrical connection, is looped again back between the crimp tabs 94 on the outside of the electrode contact 90, and is resistance spot welded 95 to provide redundancy in mechanical and electrical connection. Also as shown in FIG. 7, conductor 68B passes through the groove under the lower crimp tab 94 of electrode 90C, loops around through the groove under the upper crimp tab 94 of electrode 90C, and is crimped by the upper tab 94 of electrode 90C to provide mechanical and electrical connection. This arrangement avoids off-axis tensile loading at the crimp sites 96 which may otherwise fail due to stress concentration, and the looped portion 98 provides additional strain relief. FIG. 8 provides example dimensions (inches) of an electrode contact 90 for a 2.5 mm inside diameter cuff, wherein the electrode is formed of 90/10 or 80/20 platinum iridium alloy formed by wire EDM, for example. As illustrated, and as exemplary and approximate dimensions, electrode contact 90 may include a surface A having a full radius, a dimension B of 0.079 inches from tangent to tangent, a dimension C of 0.020 inches (3×), a radius of curvature D of 0.049 R with a 16 micro-inch RMS, a dimension E of 0.008 inches (2×), a dimension F of 0.0065 inches (+/−0.001 inches) (2×), a dimension G of 0.006 inches (+0.002 inches, −0.001 inches) (2×), a dimension H of 0.014 inches (2×), a dimension I of 0.010 inches (2×), a dimension J of 0.010 inches (2×), a dimension K of 0.006 inches (+/−0.001 inches), and a dimension of L of 0.120 inches.

Figure 9B:
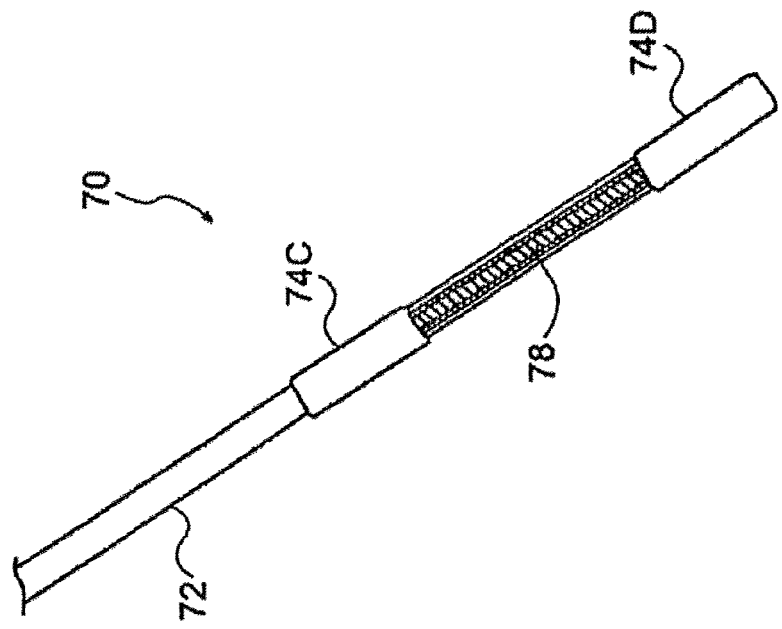
FIGS. 9A and 9B are perspective views of a respiration sensing lead shown in FIG. 3.
Figure 9A:
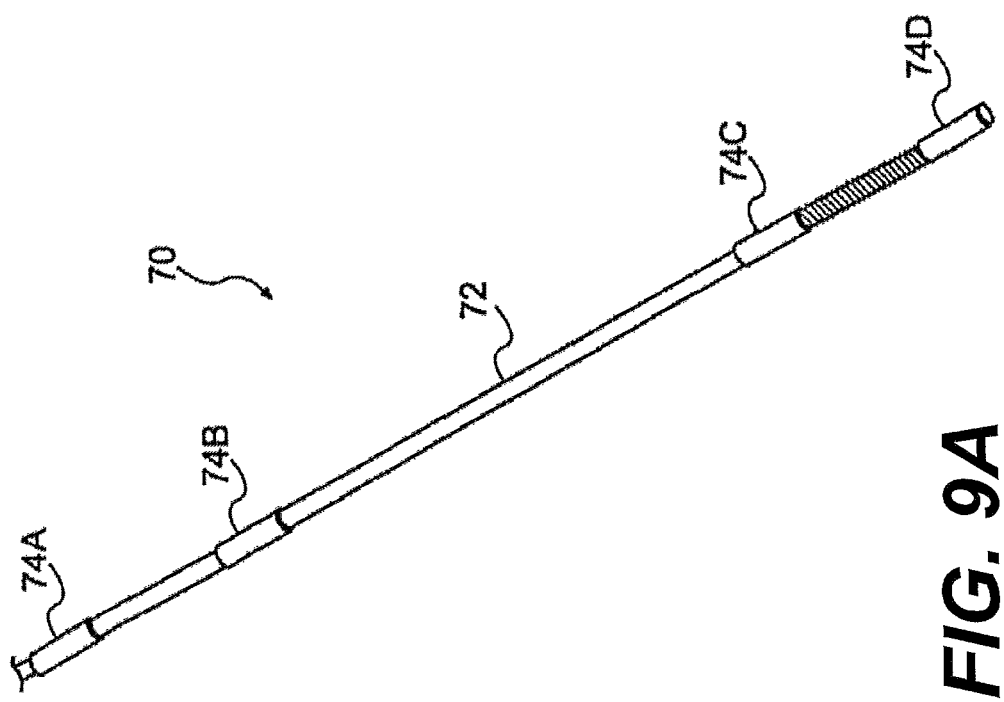

With reference to FIGS. 9A and 9B, a distal portion of the respiration sensing lead 70 and a distal detail of the sensing lead 70, respectively, are shown schematically. In the illustrated embodiment, the respiration sensing lead 70 and associated sensors 74 are implanted as shown in FIG. 2. However, the respiration sensor(s) may comprise a variety of different design embodiments, both implanted and external, and may be positioned at different anatomical sites. Generally, the respiratory sensor(s) may be internal/implanted or external, and may be connected to the neurostimulator via a wired or wireless link. The respiratory sensor(s) may detect respiration directly or a surrogate thereof. The respiratory sensor(s) may measure, for example, respiratory airflow, respiratory effort (e.g., diaphragmatic or thoracic movement), intra-pleural pressure, lung impedance, respiratory drive, upper airway EMG, changes in tissue impedance in and around the lung(s) including the lungs, diaphragm and/or liver, acoustic airflow or any of a number other parameters indicative of respiration. Detailed examples of suitable respiration sensing leads and sensors will be described in more detail hereinafter.

With continued reference to FIGS. 9A and 9B, the respiration sensing lead 70 includes a lead body 72 and a plurality of respiration sensors 74A-74D comprising ring electrodes for sensing bio-impedance. The lead body 72 of the respiration sensing lead 70 may include a jacket cover comprising an extruded silicone tube optionally including a polyurethane cover (80 A durometer), or may comprise an extruded polyurethane tube (55 D durometer). The ring electrodes 74A-74D may comprise 90/10 or 80/20 platinum iridium alloy tubes having an outside diameter of 0.050 inches and a length of 5 mm, and secured to the jacket cover by laser welding and/or adhesive bonding, for example. The lead body 72 may include a plurality of conductors 78 as seen in the transparent window in the jacket cover, which is shown for purposes of illustration only. The conductors 78 may comprise insulated and coiled BSW or solid wire (optionally DFT silver core wire) disposed in the tubular jacket, with one conductor provided for each ring electrode 74A-74D requiring independent control. Generally, the impedance electrodes 74A-74D may comprise current emitting electrodes and voltage sensing electrodes for detecting respiration by changes in bio-impedance. The number, spacing, anatomical location and function of the impedance electrodes will be described in more detail hereinafter.

Description of Implant Procedure

Figure 10:
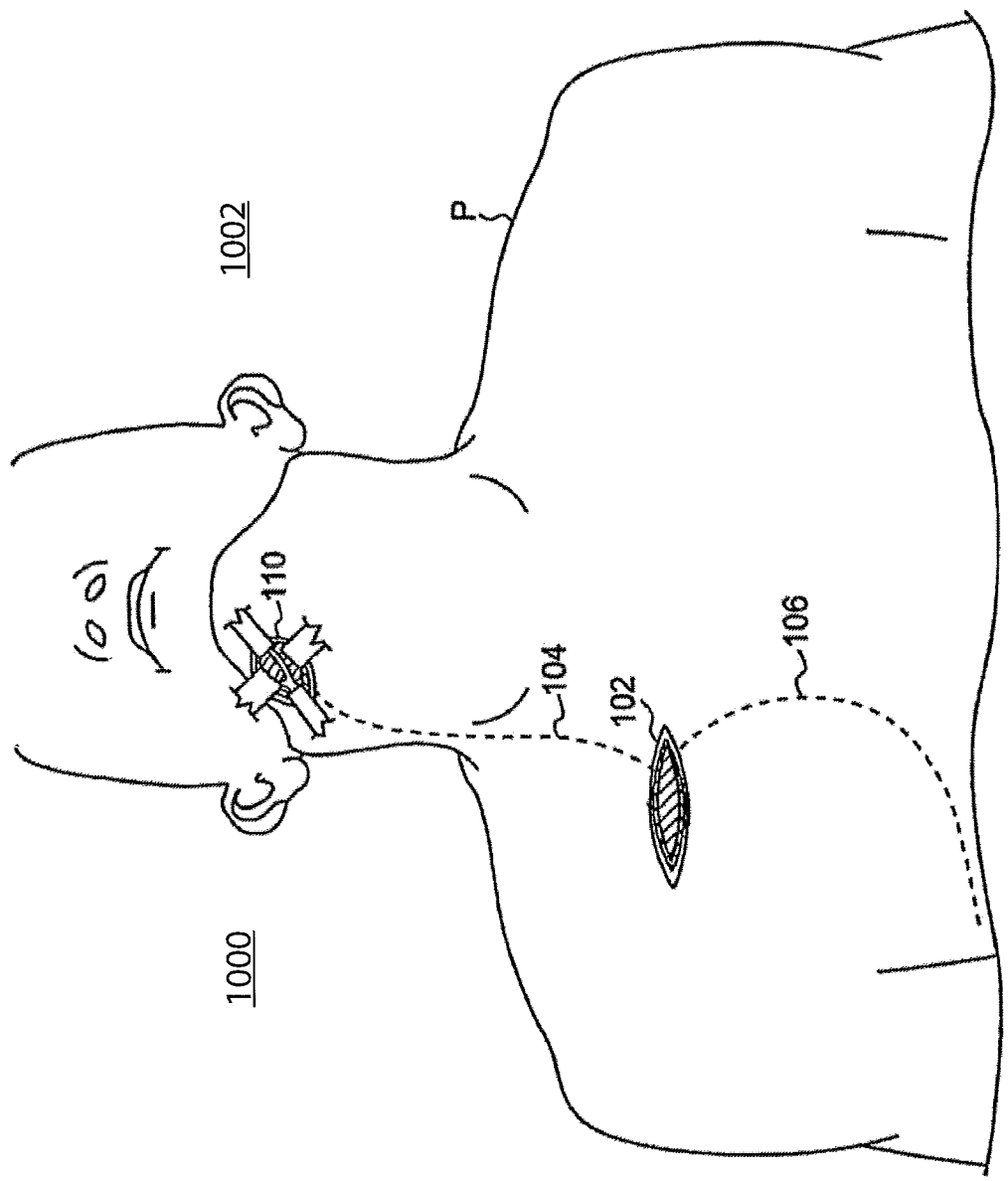
FIG. 10 schematically illustrates surgical access and tunneling sites for implanting the system illustrated in FIG. 2.

With reference to FIG. 10, surgical access sites are schematically shown for implanting the internal neurostimulator components 20 shown in FIG. 1. The internal neurostimulator components 20 may be surgically implanted in a patient on the right side 1000 or left side 1002 (FIG. 10). The right side may be preferred because it leaves the left side available for implantation of a pacemaker, defibrillator, etc., which are traditionally implanted on the left side. The right side may also be preferred because it lends itself to a clean respiratory signal less susceptible to cardiac artifact and also offers placement of respiratory sensors across the interface between the lung, diaphragm and liver for better detection of impedance changes during respiration.

With continued reference to FIG. 10, the INS (not shown) may be implanted in a subcutaneous pocket 102 in the pectoral region, for example. The stimulation lead (not shown) may be implanted in a subcutaneous tunnel 104 along (e.g., over or under) the platysma muscle in the neck region. The respiration sensing lead (not shown) may be implanted in a subcutaneous tunnel 106 extending adjacent the ribcage to an area adjacent lung tissue and/or intercostal muscles outside the pleural space. The nerve cuff electrode (not shown) may be attached to a nerve by surgical dissection at a surgical access site 110 proximate the targeted stimulation site. In the illustrated example, the target nerve is the right hypoglossal nerve and the surgical access site is in the submandibular region.

Figure 11A:
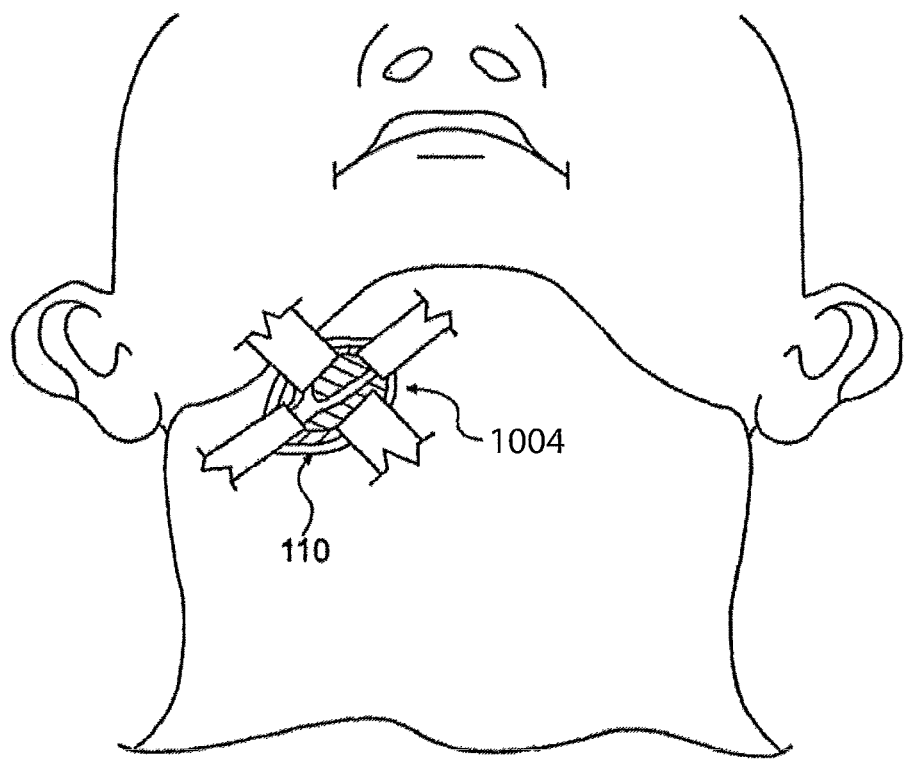
FIGS. 11A and 11B schematically illustrate dissection to a hypoglossal nerve.
Figure 11B:
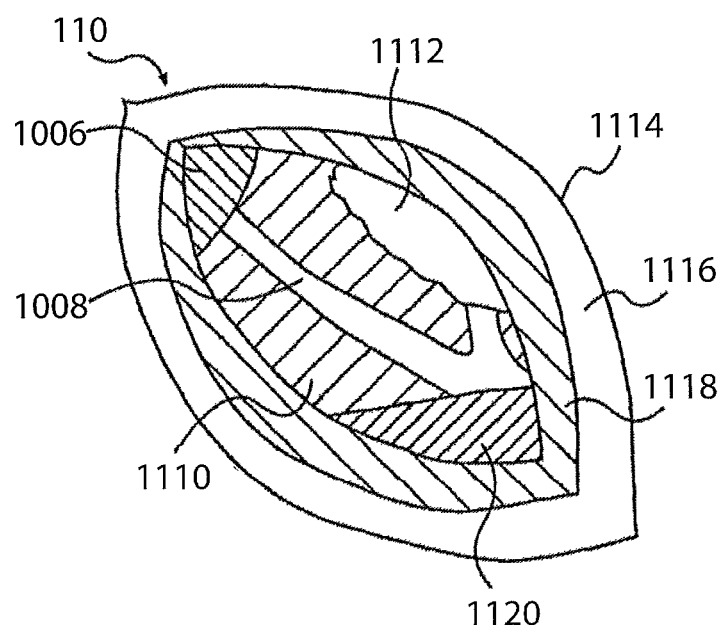
Figure 12:
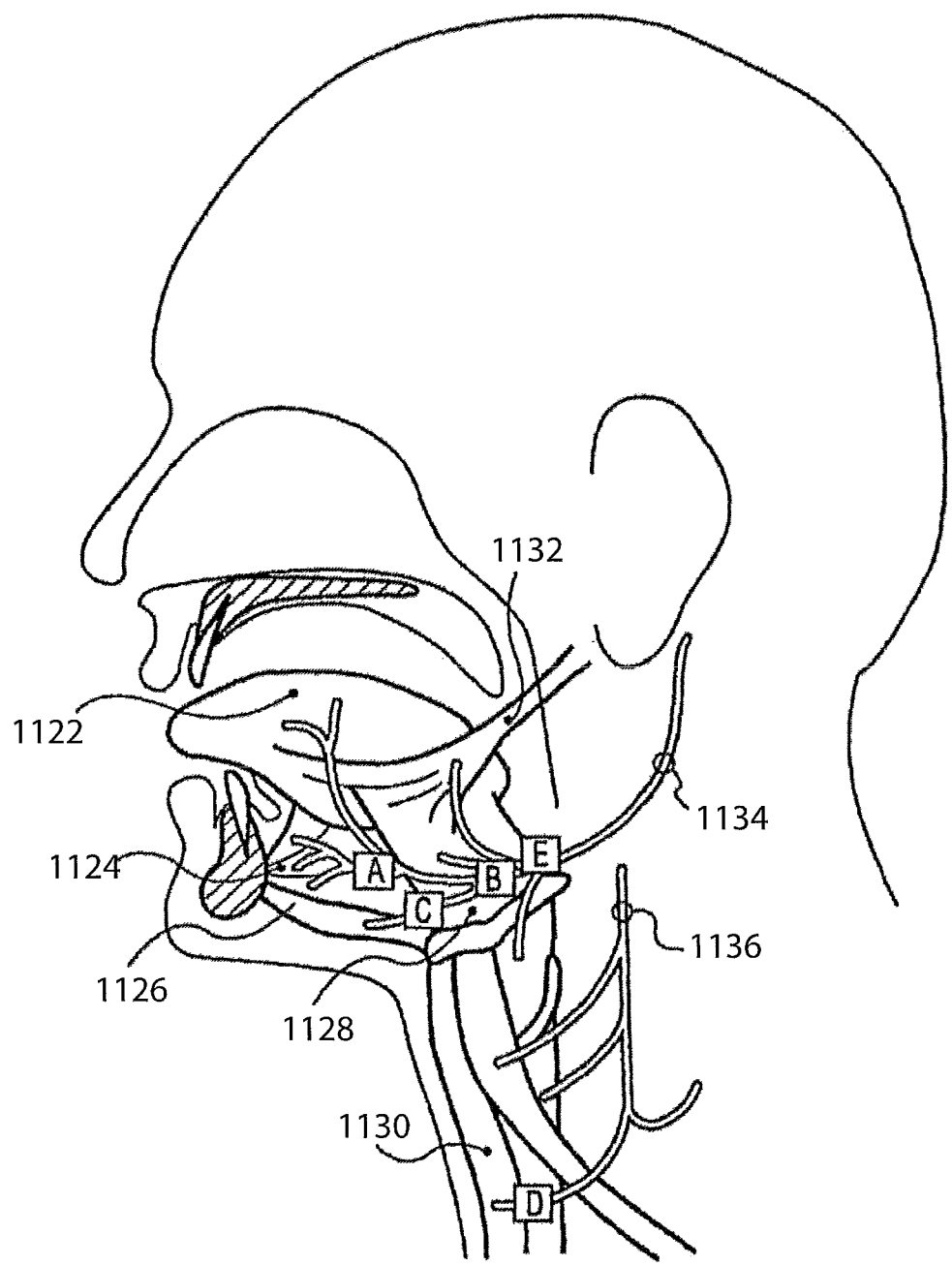
FIG. 12 schematically illustrates various possible nerve stimulation sites for activating muscles controlling the upper airway.

With reference to FIGS. 11A and 11B, a surgical dissection 1004 to the hypoglossal nerve is shown schematically, viewed through an opening 110. A unilateral dissection is shown, but a bilateral approach for bilateral stimulation may also be employed. Conventional surgical dissection techniques may be employed. Aspects of patient anatomy are depicted in FIGS. 11A, 11B, and 12, including the mylohyoid muscle 1006 (refracted), hyoglossus muscle 1110/1128, submandibular gland 1112, epidermis 1114, dermis and subcutaneous tissues 1116, platysma muscle 1118, digastric muscle 1120, genihyoid muscle 1126, sternohyoid muscle 1130, hypoglossal nerve (XII) 1134, and superior root of ansa cervicalis 1136.

The branch of the hypoglossal nerve 1008 (usually a medial or distal branch) leading to the genioglossus muscle 1124 may be identified by stimulating the hypoglossal nerve at different locations and observing the tongue 1122 for protrusion. Because elongation and/or flexion may be mistaken for protrusion, it may be desirable to observe the upper airway using a flexible fiber optic scope (e.g., nasopharyngoscope) inserted into the patient's nose, through the nasal passages, past the nasopharynx and velopharynx to view of the oropharynx and hypopharynx and visually confirm an increase in airway caliber by anterior displacement (protrusion) of the tongue base when the nerve branch 1008 is stimulated.

The implant procedure may be performed with the patient under general anesthesia in a hospital setting on an outpatient basis. Alternatively, local anesthesia (at the surgical access sites and along the subcutaneous tunnels) may be used together with a sedative in a surgical center or physician office setting. As a further alternative, a facial nerve block may be employed. After a post-surgical healing period of about several weeks, the patient may return for a polysomnographic (PSG) test or sleep study at a sleep center for programming the system and titrating the therapy. A trialing period may be employed prior to full implantation wherein the hypoglossal nerve or the genioglossus muscle is stimulated with fine wire electrodes in a sleep study and the efficacy of delivering stimulus to the hypoglossal nerve or directly to the genioglossus muscle is observed and measured by reduction in apnea hypopnea index, for example.

Other nerve target sites are described elsewhere herein and may be accessed by similar surgical access techniques. As an alternative to surgical dissection, less invasive approaches such as percutaneous or laparoscopic access techniques may be utilized, making use of associated tools such as tubular sheaths, trocars, etc.

Description of Alternative Stimulation Target Sites

With reference to FIG. 12, various possible nerve and/or direct muscle stimulation sites are shown for stimulating muscles controlling patency of the upper airway. In addition to the upper airway which generally includes the pharyngeal space, other nerves and dilator muscles of the nasal passage and nasopharyngeal space may be selectively targeted for stimulation. A general description of the muscles and nerves suitable for stimulation follows, of which the pharyngeal nerves and muscles are shown in detail in FIG. 12.

Airway dilator muscles and associated nerves suitable for activation are described in the following text and associated drawings. The dilator naris muscle functions to widen the anterior nasal aperture (i.e., flares nostrils) and is innervated by the buccal branch of the facial nerve (cranial nerve VII). The tensor veli palatine muscle functions to stiffen the soft palate and is innervated by the medial (or internal) pterygoid branch of the mandibular nerve. The genioglossus muscle is an extrinsic pharyngeal muscle connecting the base of the tongue to the chin and functions to protrude the tongue. The genioglossus muscle is typically innervated by a distal or medial branch (or branches) of the right and left hypoglossal nerve. The geniohyoid muscle connects the hyoid bone to the chin and the sternohyoid muscle attaches the hyoid bone to the sternum. The geniohyoid muscle functions to pull the hyoid bone anterosuperiorly, the sternohyoid muscle functions to pull hyoid bone inferiorly, and collectively (i.e., co-activation) they function to pull the hyoid bone anteriorly. The geniohyoid muscle is innervated by the hypoglossal nerve, and the sternohyoid muscle is innervated by the ansa cervicalis nerve.

By way of example, a nerve electrode may be attached to a specific branch of the hypoglossal nerve innervating the genioglossus muscle (tongue protruder), or may be attached to a more proximal portion (e.g., trunk) of the hypoglossal nerve in which a specific fascicle innervating the genioglossus muscle is targeted by steering the stimulus using an electrode array. Activating the genioglossus muscle causes the tongue to protrude thus increasing the size of anterior aspect of the upper airway or otherwise resisting collapse during inspiration.

As an alternative to activation of any or a combination of the airway dilator muscles, co-activation of airway dilator and airway restrictor or retruder muscles may be used to stiffen the airway and maintain patency. By way of example, a nerve electrode may be attached to specific branches of the hypoglossal nerve innervating the genioglossus muscle (tongue protruder), in addition to the hyoglossus and styloglossus muscles (tongue retruders), or may be attached to a more proximal portion (e.g., trunk) of the hypoglossal nerve in which specific fascicles innervating the genioglossus, hyoglossus and styloglossus muscles are targeted by steering the stimulus using an electrode array. Activating the hyoglossus and styloglossus muscles causes the tongue to retract, and when co-activated with the genioglossus, causes the tongue to stiffen thus supporting the anterior aspect of the upper airway and resisting collapse during inspiration. Because the tongue retruder muscles may overbear the tongue protruder muscle under equal co-activation, unbalanced co-activation may be desired. Thus, a greater stimulus (e.g., longer stimulation period, larger stimulation amplitude, higher stimulation frequency, etc.) or an earlier initiated stimulus may be delivered to the portion(s) of the hypoglossal nerve innervating the genioglossus muscle than to the portion(s) of the hypoglossal nerve innervating the hyoglossus and styloglossus muscles.

With continued reference to FIG. 12, examples of suitable nerve stimulation sites include B; A+C; A+C+D; B+D; C+D; and E. Sites B and E may benefit from selective activation by field steering using an electrode array. As mentioned before, nerve electrodes may be placed at these target nerve(s) and/or intramuscular electrodes may be placed directly in the muscle(s) innervated by the target nerve(s).

Site A is a distal or medial branch of the hypoglossal nerve proximal of a branch innervating the genioglossus muscle and distal of a branch innervating the geniohyoid muscle. Site B is a more proximal portion of the hypoglossal nerve proximal of the branches innervating the genioglossus muscle and the geniohyoid muscle, and distal of the branches innervating the hyoglossus muscle and the styloglossus muscle. Site C is a medial branch of the hypoglossal nerve proximal of a branch innervating the geniohyoid muscle and distal of branches innervating the hyoglossus muscle and the styloglossus muscle. Site D is a branch of the ansa cervicalis nerve distal of the nerve root and innervating the sternohyoid. Site E is a very proximal portion (trunk) of the hypoglossal nerve proximal of the branches innervating the genioglossus, hyoglossus and styloglossus muscles.

Activating site B involves implanting an electrode on a hypoglossal nerve proximal of the branches innervating the genioglossus muscle and the geniohyoid muscle, and distal of the branches innervating the hyoglossus muscle and the styloglossus muscle.

Co-activating sites A+C involves implanting a first electrode on a hypoglossal nerve proximal of a branch innervating the genioglossus muscle and distal of a branch innervating the geniohyoid muscle; and implanting a second electrode on the hypoglossal nerve proximal of a branch innervating the geniohyoid muscle and distal of branches innervating the hyoglossus muscle and the styloglossus muscle.

Co-activating sites A+C+D involves implanting a first electrode on a hypoglossal nerve proximal of a branch innervating the genioglossus muscle and distal of a branch innervating the geniohyoid muscle; implanting a second electrode on the hypoglossal nerve proximal of a branch innervating the geniohyoid muscle and distal of branches innervating the hyoglossus muscle and the styloglossus muscle; and implanting a third electrode on a branch of an ansa cervicalis nerve distal of the nerve root and innervating the sternohyoid.

Co-activating sites B+D involves implanting a first electrode on a hypoglossal nerve proximal of branches innervating the genioglossus muscle and the geniohyoid muscle, and distal of branches innervating the hyoglossus muscle and the styloglossus muscle; and implanting a second electrode on a branch of an ansa cervicalis nerve distal of the nerve root and innervating the sternohyoid.

Co-activating sites C+D involves implanting a first electrode on a hypoglossal nerve proximal of a branch innervating the geniohyoid muscle, and distal of branches innervating the hyoglossus muscle and the styloglossus muscle and implanting a second electrode on a branch of an ansa cervicalis nerve distal of the nerve root and innervating the sternohyoid. Activating site E involves implanting an electrode on a hypoglossal nerve proximal of the branches innervating the genioglossus, hyoglossus and styloglossus muscles; and selectively activating (e.g., by field steering) the genioglossus muscle before or more than the hyoglossus and styloglossus muscles.

Description of Field Steering Alternatives

Figure 13A:
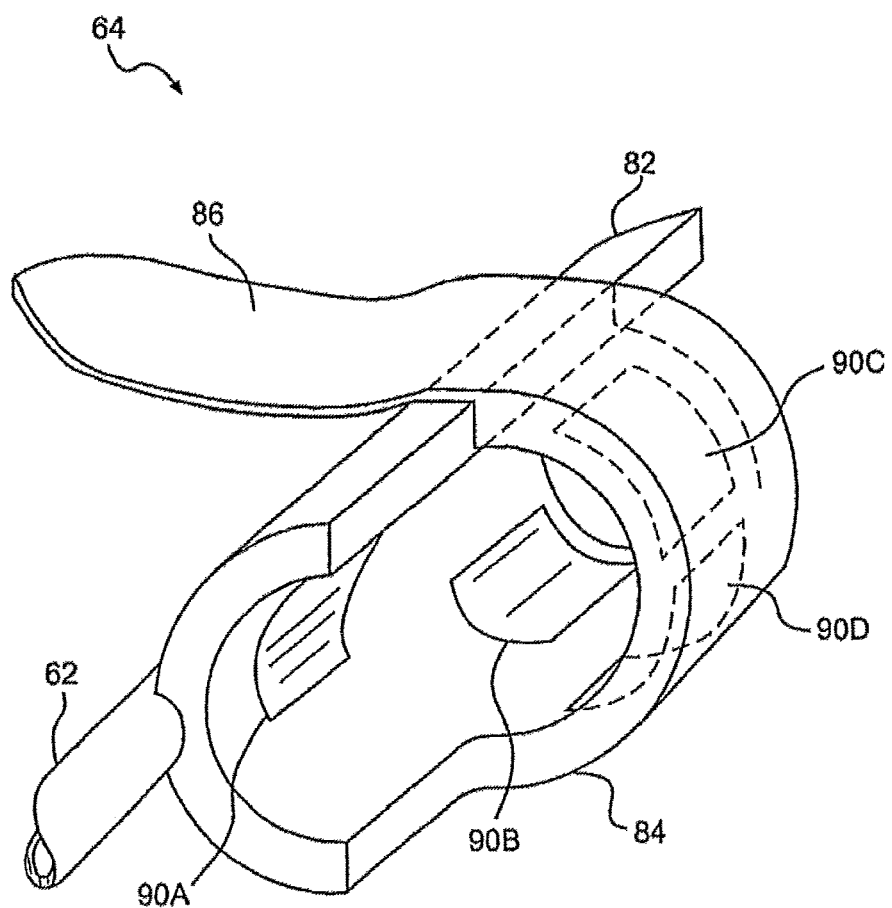
FIGS. 13A-13H schematically illustrate field steering embodiments.

With reference to FIGS. 13A-13G, a field steering nerve cuff electrode 64 is shown schematically. As seen in FIG. 13A, the nerve cuff electrode 64 may include four electrode contacts 90A-90D to enable field steering, and various arrangements of the electrode contacts 90A-90D are shown in FIGS. 13B-13G. Each of FIGS. 13B-13G includes a top view of the cuff 64 to schematically illustrate the electrical field (activating function) and an end view of the cuff 64 to schematically illustrate the area of the nerve effectively stimulated. With this approach, electrical field steering may be used to stimulate a select area or fascicle(s) within a nerve or nerve bundle to activate select muscle groups as described herein.

With specific reference to FIG. 13A, the nerve cuff electrode 64 may comprise a cuff body having a lateral (or superficial) side 82 and a medial (or contralateral, or deep) side 84. The medial side 84 is narrower or shorter in length than the lateral side 82 to facilitate insertion of the medial side 84 around a nerve such that the medial side is on the deep side of the nerve and the lateral side is on the superficial side of the nerve. An integral tow strap 86 may be used to facilitate wrapping the cuff around a nerve. The nerve cuff electrode 64 includes electrode contacts 90A, 90B, 90C and 90D imbedded in the body of the cuff, with their inside surface facing exposed to establish electrical contact with a nerve disposed therein. Electrode contacts 90A and 90B are longitudinally and radially spaced from each other. Electrode contacts 90C and 90D are radially spaced from each other and positioned longitudinally between electrode contacts 90A and 90B. Each of the four electrode contacts may be operated independently via four separate conductors (four filar) in the lead body 62.

With specific reference to FIGS. 13B-13G, each includes a top view (left side) to schematically illustrate the electrical field or activating function (labeled E), and an end view (right side) to schematically illustrate the area of the nerve effectively stimulated (labeled S) and the area of the nerve effectively not stimulated (labeled NS). Electrodes 90A-90D are labeled A-D for sake of simplicity only. The polarity of the electrodes is also indicated, with each of the cathodes designated with a negative sign (−) and each of the anodes designated with a positive sign (+).

Figure 13B:
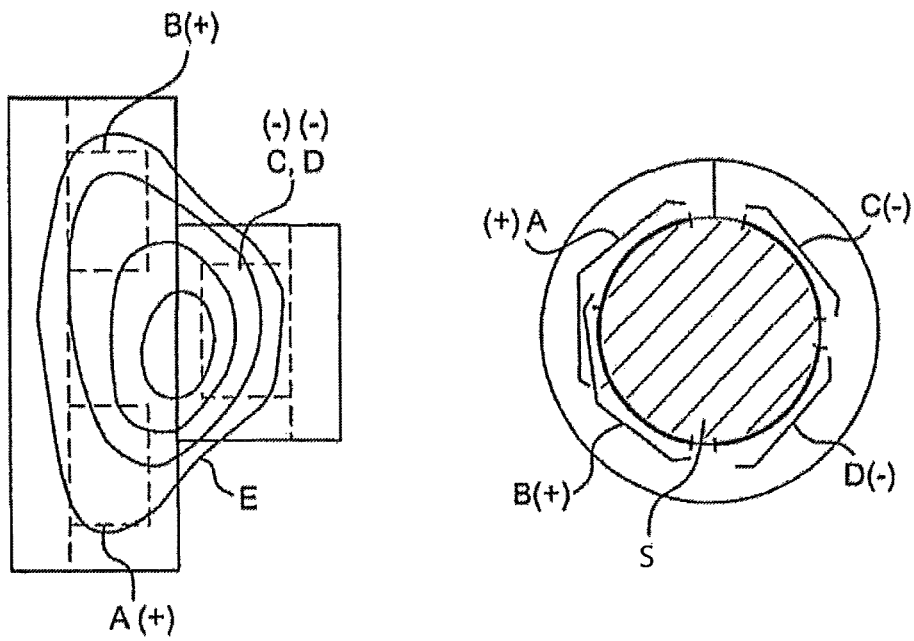

With reference to FIG. 13B, a tripolar transverse guarded cathode arrangement is shown with electrodes C and D comprising cathodes and electrodes A and B comprising anodes, thus stimulating the entire cross-section of the nerve.

Figure 13C:
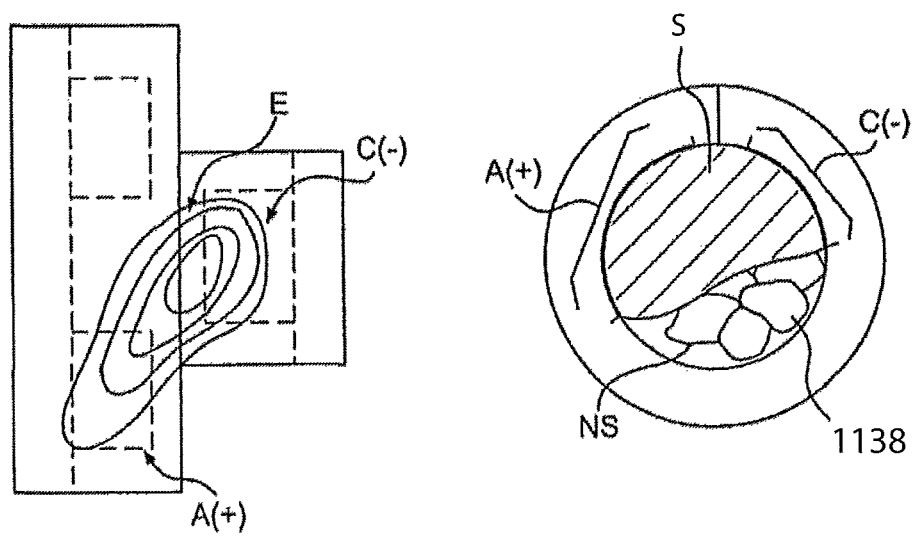

With reference to FIG. 13C, a bipolar diagonal arrangement is shown with electrode C comprising a cathode and electrode A comprising an anode, wherein the fascicles that are stimulated may comprise superior fascicles of the hypoglossal nerve, and the fascicles that are not stimulated may comprise inferior fascicles of the hypoglossal nerve (e.g., fascicles that innervate the intrinsic muscles of the tongue).

Figure 13D:
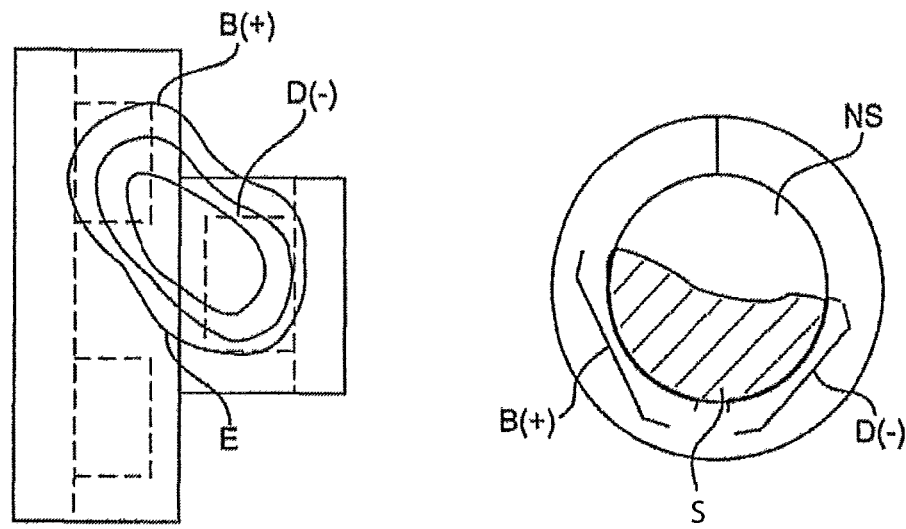

With reference to FIG. 13D, another bipolar diagonal arrangement is shown with electrode D comprising a cathode and electrode B comprising an anode, wherein the fascicles that are stimulated may comprise inferior fascicles of the hypoglossal nerve.

Figure 13E:
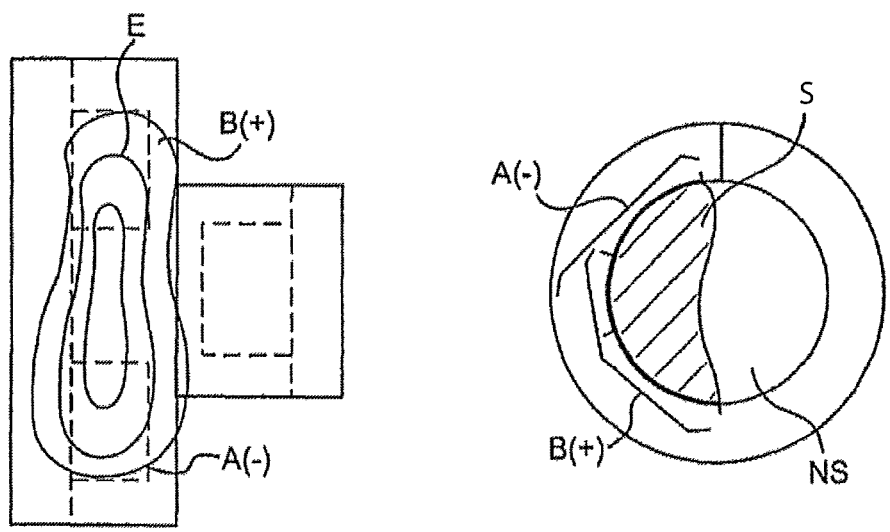

With reference to FIG. 13E, a bipolar axial arrangement is shown with electrode A comprising a cathode and electrode B comprising an anode, wherein the fascicles that are stimulated may comprise lateral fascicles of the hypoglossal nerve.

Figure 13F:
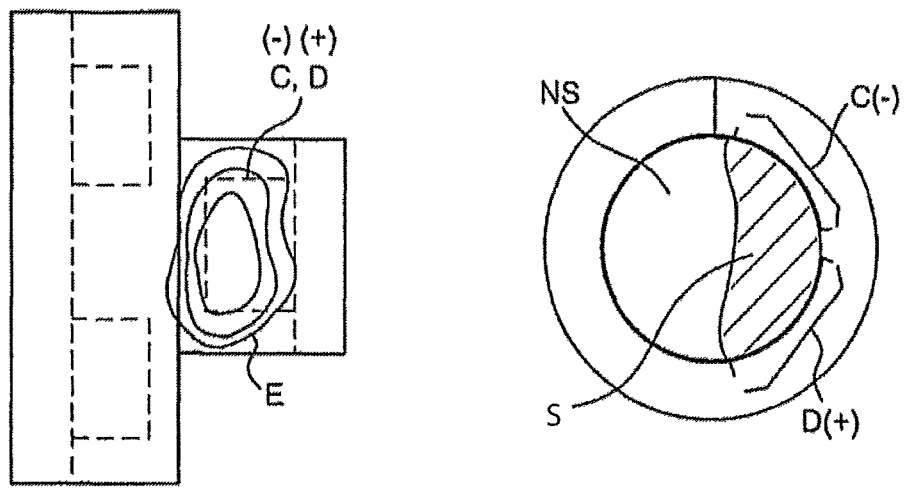

With reference to FIG. 13F, a bipolar transverse arrangement is shown with electrode C comprising a cathode and electrode D comprising an anode, wherein the fascicles that are stimulated may comprise medial fascicles of the hypoglossal nerve.

Figure 13G:
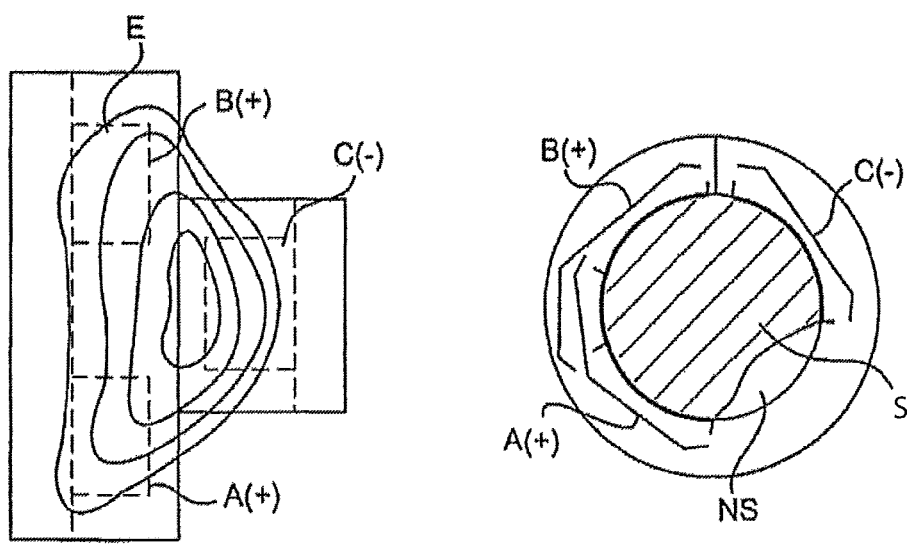

With reference to FIG. 13G, a modified tripolar transverse guarded cathode arrangement is shown with electrode C comprising a cathode and electrodes A and B comprising anodes, thus stimulating the entire cross-section of the nerve with the exception of the inferior medial fascicles.

Nerves like the hypoglossal nerve or superior laryngeal nerve typically include a plurality of fibers having relatively larger diameters and a plurality of fibers having relatively smaller diameters. In the case of single function nerves, such as, for example, the hypoglossal nerve HGN, all of the nerve fibers may either be sensory or motor in function. However, in the case of multi-function nerves, such as, for example, the superior laryngeal nerve SLN, the fibers having relatively larger diameters are typically motor (efferent) fibers, and the fibers having relatively smaller diameters are typically sensory (afferent) fibers. Accordingly, there may be a need to selectively stimulate the differing diameter fibers in a nerve.

Figure 13H:
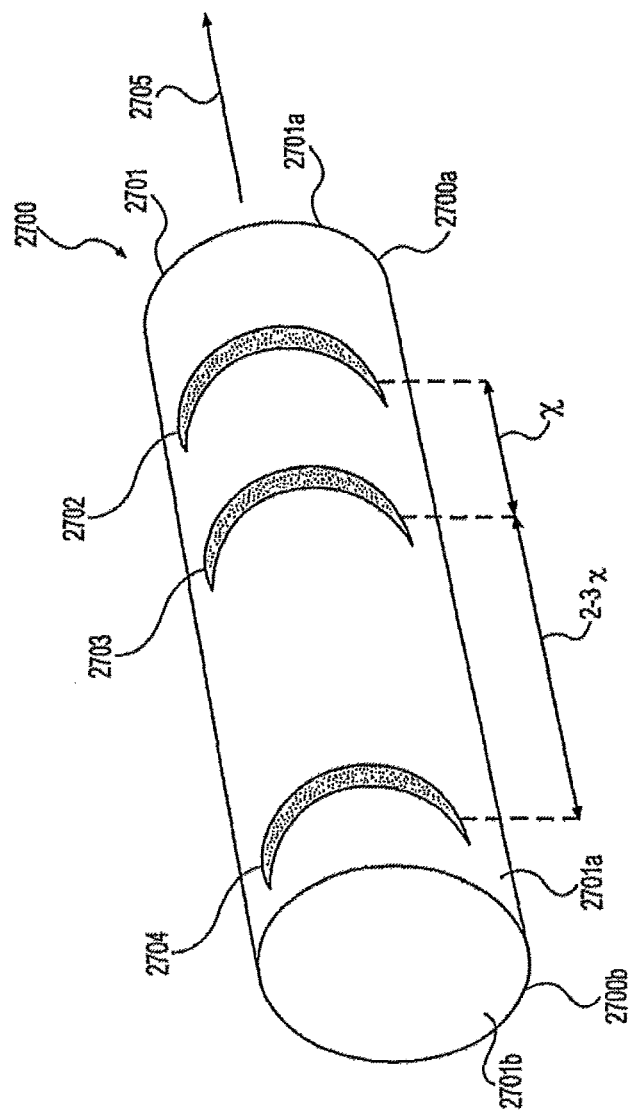

Turning now to FIG. 13H, there is depicted an embodiment of a uni-directional stimulation electrode 2700 having a distal end 2700a and a proximal end 2700b. Electrode 2700 may include a substantially cylindrical nerve cuff 2701 in accordance with the principles of the present disclosure. As illustrated, nerve cuff 2701 may include an outer surface 2701a and an inner surface 2701b. Electrode 2700 may further include a plurality of electrode contacts 2702-2704. Electrode contacts 2702-2704 may be used as any suitable electrode contact known to those of ordinary skill in the art. For example, electrode contact 2702 may be used as an anode, electrode contact 2703 may be used as a cathode, and electrode contact 2704 may be used as a second anode. Electrode contacts 2702-2704 may also include any suitable shape and/or configuration known in the art. For example, electrode contacts 2702-2704 may include a substantially semi-circular configuration.

Electrode contacts 2702-2704 may be disposed on nerve cuff 2701 in any suitable configuration to achieve the desired effect. For example, electrode contacts 2702-2704 may be disposed on inner surface 2701b. As depicted in FIG. 13H, cathode electrode contact 2703 may be disposed approximately equidistant from distal end 2700a and proximal end 2700b, and anode electrode contacts 2702 may be differentially spaced around cathode electrode contact 2703, so as to control the direction of stimulation of electrode 2700. For example, anode electrode contact 2702 may be spaced from cathode electrode contact 2703 by any suitable distance $\chi$ while second anode electrode contact 2704 may be spaced from cathode electrode contact 2703 by a distance that is approximately two or three times greater than distance $\chi$. In this exemplary configuration, the direction of stimulation may be in the direction of arrow 2705.

In use, electrode 2700 may be implanted upon a nerve in accordance with the principles of this disclosure. Electrode 2700 may be oriented on the nerve it is implanted on in any suitable manner, such as, for example, according to the direction of intended stimulation. Thus, in circumstances where it may be desired to stimulate efferent (motor) fibers of a nerve, such as, for example, the superior laryngeal nerve SLN, while avoiding stimulation to afferent (sensory) fibers of the nerve, the electrode 2700 may be oriented on the nerve in a manner such that anode electrode contact 2702 is located distally of cathode electrode contact 2703, with distal and proximal designations based on the relative location of the electrode contact on the nerve. Alternatively, in circumstances where it may be desired to stimulate afferent fibers of a nerve while avoiding stimulation of efferent fibers of the nerve, the electrode 2700 may be oriented on the nerve in a manner such that anode electrode contact 2702 is located proximally of cathode electrode contact 2703.

Figure 13I:
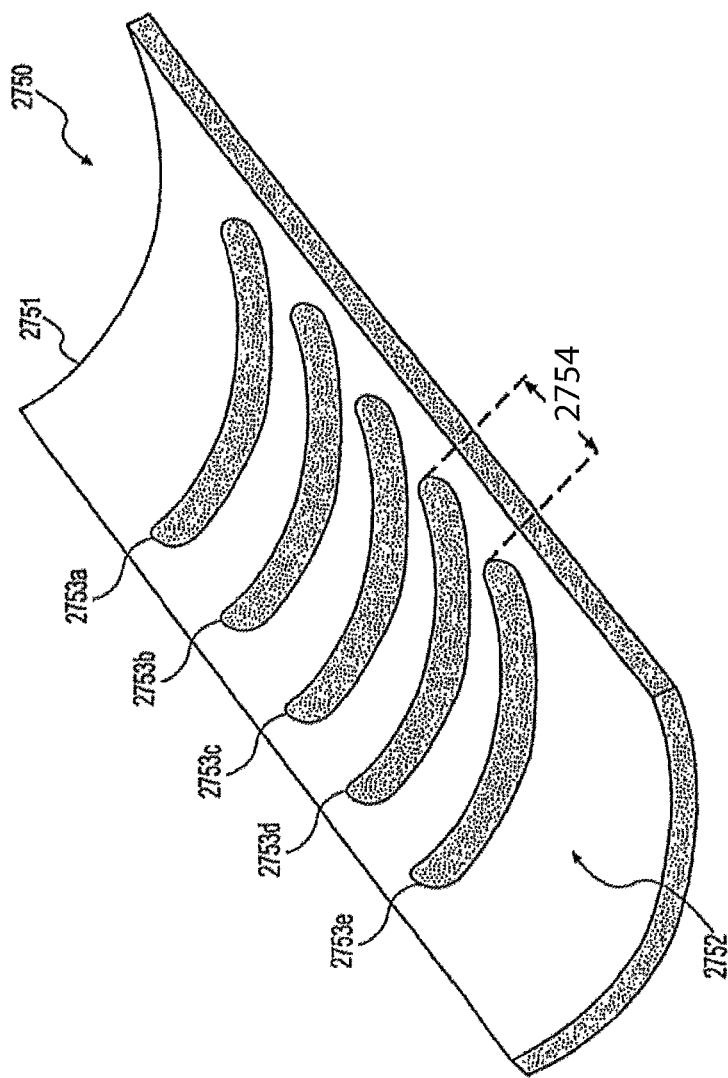
FIGS. 13I-13Q schematically illustrate alternative embodiments of nerve cuff electrodes with selective fiber stimulation mechanisms.

With reference now to FIG. 13I, there is depicted an embodiment of a stimulation electrode 2750 for, among other things, selectively stimulating differing diameter fibers of a nerve, such as, for example, the hypoglossal nerve or superior laryngeal nerve. Electrode 2750 may include a body 2751, and may include any suitable configuration in accordance with the principles of the present disclosure. Additionally, electrode 2750 may include an array 2752 of suitable electrode contacts known to those skilled in the art. Although the depicted embodiment of electrode 2750 includes five electrode contacts 2753a-2753e, array 2752 may include a greater or lesser number of electrode contacts. Electrode contacts 2753a-2753e may be disposed on body 2751 in any suitable configuration to produce the desired effect. For example, as depicted in FIG. 13I, electrode contacts 2753a-2753e may be disposed serially, with approximately a one (1) millimeter spacing 2754 in between each electrode contact 2753a-2753e. Electrode contacts 2753a-2753e may be configured to function as either anode electrode contacts or cathode electrode contacts, as desired.

Electrode contacts 2753 may be connected to an implanted neurostimulator (INS), such as, for example, INS 50, in accordance with the present disclosure. The INS may be programmed to select any of electrode contacts 2753a-2753e for nerve stimulation. For example, in circumstances where it may be desired to stimulate the smaller diameter fibers of a nerve, it is contemplated that all electrode contacts 2753a-2753e may be selected for nerve stimulation, since closely spaced electrode contacts typically affect smaller diameter fibers (e.g., afferent or sensory fibers). In these circumstances, electrode contacts 2753a, 2753c, and 2753e may function as anode electrode contacts and electrode contacts 2753b and 2753d may function as cathode electrode contacts. In circumstances where it may be desired to stimulate the larger diameter fibers of a nerve, it is contemplated that only electrode contacts 2753a, 2753c, and 2753e may be selected for nerve stimulation, since loosely spaced electrode contacts typically affect larger diameter fibers (e.g., efferent or motor fibers). In these circumstances, electrode contacts 2753a and 2753e may function as anode electrode contacts, and 2753c may function as a cathode electrode contact.

Alternatively, electrode 2750 may be utilized to reduce muscle fatigue when implanted on single function nerves, such as, for example, the hypoglossal nerve. In such circumstances, muscle fatigue may be reduced by alternatively switching between using loosely spaced electrode contacts 2753a, 2753c, and 2753e, to stimulate large diameter fibers, and closely spaced electrode contacts 2753a-2753e, to stimulate small diameter fibers.

Figure 13K:
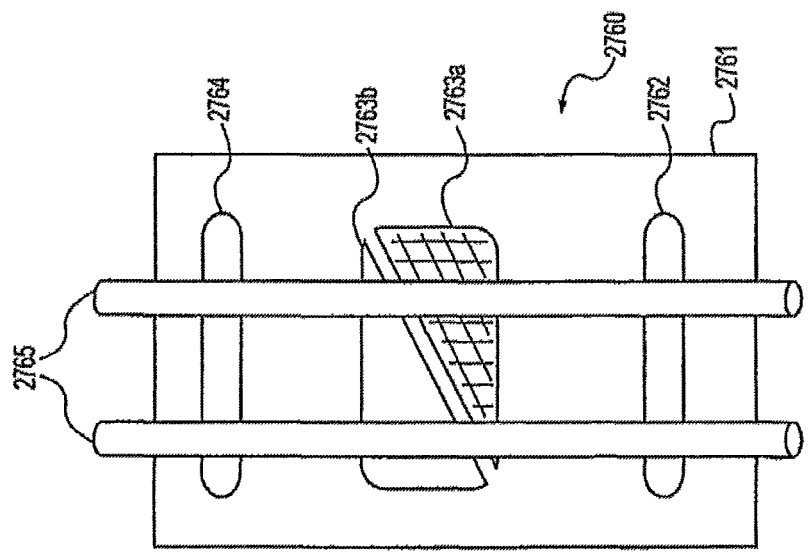
Figure 13J:
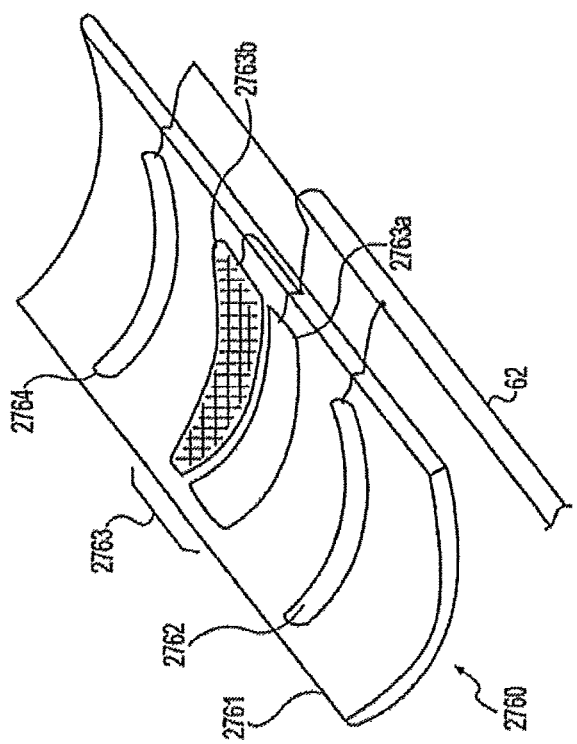

Turning to FIGS. 13J-13K, in accordance with the present disclosure, there is depicted another embodiment of a nerve cuff electrode 2760 for facilitating reduction in muscle fatigue. Nerve cuff electrode 2760 may include a body 2761 having a plurality of electrode contacts 2762, 2763, and 2764 electrically coupled with conductors 2765 in a manner similar to the connection provided by common conductor 68A or independent conductor 68B described above. Electrode contacts 2762-2764 may include any suitable electrode contacts in accordance with the present disclosure. Although the depicted embodiment of nerve cuff electrode 2760 includes three electrode contacts 2762-2764, nerve cuff electrode 2760 may include a greater or lesser number of electrode contacts. Furthermore, electrode contacts may be disposed on body 2761 in any suitable configuration to achieve the desired effect, such as, for example, serially, as depicted. In the depicted embodiment, electrode contacts 2762 and 2764 may function as anode electrode contacts, while electrode contact 2763 may function as a cathode electrode contact. Electrode contact 2763 may include two distinct, substantially triangularly shaped portions 2763a and 2763b. However, portions 2763a and 2763b may include any suitable shape. In addition, portions 2763a and 2763b may be configured to be of differing conductive properties, so that, for the same stimulation pulse (e.g., a slow rising, small amplitude pulse having a relatively long duration of approximately 0.2 to 0.35 milliseconds) applied to each of the portions 2763a and 2763b, the resultant charge densities at the surface of each of the portions 2763a and 2763b may be different. For example, portions 2763a and 2763b may be made of electrically differing materials. For discussion purposes only, it is assumed that portion 2763a is configured to deliver a charge density lower than that of portion 2763b. However, portion 2763a may be configured to deliver a charge density that is higher than the charge density of portion 2763b.

Since the small diameter fibers of a nerve are typically stimulated by low charge densities and large diameter fibers of the nerve are typically stimulated by high charge densities, portions 2763a and 2763b may be sequentially utilized to alternate between stimulating the small and large diameter fibers of a nerve. In other words, in use, a stimulation pulse may be first delivered to portion 2763a to stimulate the small diameter fibers of a nerve. A subsequent stimulation pulse may be then delivered to portion 2763b to stimulate the large diameter fibers of a nerve. It is contemplated that alternating between stimulating the small and large diameter fibers of a nerve may facilitate reducing muscle fatigue while also ensuring sufficient muscle mass is stimulated to maintain the necessary contraction and force generation to successfully treat OSA.

Figure 13L:
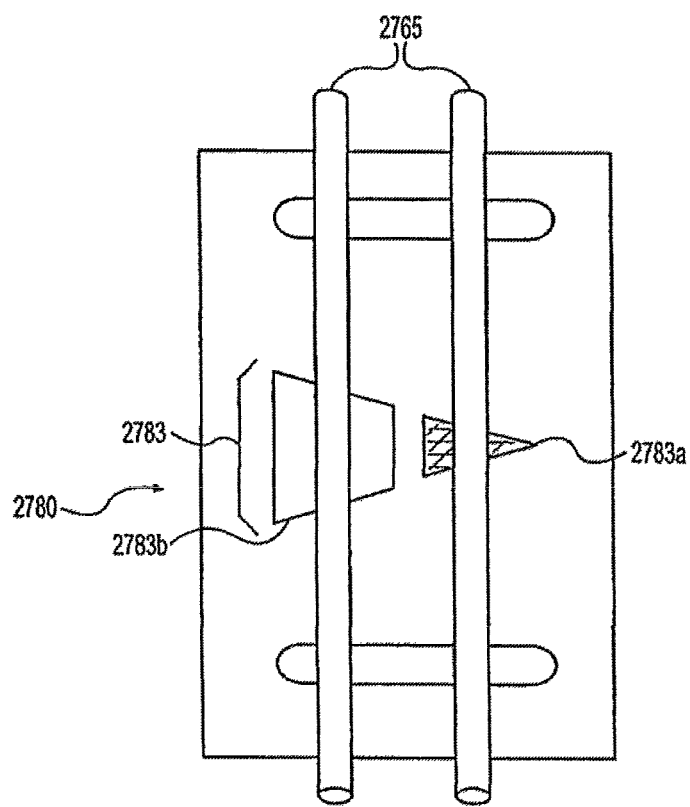

Turning now to FIG. 13L, there is illustrated yet another embodiment of a nerve cuff electrode 2780 for facilitating reduction in muscle fatigue. For the purposes of this disclosure, nerve cuff electrode 2780 may be substantially similar to nerve cuff electrode 2760. Nerve cuff electrode 2780, however, may differ from nerve cuff electrode 2760 in at least one way. For example, rather than having two substantially triangular portions, cathode electrode contact 2783 may comprise two substantially different portions 2783a and 2783b. Portions 2783a and 2783b may be spaced apart from one another and may include differing surface areas. For example, as illustrated, portion 2783a may include a smaller surface area than portion 2783b. Furthermore, portions 2783a and 2783b may include any suitable shape known in the art. Although portions 2783a and 2783b in the illustrated embodiment together define a substantially triangular shaped electrode contact 2783, portions 2783a and 2783b together may or may not define any suitable shape known in the art. Portions 2783a and 2783b, and the other electrodes illustrated in FIG. 13L, may be electrically coupled with conductors 2765 in a manner similar to the connection provided by common conductor 68A or independent conductor 68B described above Each of portions 2783a and 2783b may be configured to be substantially similar in conductance despite their differing surface areas. For example, portion 2783a may be made of a first material having a relatively lower conductance, while portion 2783b may be made of a second material having a relatively higher conductance. Thus, when subjected to the same stimulation pulse (e.g., a slow rising, small amplitude pulse having a relatively long duration of approximately 0.2 to 0.35 milliseconds), portion 2783a may have a higher charge density than portion 2783b because of its relatively smaller surface area than portion 2783b. Similarly, when subjected to the same stimulation pulse, portion 2783b may have a lower charge density than portion 2783a because of its relatively larger surface area than portion 2783a. Accordingly, because of the differing charge densities, portion 2783a may be adapted to stimulate large diameter fibers of a nerve, and portion 2783b may be adapted to stimulate small diameter fibers of the nerve.

In use, a stimulation pulse may be first delivered to portion 2783a to stimulate the large diameter fibers of a nerve. A subsequent stimulation pulse may be then delivered to portion 2783b to stimulate the small diameter fibers of the nerve. It is contemplated that alternating between stimulating the small and large diameter fibers of a nerve may facilitate muscle fatigue while also ensuring that sufficient muscle mass is stimulated to maintain the necessary contraction and force generation to successfully treat OSA.

In certain embodiments, such as when nerve cuff electrodes 2760 and 2780 are implanted on a multi-function nerve (e.g., the superior laryngeal nerve SLN), it is contemplated that portions 2763a/2763b and portions 2783a/2783b may be utilized to selectively stimulate either the afferent or efferent fibers of the nerve.

Figure 13M:
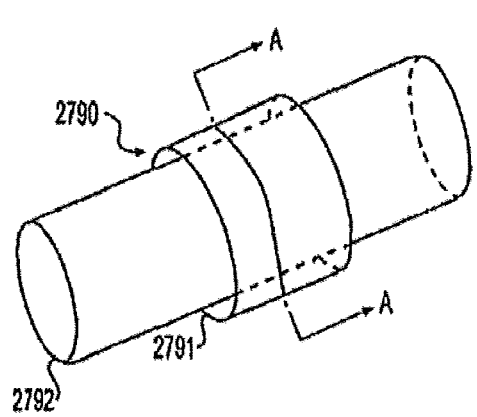
Figure 13N:
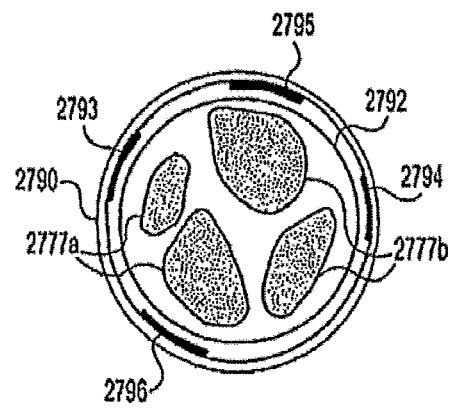
Figure 13O:
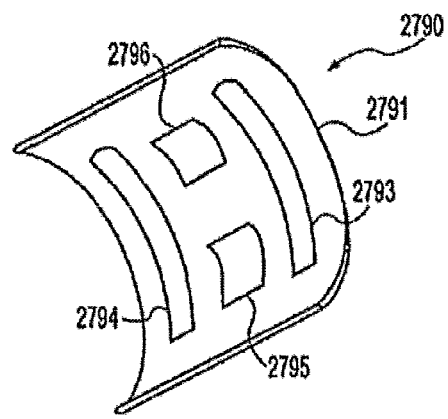
Figure 13P:
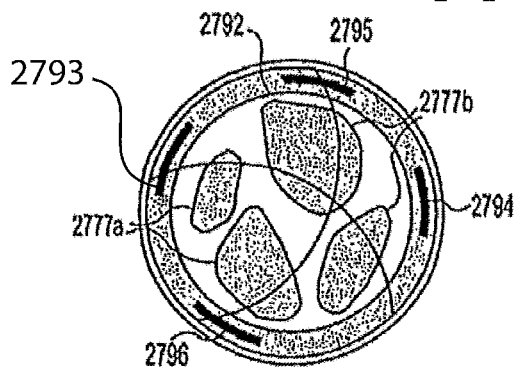
Figure 13Q:
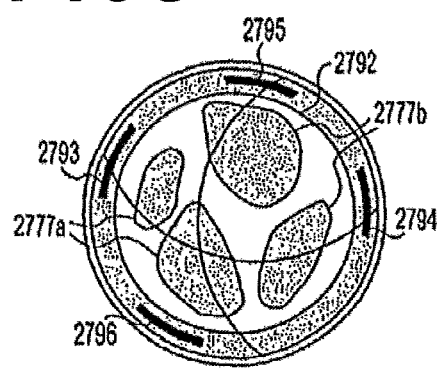

With reference now to FIGS. 13M-13Q, there is depicted yet another embodiment of a nerve cuff electrode 2790 for minimizing muscle fatigue. Nerve cuff electrode 2790 may include a cuff body 2791 for mounting about a nerve 2792 in accordance with the present disclosure. Cuff body 2791 may include a plurality of electrode contacts 2793-2796 also in accordance with the present disclosure. Although the depicted embodiment of nerve cuff electrode 2790 includes four electrode contacts 2793-2796, nerve cuff electrode 2790 may include a greater or lesser number of electrode contacts. The electrode contacts 2793-2796 may be distributed circumferentially about the inner surface of the cuff body 2791 so as to dispose each electrode contact 2793-2796 about the nerve 2792 as shown in the cross-sections provided in FIGS. 13N, 13P, and 13Q. The four electrode contacts 2793-2796, or a greater or lesser number of contacts, may be distributed equally about the inner circumference of the cuff body 2791 or distributed unequally as illustrated in FIGS. 13N, 13P, and 13Q. Referring to FIG. 13O, the electrode contacts 2793-2796 may also be distributed axially and circumferentially about the inner surface of the cuff body 2791 with an axial and/or a combined axial-circumferential spacing disposed between the electrodes to provide, for example, a plurality of axial distances between mating electrode contact 2793 and 2794, 2793 and 2795, 2793 and 2796, 2794 and 2795, 2794 and 2796, and 2795 and 2796. As can be appreciated, the cross-sectional views of FIGS. 13N, 13P, and 13Q may correspond to axially spaced electrode contacts such as those shown in FIG. 13O when the cross-section A-A illustrated in FIG. 13M is made to have a staggered or non-linear path through the nerve cuff electrode 2790.

Nerve cuff electrode 2790 may be configured to selectively stimulate both small diameter fibers contained in fascicle 2777a and large diameter fibers contained in fascicle 2777b of nerve 2792. For example, as shown in FIG. 13P, by applying an exemplary slow rising, long pulse width waveform to electrode contacts 2796 and 2793, nerve cuff electrode 2790 may stimulate the small diameter fibers contained in fascicle 2777a of nerve 2792. Similarly, as shown in FIG. 13Q, by applying an exemplary fast rising, short pulse width waveform to electrode contacts 2794 and 2795, nerve cuff electrode 2790 may stimulate the large diameter fibers contained in fascicle 2777b of nerve 2792. Fascicles 2777a and 2777b may be stimulated simultaneously or separately. In embodiments, where it is desirable to stimulate fibers contained in fascicles 2777a and 2777b, the pulse generator (e.g., INS 50) may be provided with dual output ports.

Description of an Exemplary Respiratory Waveform

Figure 14A:
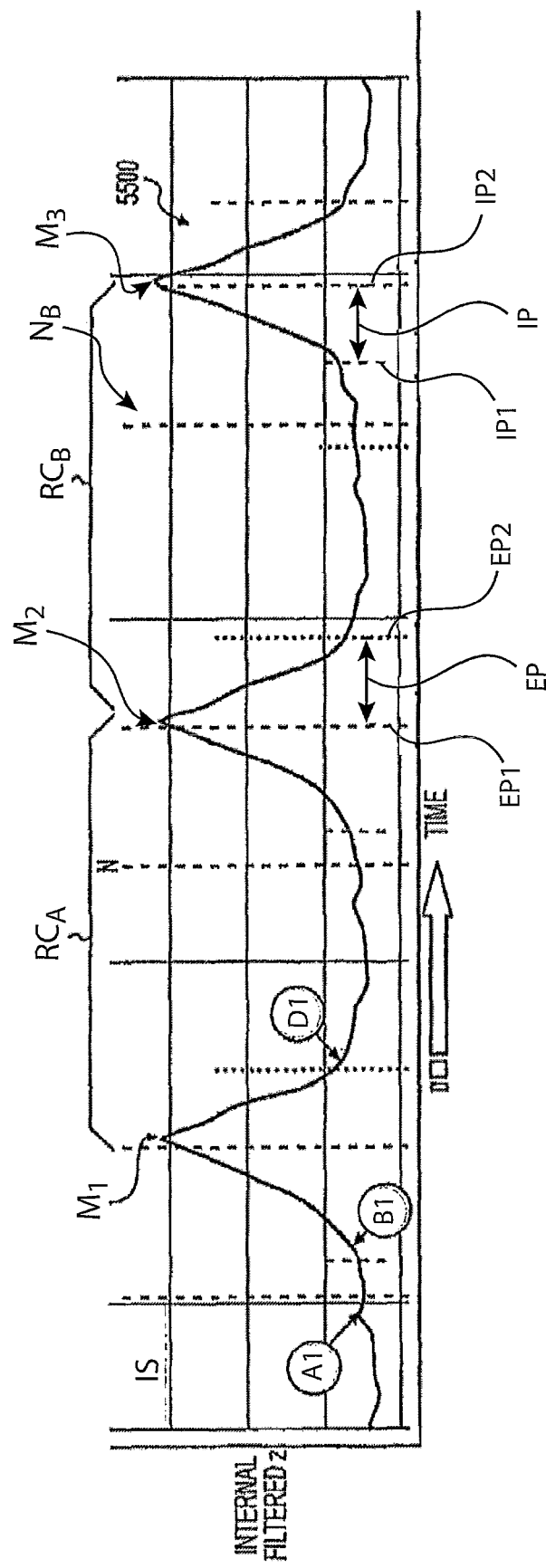
FIG. 14A illustrates an exemplary waveform of a patient's respiratory cycle.

Turning now to FIG. 14A, there is depicted an exemplary respiratory waveform 5500 for two complete respiratory cycles A and B, generated by a sequential plotting of respiratory motion over time (with the respiratory motion measured, in this example, with an impedance signal). As illustrated in FIG. 14A, exemplary waveform 5500 provides peaks M that indicate the onset of expiratory phases or indicate the conclusion of inspiratory phases. The peaks M also define a period of the respiratory cycle, such as the respiratory cycles A and B illustrated in FIG. 14A. The exemplary waveform 5500 also shows that peaks M may occur at regular intervals of approximately 3-4 seconds. Thus, it may be possible to predict the occurrence of subsequent peaks M, and consequently, the onset of expiration for future respiratory cycles.

After explained in more detail below, in order to deliver a stimulus to a patient in accordance with the principles of the present disclosure, a start of stimulation may be calculated by first predicting the time intervals between the start of expiration (or the end of inspiration) for subsequently occurring respiratory cycles. Next, in order to capture the entire inspiratory phase or period of the respiratory cycle (including a brief pre-inspiratory phase of approximately 300 milliseconds), stimulation may be started at a time N that is prior to the next predicted onset of expiration by approximately 30% to 50% of the time between subsequently occurring expiratory phases. Stated another way, after determining an estimated time period until a next respiratory cycle, and after the detection of a qualifying expiration peak M, a stimulation may be started at a time that is approximately 50-70% of the estimated time period after the detection of the expiration peak M. It is believed that stimulating less than 30% or more than 50% prior to the next expiratory phase may result in an inadequate stimulation period and muscle fatigue, respectively.

In the exemplary embodiment illustrated in FIG. 14A, the respiratory waveform 5500 can be defined by a number of respiratory cycles measured over time, such as a respiratory cycle A $RC_A$ and/or a respiratory cycle B $RC_B$ as illustrated in FIG. 14A. The respiratory cycles A and B illustrated in FIG. 14A represent one or more such cycles distributed over a time period. The respiratory cycles A and B can be obtained by measurements of respiration movements, such as those described previously, and can be determined by calculations based on earlier measured respiratory cycles. For clarity, the respiratory cycles A and B illustrated in FIG. 14A are presented as two subsequent measured respiratory cycles to illustrate certain respiratory waveform features described in detail below. However, in some embodiments, FIG. 14A is to be understood to illustrate a respiratory cycle A that represents a measured respiratory cycle and to illustrate a respiratory cycle B that represents a future calculated respiratory cycle.

The respiratory waveform 5500 can be defined in several ways: by a series of measured respiratory cycles A (with only one shown in full in FIG. 14A), by one or more measured respiratory cycles A and one or more measured respiratory cycles B over time, and/or by one or more measured respiratory cycle(s) A followed by a respiratory cycle B that is calculated from data obtained from the one or more preceding respiratory cycle(s) A. In an exemplary embodiment, the respiratory cycles A and/or B can be selected so as to place the two cycles adjacent to each other, as illustrated, or selected to place the two cycles farther apart in time with the inclusion of one or more additional respiratory cycles disposed between multiple respiratory cycles A, or after respiratory cycle A and before respiratory cycle B. For clarity in FIG. 14A, a single respiratory cycle A and a single respiratory cycle B are illustrated adjacent to each other in time, with features shown for one exemplary respiratory cycle being applicable to any other respiratory cycle. Accordingly, in FIG. 14A, features that are applicable to respiratory cycle A are shown on respiratory cycle B for clarity in the illustration. As can be appreciated, the features of respiratory cycle B should be transposed to respiratory cycle A when respiratory cycle A is a measured respiratory cycle and respiratory cycle B is a predicted respiratory cycle based on the measurements obtained with regard to one or more respiratory cycle(s) A.

The respiratory cycles (A or B) can be defined by the identification of peaks M within the waveform 5500 that can indicate the maximization of lung air intake for that respiration cycle and also indicate the end of inspiration and/or the beginning of expiration. As can be appreciated, the end of inspiration and the beginning of expiration may be separated from each other by an insignificant time when exhalation immediately follows inhalation, or be separated by a longer time corresponding to the holding of a breath or the obstruction of an exhalation. The waveform 5500 can also define an expiration period or phase EP which is a time period over which air exits the lungs, with the boundaries of the expiration period EP defined by an expiration start EP1 (or M) and an expiration end (EP2). Likewise, the waveform 5500 can define an inspiration period or phase IP which is a time period over which air enters the lungs and includes attempts to bring air into the lungs (such as during obstructed or disordered breathing events), with the boundaries of the inspiration period IP defined by an inspiration start IP1 and an inspiration end IP2 (or M). As stated previously, the peak M can indicate inspiration end IP2 as well as indicate expiration start EP1 when the time between inspiration end IP2 and expiration start EP1 is zero or insignificant. As also state previously, the peak M can be expressed as a plateau when there is a difference in the timing of inspiration end IP2 and expiration start EP1 representing a holding or obstruction of an exhalation for said different in the timing. Also, the peak M can be defined to correspond to both or only one of expiration start EP1 and inspiration end IP2, and is preferably associated with expiration start EP1.

In the exemplary embodiment of FIG. 14A, sensor information obtained regarding respiratory cycle A (or several respiratory cycles A, not shown) can be used to predict the timing of respiratory cycle B and used to determine the timing of a stimulation delivered during respiratory cycle B. The start time N of the stimulation may be calculated by using the time interval defining respiratory cycle A (or respiratory cycles A) that extends from peak $M_1$ (at expiration start EP1 of cycle A or at the inspiration end IP2 of the prior respiratory cycle) to peak $M_2$ (at inspiration end IP2 of cycle A or at the expiration start EP1 of the subsequent cycle) to provide a time value (or multiple time values) that can be used to predict the timing of peak $M_3$ that corresponds to the inspiration end IP2 of cycle B or the expiration start EP1 of the cycle following cycle B. The prediction of the timing for peak $M_3$ can be obtained by assigning to cycle B the same or a similar duration that was observed for cycle A, or by calculating the duration of cycle B by using an average or mean of two of more cycles A to provide the timing for peak $M_3$, or by calculating the duration of cycle B by observing two or more cycles A and identifying a cycle A or a subset of the cycles A that is based on an acceptable quality data set or that conforms with a predefined template for respiratory cycles to provide the timing for peak $M_3$, or by calculating the duration of cycle B by using a parameter from a table stored in memory or calculated by an algorithm to provide the timing for peak $M_3$. Next, in order to capture the entire inspiratory period IP of respiratory cycle B, including the brief pre-inspiratory period of approximately 300 milliseconds, stimulation may be timed to start at a time $N_B$ that is calculated to be prior to the predicted time of expiration $M_3$ by an offset time interval that is approximately 30% to 50% of the duration calculated for respiratory cycle B. For example, referring to FIG. 14A, the predicted time of peak $M_3$ can be used to calculate an offset at an earlier time by subtracting from the time for peak $M_3$ a value corresponding to 30% to 50% of the duration time of respiratory cycle B to arrive at the stimulation time $N_B$. As can be appreciated, the offset of approximately 30% to 50% defines a window of time during which the start of stimulation $N_B$ is preferably disposed in order to have the stimulation capture the entire inspiratory phase IP. As can also be appreciated, the stimulation $N_B$ can be disposed outside of the 30% to 50% window to account for variations in the respiratory cycles due to patient characteristics and health, disease state, physiological factors, and environmental factors. The stimulation can continue until the time of expiration at or near peak $M_3$ is reached or it can be continued into or through the expiration period EP. As can also be appreciated, the offset time interval that provides the timing of time $N_B$ can be calculated by adding time directly to the detection time of the measured expiration $M_2$ instead of by subtracting from the estimated time of expiration $M_3$, so that the stimulation start time $N_B$ is placed at a time that is approximately 50% to 70% after the detection of expiration $M_2$.

In some embodiments, however, it is contemplated that an adequate measure of respiration may not be available, such as, for example, when a relied-upon signal has failed. In these embodiments, it is contemplated that the implanted neurostimulator system may be configured to respond in one or more of the following three ways. First, the implanted neurostimulator may completely cease stimulation until an adequate signal is acquired. Second, the neurostimulator may deliver continuous simulation pulses of predetermined durations (e.g., up to 60 seconds) until an adequate signal is acquired; or if an adequate signal is not acquired in this time, the stimulation will be turned off. Third, the neurostimulator may continue to stimulate at the same or a fraction (e.g., one quarter) of the stimulation rate for the most recently measured respiratory cycle. That is to say, the neurostimulator may deliver stimulation pulses of relatively long durations at a frequency that is less than the frequency of stimulation utilized with an adequate measure of respiration. Alternatively, the neurostimulator may deliver stimulation pulses of relatively short durations at a frequency that is greater than the frequency used with an adequate measure of respiration.

Description of an Exemplary Stimulation Pulse

Figure 14B:
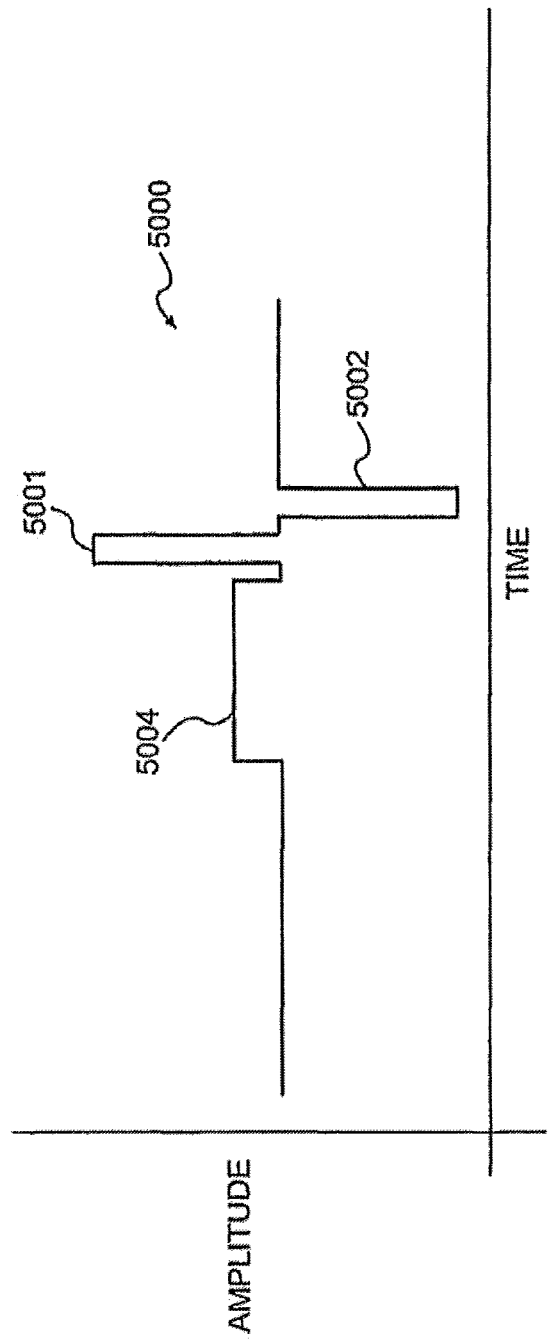
FIG. 14B illustrates an exemplary stimulation waveform.

Turning now to FIG. 14B, there is depicted an exemplary stimulation pulse waveform 5000 that may be emitted from an INS in accordance with the principles of the present disclosure. Typically, exemplary stimulation pulse waveform 5000 may include a square wave pulse train having one or more square wave pulses 5001 of approximately 1 to 3 volts in amplitude, a duration of approximately 100 ms, and a frequency of approximately 30 Hz, assuming a 1000 ohm impedance at the electrodes and a constant current or voltage.

In some embodiments, exemplary stimulation pulse waveform 5000 may include a bi-phasic charge balanced waveform square pulses 5001 and 5002, as depicted in FIG. 14B. Square pulse 5002 may be included in waveform 5000 to, among other things, promote efficient stimulation and/or mitigate electrode corrosion. However, square pulse 5002 may be excluded from waveform 5000 as desired. Furthermore, although the depicted exemplary waveform 5000 includes square pulse 5002 that exactly balances the stimulation wave pulse 5001, in certain circumstances, square pulse 5002 may not exactly balance the stimulation wave pulse 5001, and may not be a square pulse.

In some embodiments, exemplary stimulation pulse waveform 5000 may include the delivery of a low amplitude (e.g., below the stimulation threshold), long duration, pre-stimulation pulse 5004. The pre-stimulation pulse 5004 may include any suitable low amplitude, long duration pulse, and may be provided approximately 0.5 ms before the delivery of a first stimulation pulse 5001.

Pre-stimulation pulse 5004 may facilitate selectively stimulating certain fibers of a nerve, such as, for example, the hypoglossal nerve or the superior laryngeal nerve. In particular, when stimulating the hypoglossal nerve, the presence of a pre-stimulation pulse, such as, for example, pulse 5004, before a stimulation pulse (e.g., the bi-phasic stimulation pulse 5001 depicted in FIG. 14B) may serve to saturate the large diameter fibers of the nerve so as to allow the stimulation pulse 5001 to only affect (e.g., stimulate) the smaller diameter fibers of the nerve. In circumstances where a nerve (e.g., the hypoglossal nerve) may be stimulated for extended periods of time, a pre-stimulation pulse 5004 may be selectively introduced to waveform 5000, so as to permit selective switching between stimulating the large and small diameter fibers of the nerve, in order to reduce muscle fatigue. Similarly, in situations where OSA may be treated by stimulating the superior laryngeal nerve to open the upper airway through a reflex mechanism, the presence of pre-stimulation pulse 5004 may serve to saturate the larger diameter efferent fibers so as to allow the stimulation pulse 5001 to only affect the smaller diameter afferent fibers of the nerve.

Detection of Airway Obstruction and OSA Events

Referring again to FIG. 14A, individual waveforms can be identified within the respiratory waveform 5500 and further analyzed to identify patient status and the occurrence of obstructive sleep apnea events. An individual waveform can be defined to be a portion of the respiratory waveform extending between two sequential impedance peaks (e.g., peaks M of respiratory cycle A in FIG. 14A) or between two other similar or repeated respiratory waveform features (e.g., a series of peaks M defining multiple respiratory cycles A, shown in part in FIG. 14A). Features of the individual waveforms and the respiratory waveform 5500 can be identified and analyzed to determine patient status, sleep-related events, and responsiveness to therapy, and can be used to adjust therapy parameters. As can be appreciated, the respiratory waveform 5500 can also be characterized with data provided from any type of sensor configured to detect breathing or breathing motions, such as an airflow sensor positioned to measure the flow of air into and out of the lungs, to provide an airflow signal that can be used in a similar manner as, and correlated to, the impedance value illustrated in FIG. 14A. Likewise, a pressure sensor disposed in or on the chest can detect breathing motions by the changes in pressure detected by the sensor. Similarly, an accelerometer disposed in or on the chest can be configured to detect breathing motions or, in another embodiment, breathing sounds can be detected with a microphone or other acoustic sensor. In the exemplary embodiments and the techniques described below, it can be further appreciated that techniques applied to impedance values and respiratory waveforms defined by impedance values can be equally or equivalently applied to airflow, pressure, and motion values and respiratory waveforms defined by values representing airflow, pressure, and motion.

Figure 15A:
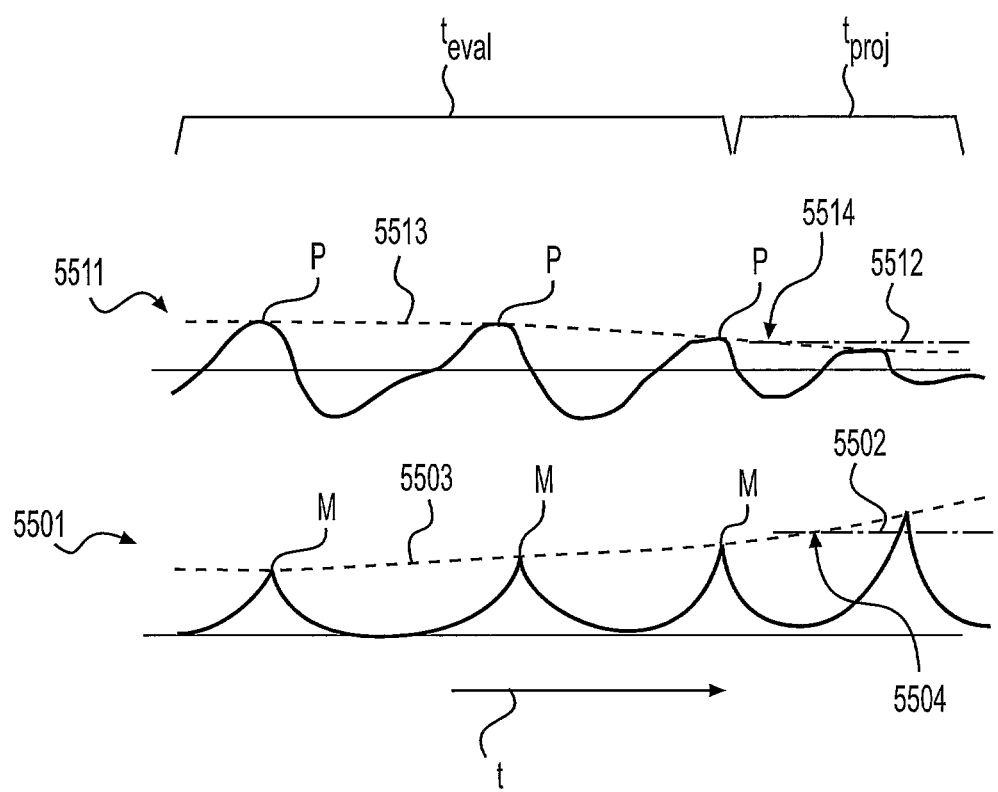
FIGS. 15A-15F illustrate exemplary airflow and impedance respiration waveforms.

FIG. 15A illustrates a series of respiratory cycles measured with two measurement methods over the same period of time. The first method measures motion to identify respiratory activity and, in the illustrated embodiment, uses impedance to measure movement of the chest corresponding to breathing, as described above. The second method measures airflow to identify respiratory activity and, in the illustrated embodiment, uses an airflow sensor measuring the passage of air at a patient's nostrils. The illustrated respiratory cycles represented in waveform 5501 (generated with the first method) and waveform 5511 (generated with the second method) show a breathing pattern that is initially ordered and then degrades to a disordered breathing pattern as time (t) progresses. As illustrated, the degradation and the presence of disordered breathing can be detected by an increase in the magnitude of the impedance peaks M over time, which shows that greater chest motion and greater chest extension is required by the patient to draw in a labored breath as compared to a normal, ordered, unobstructed, and/or not flow limited breath achieved earlier along the timeline. The degradation can also be detected by a gradual decrease in the magnitude of the airflow peaks P over time, which shows that less airflow is achieved by the patient as the patient attempts to draw in a labored breath as compared to a normal breath achieved earlier along the timeline. Both the waveforms 5501 and 5511 may be compared to thresholds 5502 and 5512, respectively, described in detail below. It should be understood that two measurements are displayed in FIG. 15A to illustrate different approaches for identifying disordered breathing and to illustrate how two different approaches can be used together to identify disordered breathing. It should be further understood that the same identification of disordered breathing may be achieved with a single measurement technique or with other techniques described above (such as with the use of a pressure sensor or an accelerometer to detect breathing) and described in the art.

With further reference to FIG. 15A, the respiratory waveform 5501 and 5511 and the peaks M and P may be analyzed to identify trends 5503 and 5513 that are generated from a comparison of peaks M and P over an evaluation time period $t_{eval}$ during which actual measurements of peaks M and P are used to calculate the trends 5503 and 5513. As can be appreciated, the trends 5503 and 5513 can be based on the magnitudes of peaks M and P or on other features provided in respiratory waveforms 5501 and 5511, or on a combination of peaks M and P and such other features. For example, an area under each peak M and P (between points where the respiratory waveforms intersects the x-axes shown in FIG. 15A) can be used for calculation of the trends 5503 and 5513. Furthermore, although the trends 5503 and 5513 are shown in FIG. 15A to be a linear best fit of the measured peaks M and P over the evaluation time period $t_{eval}$, the calculation of the trends 5503 and 5513 can be achieved with other known methods or using methods that give different weights to the measured peaks M and P. The trends 5503 and 5513 can also provide a slope value indicating a degree to which the trends 5503 and 5513 are moving towards or away from the thresholds 5502 and 5512. As illustrated in FIG. 15A, the trends 5503 and 5513 can be extrapolated to extend into a future projected time period $t_{proj}$ to estimate an intersection point 5504 and 5514 where it is estimated that the trends 5503 and 5513 will exceed, cross, and/or surpass the thresholds 5502 and 5512. In another embodiment similar to FIG. 15A but not requiring a projected time period $t_{proj}$, the evaluation time period $t_{eval}$ can be extended to include at least the intersection point 5504 and 5514 so that the exceeding, crossing, and/or surpassing of the thresholds 5502 and 5512 by the trends 5503 and 5513 is identified by a detection of a peak M or P that is on the other side of the threshold 5502 and 5512. Although not shown in FIG. 15A, it can be appreciated that the trends 5503 and 5513 can be reduced or flattened (due to, for example, an application of a nerve stimulation therapy). Although not shown in FIG. 15A, it can also be appreciated that the trends 5503 and 5513 can be reversed (due to, for example, an application of a nerve stimulation therapy), so that the trends 5503 and 5513 (when calculated for later time periods) again cross the thresholds 5502 and 5512, thereby indicating a return to a non-disordered breathing state of the subject.

The amplitude of the impedance peaks M of respiratory waveform 5501, or the peaks P of respiratory waveform 5511, can be compared to a threshold value 5502 or 5512 to determine the level of effort required during a respiratory cycle. A high or otherwise significant level of respiratory effort is indicated when an impedance peak value M exceeds or surpasses (rises above) a threshold 5502, which can identify disordered or atypical breathing indicative of an obstructive sleep apnea event. Likewise, a low or significant airflow peak value P that exceeds or surpasses (falls below) a threshold 5512 can be used to identify disordered or atypical breathing. As can be appreciated, the measurement technique used to acquire the respiratory waveform, and the selection of the threshold, may require calibration based on a baseline related to the normal or usual respiratory effort for the patient, and to account for the configuration of the impedance, airflow, pressure, accelerometer, or other sensors measuring the respiratory effort.

With further reference to FIG. 15A, as illustrated, a patient can be monitored to measure respiratory movement or effort and to measure airflow or the volume of air entering and leaving the patient's lungs, so as to identify disordered breathing events. The measurement of respiratory movement or effort may be acquired directly or indirectly with an impedance sensor, a pressure sensor, an accelerometer, or with any of the sensors or techniques described above or known in the art. For example, a measurement of airflow or air volume may be acquired directly with an airflow sensor disposed near the patient's nostrils. In another example, an airflow measurement may be obtained indirectly with an impedance sensor disposed to detect the movement of the chest and configured to calculate the volume of air entering or leaving the lungs. In an example applicable to both direct and indirect measurement methods, a pressure sensor can be disposed in the chest wall that provides direct measurement of pressure relating to the movement of the chest during breathing, and that simultaneously provides indirect measurement of airflow by using detected chest movements to estimate the volume of the air in the lungs or the passage of air into or out of the lungs. In addition to direct and indirect measurement methods, estimations may be used to generate values characterizing respiration movement, respiration effort, airflow, and air volume. For example, patient body mass or awake lung volume measurements may be determined and a baseline condition of the patient identified that may be correlated to a baseline value for respiration obtained by, for example, an impedance sensor or a pressure sensor as described above. After correlating the baseline value for the patient with sensor measurements, the patient may be evaluated further with voluntary shallow and deep breaths that may be compared to changes in the baseline value so as to provide an estimation of patient breathing changes when sensor measurements are generated during normal sleep periods.

With further reference to FIG. 15A, the patient may be evaluated while awake or asleep to identify and characterize a normal breathing pattern of the patient, and then further evaluated to identify a threshold value or level 5502 and a threshold value or level 5512 at which breathing is considered to require greater effort as compared to breathing during the normal breathing pattern. The characterizing of the normal breathing pattern for the patient may involve evaluating a baseline level of effort or work required for the patient to achieve a necessary level of respiration, which can be measured as an air volume or a blood oxygen level. After characterizing the effort or work associated with normal breathing, the patient can be further evaluated while awake (and simulating labored breathing that requires greater effort, such as breathing through a constricting mask) or asleep (while being monitored in a sleep lab and measuring blood oxygen levels) to correlate respiratory effort or work with blood oxygen levels, for example. Further evaluation may be performed to identify a threshold value or level 5502 at which the breathing can be characterized as labored or deficient, or at which the breathing can be considered insufficient to maintain adequate blood oxygen levels. In a similar fashion, the patient's airflow can be evaluated while awake or asleep to determine a normal airflow or air volume and to determine a labored airflow or air volume that may be used to characterize the air intake threshold value or level 5512. The thresholds 5502 and 5512 may be expressed as a singular value representing a transition to labored breathing and may have the units provided by the measurement technique, or may be expressed as a percentage change relative to the baseline value. Likewise, the thresholds 5502 and 5512 may be expressed as multiple values defining a range or continuum of increasing levels of severity having the units provided by the measurement technique or provided as a percentage change relative to the baseline.

In one embodiment, the respiratory peak threshold 5502 is a percentage increase from the average peak values for a series of qualifying respiratory cycles having peaks M or a similar maximum. For example, a qualifying respiratory cycle may be a cycle that is measured with a sufficient level of quality (e.g., with a minimal number of signal spikes) and, in a further example, a series of qualifying respiratory cycles may be a running average of five sequential qualifying respiratory cycles. In another example, the running average may be based on a greater number of qualifying respiratory cycles such as 10 or 15, and/or the running average may be based on non-sequential respiratory cycles. Also, the running average may be based on values that are weighed so that the running average is biased to favor older or more recent respiratory cycles in the calculation of the running average to provide a long-term running average (biased to favor older cycles) and a short-term running average (biased to favor recent cycles). Older cycles may be cycles that were measured 5 or more cycles prior to a current cycle being measured, or may be 10 or more cycles prior to the current cycle, or may be a series of cycles including, for example, the 5th, 6th, 7th, 8th, 9th, and 10th cycles prior to the current cycle. Recent cycles may be the 5 cycles immediately preceding the current cycle being measured, or may be the 3rd, 4th, and 5th cycles preceding the current cycle. To generate the respiratory peak threshold 5502 for comparison to the current cycle being measured, the running average value may be increased by a predetermined percentage to provide the respiratory peak threshold 5502. For example, for a long-term running average biased to favor older respiratory cycles, the predetermined percentage may be 10%, 15%, 20%, or 25% of a long-term running average. In the 10% example, the respiratory peak threshold is 110% of the long-term running average value and may operate so that immediate changes towards more labored breathing are indicated by increases in the sensed signal, and labored breathing identified when the sensed signal surpasses the 110% respiratory peak threshold. In a similar fashion, to generate the airflow peak threshold 5512 for comparison to the current cycle being measured, the running average value may be decreased by a predetermined percentage to provide the airflow peak threshold 5512. For example, for a long-term running average biased to favor older respiratory cycles, the predetermined percentage may be 10%, 15%, 20%, or 25% of a long-term running average. In the 10% example, the airflow peak threshold is 90% of the long-term running average value and may operate so that immediate changes towards more labored breathing are indicated by decreases in the sensed signal, and labored breathing identified when the sensed signal falls below the 90% airflow peak threshold.

The stimulation therapy described above can be applied prior to the estimated or actual time of the intersection point 5504 and 5514, and subsequently terminated when or after the subject returns to a non-disordered breathing state. The stimulation therapy may open the airway of the subject during a duration of the disordered breathing state. The stimulation therapy can be a applied in several ways. For example, the stimulation therapy can be applied continuously (synchronous or asynchronous with breathing) and evaluated to a greater amplitude when a crossing of a threshold 5502 or 5512 is anticipated or detected. In another example, the stimulation therapy can be configured so that no or minimal stimulation is applied and a therapeutic level of stimulation is applied only when the subject is expected or detected to enter a disordered breathing state. As can be appreciated, battery life can be extended and nerve and muscle fatigue reduced when stimulation is delivered primarily, or only, during anticipated or detected disordered breathing events. As can also be appreciated, when an anticipated disordered breathing event is treated with a therapy delivered prior to the anticipated or detected intersection point 5504 and 5514, the subject may no longer cross the threshold 5502 or 5512 due to the effectiveness of the corrective nerve stimulation therapy and/or the effectiveness of an increase in the existing application of a nerve stimulation therapy. In such a situation, the application of the corrective nerve stimulation therapy or the increase in the level of existing therapy can be timed to terminate when an estimated duration of the anticipated disordered breathing event has passed. Alternatively, instead of using a timing, the termination of the corrective therapy or the resumption of the existing therapy can be based on features or peaks identified in the respiratory waveform or on a subsequent evaluation of a trend or slope of the trend.

With further reference to FIG. 15A, the waveforms 5501 and 5511 can be evaluated for longer periods of time than illustrated in the figure. Over that longer time, the trends 5503 and 5513 can be evaluated to identify multiple periods of time when the trends 5503 and 5513 are within (above or below) the thresholds 5502 and 5512, and multiple times when the trends exceed the thresholds 5502 and 5512. The continuing monitoring of the trends 5503 and 5513 relative to the thresholds 5502 and 5512 or relative to a different value (a predetermined baseline, a fixed threshold, or the x-axis shown in FIG. 15A) can provide long-term data regarding most or the entire sleep period of the patient. This long term data can be evaluated to identify a percentage of the sleep period during which the patient is subjected to a disordered breathing event, with the collective time periods of the disordered breath events compared to the entire time of the sleep period. As can be appreciated, this comparison can provide a disordered-sleep value or percentage that can be a measure of the effectiveness of the therapy or used as a tool to compare the effectiveness of changes or titrations to the therapy. For example, a patient can be monitored while not receiving stimulation therapy to determine a baseline status of the patient characterized with an initial disordered-sleep value, and then the patient can be treated with a stimulation therapy and evaluated in a similar manner to determine a therapeutic status of the patient characterized with a therapy disordered-sleep value. A comparison of the initial disordered-sleep value and the therapy disordered-sleep value can provide a measure of the effectiveness of the sleep apnea stimulation therapy. In another example, a change or titration of the stimulation therapy can be evaluated by treating the patient with a first stimulation therapy and determining a first-therapy status of the patient characterized with a first-therapy disordered-sleep value, and then the patient can be treated with a second stimulation therapy and evaluated in a similar manner to determine a second-therapy status of the patient characterized with a second-therapy disordered-sleep value. A comparison of the first-therapy disordered-sleep value and the second-therapy disordered-sleep value can provide a measure of the effectiveness of the change or titration of the applied sleep apnea stimulation therapy.

Figure 15B:
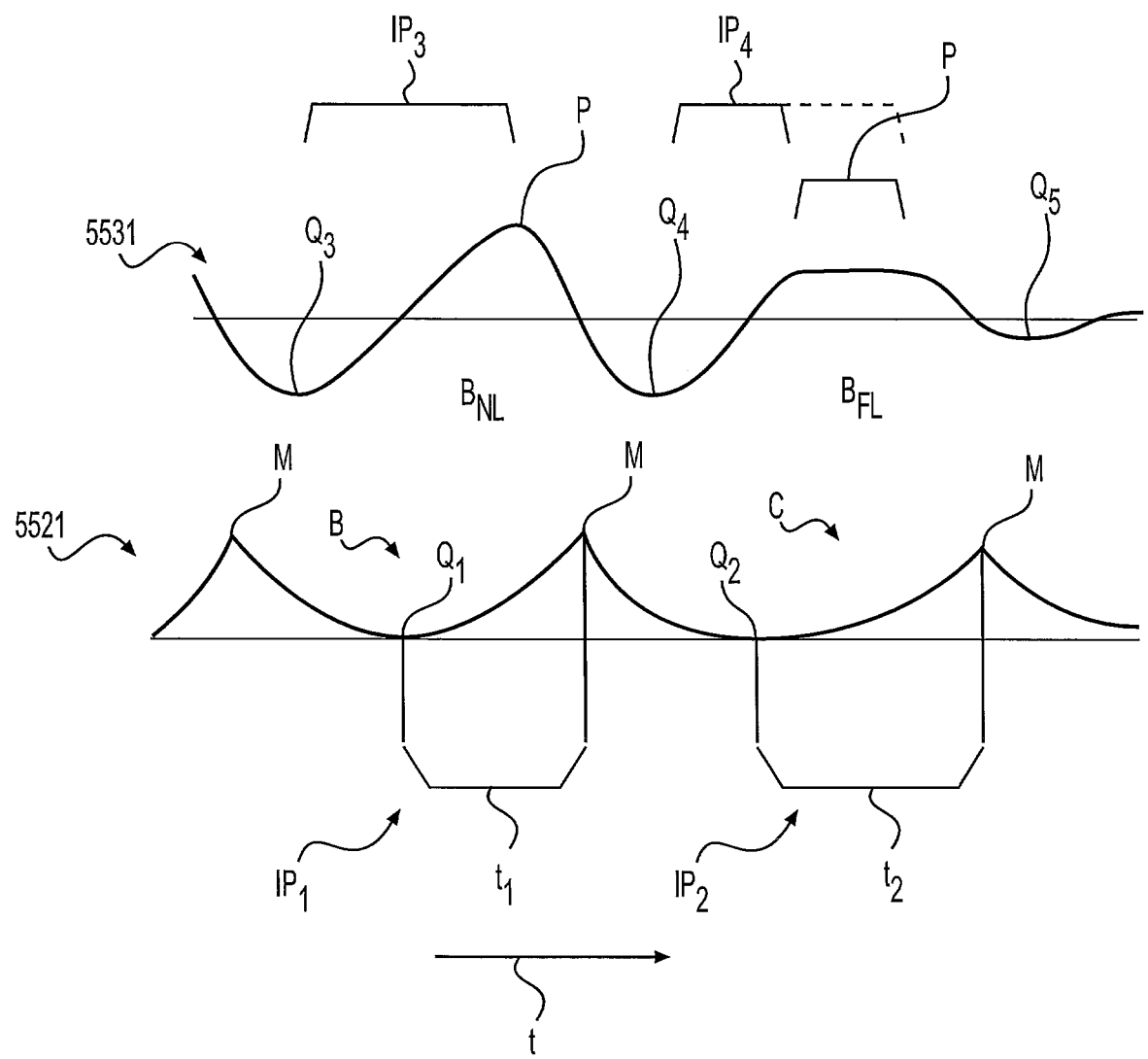

Similar to FIG. 15A, FIG. 15B illustrates a series of respiratory cycles measured with two measurement methods with each method applied to the same period of time (t). Similar to FIG. 15A, the first method measures motion and, in the illustrated embodiment, uses impedance to measure motion, and the second method measures airflow and, in the illustrated embodiment, uses an airflow sensor. The illustrated respiratory cycles contained in waveforms 5521 and 5531 show a normal breathing pattern that is initially normal and then degrades to a disordered breathing as time progresses. As discussed in more detail below, the degradation can be detected by evaluating respiration cycles to identify cycles that become more dominated by an inspiration phase of the respiratory cycle, which indicates that the patient is experiencing labored breathing because more time is needed during the respiratory cycle to draw in sufficient air.

As illustrated in FIG. 15B, the waveform 5521 can include a series of peaks M indicating a maximum intake or breath and/or the beginning of expiration. As also illustrated, a portion of the waveform 5521 extending from one peak M to a subsequent peak M includes both an inspiratory period and an expiratory period to define a respiratory cycle. The respiratory cycle can include signal maximums such as peak M and well as signal minimums such as negative peak Q which corresponds to the end of expiration and/or the beginning of inspiration. In the embodiment of FIG. 15B, the inspiratory period (IP) of a restricted breath can be analyzed to determine whether it provides a value that exceeds a value associated with the inspiratory period (IP) of a normal inspiratory breath, so as to detect disordered breathing. The inspiratory period IP may be defined to be a portion of a respiratory waveform, such as respiratory waveforms 5500 or 5521, that relates to the intake or the attempted intake of air into the lungs. Referring to FIG. 15B, one method of measuring the inspiratory period IP can be to measure the period between an impedance peak M of the respiratory waveform 5521 and the preceding impedance negative peak $Q_1$ to represent a first inspiratory period $IP_1$ of the respiratory waveform 5521, with the inspiratory period $IP_1$ extending from the impedance negative peak $Q_1$ to the impedance peak M over an inspiration time period ($t_1$). The impedance negative peak $Q_1$ can be a minima point or the point where a positive slope of the impedance signal is first encountered and the slope following peak $Q_1$ remains mostly or entirely positive until the end inspiration peak M is detected. It can be appreciated that there are other wave shape analysis techniques for establishing a point on the signal that correlates to the onset of inspiration, and also appreciated that the onset of inspiration correlating to peak $Q_1$ can be based on a measurement of inspiration onset obtained with an airflow sensor such as that shown in waveform 5531. By isolating and analyzing the inspiratory period $IP_1$ of the respiratory waveform 5521, and by analyzing the effort required over the inspiration time period correlated to the inspiratory period $IP_1$, the amount of effort over time (peak-to-peak time) may be determined for the entire inspiration period $IP_1$, which may be provided as a value that is comparable to another respiratory cycle or to a threshold. In an exemplary use of another respiratory cycle, as illustrated in FIG. 15B, a later respiratory cycle C exhibits an increased duration of the inspiratory period $IP_2$ as compared to an earlier cycle B having a shorter inspiratory period $IP_1$.

By comparing the two inspiratory periods $IP_1$ and $IP_2$, it can be determined that the comparatively longer period of inspiratory period $IP_2$ (as compared to an earlier inspiratory period IN indicates that the patient is entering a period of disordered breathing because more of the respiratory cycle is occupied by breath intake as compared to a normal breath intake when the patient experiences non-disordered or normal breathing. In another analysis technique relating to FIG. 15B, a measured inspiratory time period ($t_1$ or $t_2$) of a breath can be identified (from minimum $Q_1$ to the subsequent peak M or from minimum $Q_2$ to the subsequent peak M in FIG. 15B) and compared to the entire duration of the respiratory cycle (e.g., the time (t) from $Q_1$ to $Q_2$ or the time (t) from $Q_2$ to $Q_3$ (not shown)) to identify a disordered breath. A threshold can be identified and applied so that a disordered breath is identified when the inspiratory period IP of the corresponding respiratory cycle (extending from Q to Q for the measured IP) is 40% or more of the entire observed respiratory cycle. In the exemplary embodiment, disordered breathing can be identified with the use of a variety of thresholds. For example, a disordered breath can be identified when an observed respiratory cycle or breath provides a time period for the entire cycle or breath and it is determined that the inspiratory period of that cycle or breath has a inspiratory time period that is 40%, 41%, 42%, 43%, 44%, 45%, 46%, 47%, 48%, 49%, 50%, 51%, 52%, 53%, 54%, 55%, 56%, 57%, 58%, 59%, or 60% of the time period for the entire cycle or breath. In particular, disordered breathing can be identified when the inspiratory period occupies 40% or more, 45% or more, 50% or more, 55% or more, or 60% or more of the time period for the entire respiratory cycle corresponding to the observed inspiratory period.

Referring still to FIG. 15B, the waveform 5531 which is based on an airflow measurement can be used to identify disordered breathing in a manner similar to that described above for waveform 5521 or, as described further below, can be used to support or confirm the identification of disordered breathing detected by, for example, the impedance measurement generating waveform 5521. For example, waveform 5531 can characterize a non-limited breath ($B_{NL}$) extending between minimum $Q_3$ and minimum $Q_4$ with a peak P disposed between the two minimums. As illustrated, the inspiratory period $IP_3$ (extending from minimum $Q_3$ to the subsequent peak P) measured by an airflow sensor may correspond with or be offset from similar measurements taken with another technique (such as that shown in waveform 5521). As with waveform 5521, the non-limited breath $B_{NL}$ can be observed to have an inspiratory period $IP_3$ that occupies a portion of the entire period of inspiration extending from minimum $Q_3$ to minimum $Q_4$. In a later disordered flow-limited breath $B_{FL}$ (extending between minimum $Q_4$ and minimum $Q_5$) the peak P of the breath may not be well defined because the patient is drawing in less air as breathing is attempted but not fully achieved, which is characterized in the waveform 5531 as a peak P that is spread over a plateau or as a peak P followed by a plateau. As with the non-limited breath $B_{NL}$, the flow-limited breath $B_{FL}$ can be observed to have an inspiratory period $IP_4$ that occupies a portion of the entire period of inspiration extending from minimum $Q_3$ to minimum $Q_4$. In the embodiment illustrated in FIG. 15B, the flow-limited inspiratory period $IP_4$ can be the time period between the first minimum $Q_4$ of the respiratory cycle to the first detection of a peak P to indicate the time period over which the patient is achieving breath intake, with a short breath-intake time (compared to earlier breaths or a threshold) indicating disordered breathing. Alternatively, the flow-limited inspiratory period $IP_4$ can be the time period between the first minimum $Q_4$ of the respiratory cycle and the end of the plateaued peak P value to indicate an entire time over which the patient is attempting to take breath, with a long attempted-breath time (compared to earlier breaths or a threshold) indicating disordered breathing. The flow-limited inspiratory period $IP_4$ can be compared to the time period for the entire disordered breath extending from the first minimum $Q_4$ to the next minimum $Q_5$. As described for waveform 5521, the normal breath $B_{NL}$ or normal inspiratory period $IP_3$ can be compared to the disordered breath $B_{FL}$ or disordered inspiratory period $IP_4$ to identified the presence of disordered breathing indicated by the observed increase in the amount of time needed to draw in a breath. Also similar to waveform 5521, the time associated with the disordered inspiratory period $IP_4$ can be compared to the time associated with the disordered breath $B_{FL}$ as a whole to provide a percentage of time of the respiratory cycle that is occupied by breath intake or attempted breathing. For disordered inspiratory periods $IP_4$ extending from a first minimum $Q_4$ to the first identification of a peak P value, a short-breath intake time that is 40% or less of the entire breath cycle (minimum $Q_4$ to minimum $Q_5$) can indicate disordered breathing. For disordered inspiratory periods $IP_4$ extending from a first minimum $Q_4$ to the last identification of a peak P value, an extended-breath intake time that is 60% or more of the entire breath cycle (minimum $Q_4$ to minimum $Q_5$) can indicate disordered breathing. Similar to waveform 5521, these thresholds can vary. For example, the short-breath intake time threshold can be 40% or less, 41% or less, 42% or less, 43% or less, 44% or less, 45% or less, 46% or less, 47% or less, 48% or less, 49% or less, or 50% or less. Similarly, the extended-breath intake time threshold can be 60% or more, 59% or more, 58% or more, 57% or more, 56% or more, 55% or more, 54% or more, 53% or more, 52% or more, 51% or more, or 50% or more.

Similar to FIG. 15A, the detection of disordered breathing with the technique illustrated in FIG. 15B can be used to start or increase the level of a nerve stimulation therapy. The therapy can be started when the patient falls asleep, after the activation of a timer, or after a preset period of time, and the therapy can continue at a first level until disordered breathing is detected, after which the stimulation therapy can be increased for a time period corresponding to the detected disordered breathing event or for a preset period of time. Alternatively, the therapy can be started when the patient provides instruction that sleep is to commence, after the detection of a sleep status of the patient, or after the activation of a timer, and the therapy can continue with the delivery of no stimulation or a minimum level of stimulation, and the stimulation can be turned on to an effective level only when disordered breathing is detected or anticipated. As can be appreciated, the commencement of therapy or the commencement of an increased level of therapy corresponding to the detection of a disordered breathing event can advantageously reduce battery power consumption and reduce nerve and muscle fatigue.

Figure 15C:
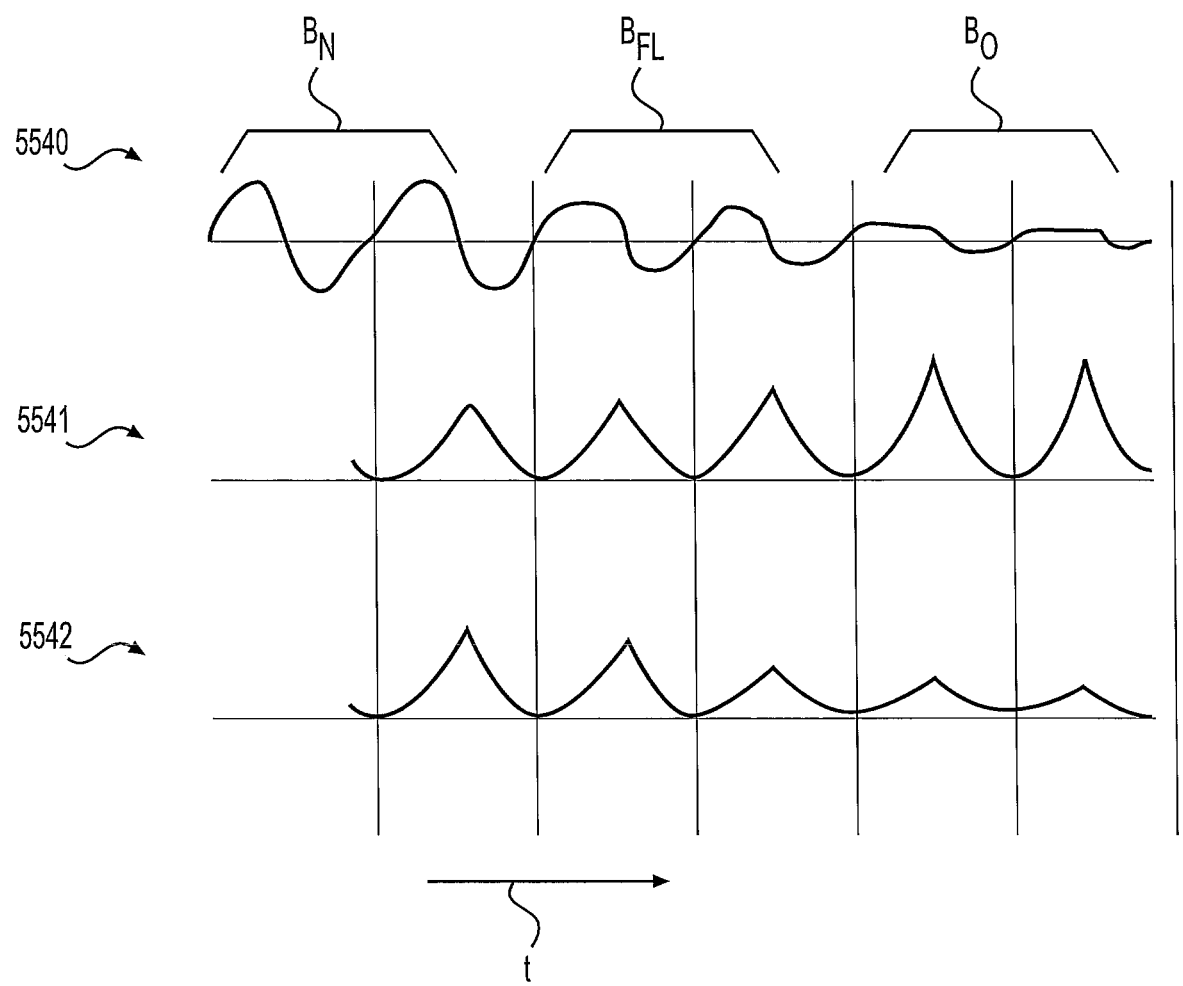

In yet another exemplary embodiment illustrated in FIG. 15C, a detection of paradoxical breathing can be used to identify disordered breathing relating to an obstructed airway or an obstructive sleep apnea event. Paradoxical breathing can occur when the chest expands in an attempt to inspire air when the airway is obstructed, causing the abdomen to contract, resulting in the upper body maintaining a constant or near constant volume until the obstruction is resolved. When multiple signals obtained from sensors located at different parts of the chest are analyzed, the impedance signal between two vectors can be found to be out of phase, thus indicating paradoxical breathing and the presence of an obstructed airway. As illustrated in FIG. 15C, the same respiration cycles are presented of the same time period (t) as an airflow waveform 5540, an impedance vector A waveform 5541 configured to detect chest expansion, and an impedance vector B waveform 5542 configured to detect abdomen contraction. As illustrated, as disordered breathing is observed in the airflow data as time (t) progresses, the data illustrated in the vector A waveform 5541 (chest) diverges from the data illustrated in the vector B waveform 5542 (abdomen), and a comparison of the absolute values of the two waveforms 5541 and 5542 exhibits that there is difference that can be correlated to a disordered breathing event. As illustrated, a patient can transition from a period of normal breathing $B_N$ to a period of flow-limited breathing $B_{FL}$, and then to a period of obstructed breathing $B_O$.

FIG. 15C illustrates a breathing signal in the vector A waveform 5541 (chest) that increases in magnitude over time (t), indicating that the chest is continuing to expand to greater and greater levels as the patient begins a period of disordered breathing. The figure also illustrates a similarly timed breathing signal in the vector B waveform 5542 (abdomen) that decreases in magnitude over the same time (t) period as the vector A waveform 5541, indicating that the abdomen is expanding to lesser and lesser levels as the patient begins a period of disordered breathing. A comparison of the airflow waveform 5540, the vector A chest waveform 5541, and the abdomen vector B waveform 5542 indicates the presence of paradoxical breathing that begins in the time period corresponding to flow-limited breathing $B_{FL}$ and that becomes fully realized in the time period corresponding to obstructed breathing $B_O$. As described above with regard to FIGS. 15A and 15B, a nerve stimulation therapy can be applied when paradoxical breathing is detected or anticipated, or when divergence is observed between a chest respiration measurement (such as vector A) and an abdomen respiration measurement (such as vector B). The therapy can also be based on a comparison of absolute values for the peaks (or other corresponding portions of the waveforms 5541 and 5542) to provide a value representing a difference between the vector A and vector B measurements. As can be appreciated, the value representing the difference can be compared to a threshold, and the threshold can be a predetermined value or a percentage as compared to earlier breathing cycles. For example, paradoxical breathing can be identified when the aforementioned value (difference between vectors A and B) is 50% or more of the magnitude of an earlier peak magnitude observed during the period of normal breathing $B_N$, or to value can be 40% or more, 45% or more, 55% or more, or 60% or more. Similarly, paradoxical breathing can be identified when the vector B value is a certain percentage of the vector A value, such as when the vector B value is 50% or less of the vector A value, or when the vector B value is 40% or less, 45% or less, 55% or less, or 60% or less of the vector A value. As described in embodiments above, a nerve stimulation therapy can be applied or elevated when paradoxical breathing is detected or anticipated.

Figure 15D:
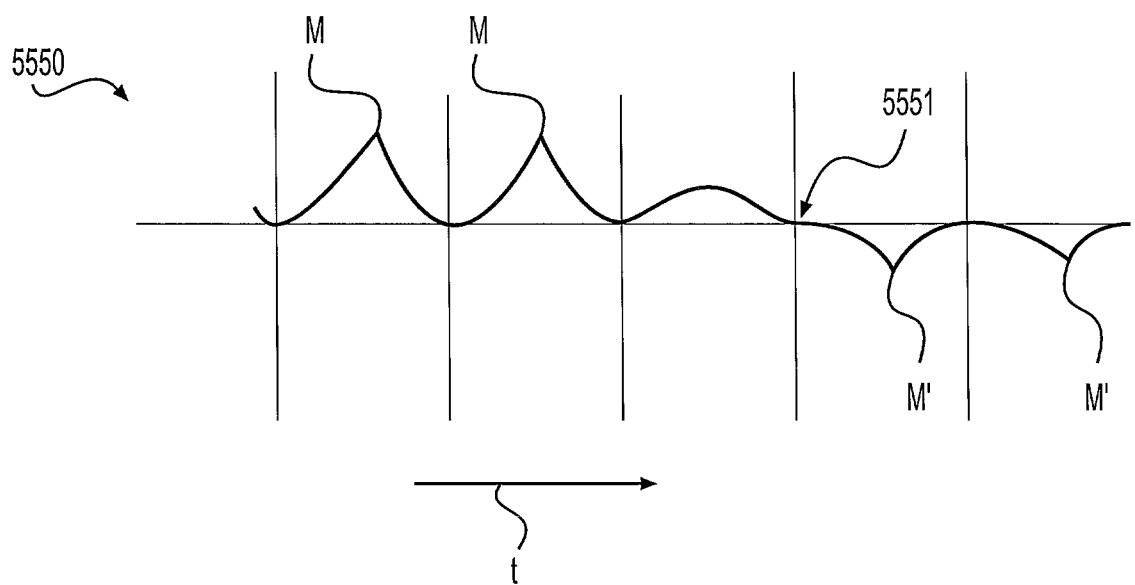

In still another exemplary embodiment illustrated in FIG. 15D, the observed inversion of impedance vectors can be used to identify an obstructed airway or an obstructive sleep apnea event. Some impedance vectors are known to invert during an obstruction event. Referring to FIGS. 14A and 15D, a change in the polarity or the direction of a peak in the respiratory waveform, such as a peak M of the respiratory waveform 5550, can be an indicator that the patient has an obstructed airway or is undergoing an OSA event. As illustrated, the vector(s) subject to inversion (e.g., the vector C illustrated in waveform 5550) can be correlated over the same time period (t) to the data for vector A waveform 5541 and vector B waveform 5542 described in the embodiment relating to FIG. 15C, and the correlation can provide an indication of a disordered breathing event. In the embodiment illustrated in FIG. 15D, the waveform 5550 includes a series of peaks M that reduce in magnitude over time as the vector C approaches an inversion a point 5551, which then leads to a series of anti-peaks or minima M' caused by the signal inversion. As can be appreciated, a nerve stimulation therapy can be initiated or elevated in magnitude when a signal inversion is identified that corresponds to disordered breathing.

Figure 15E:
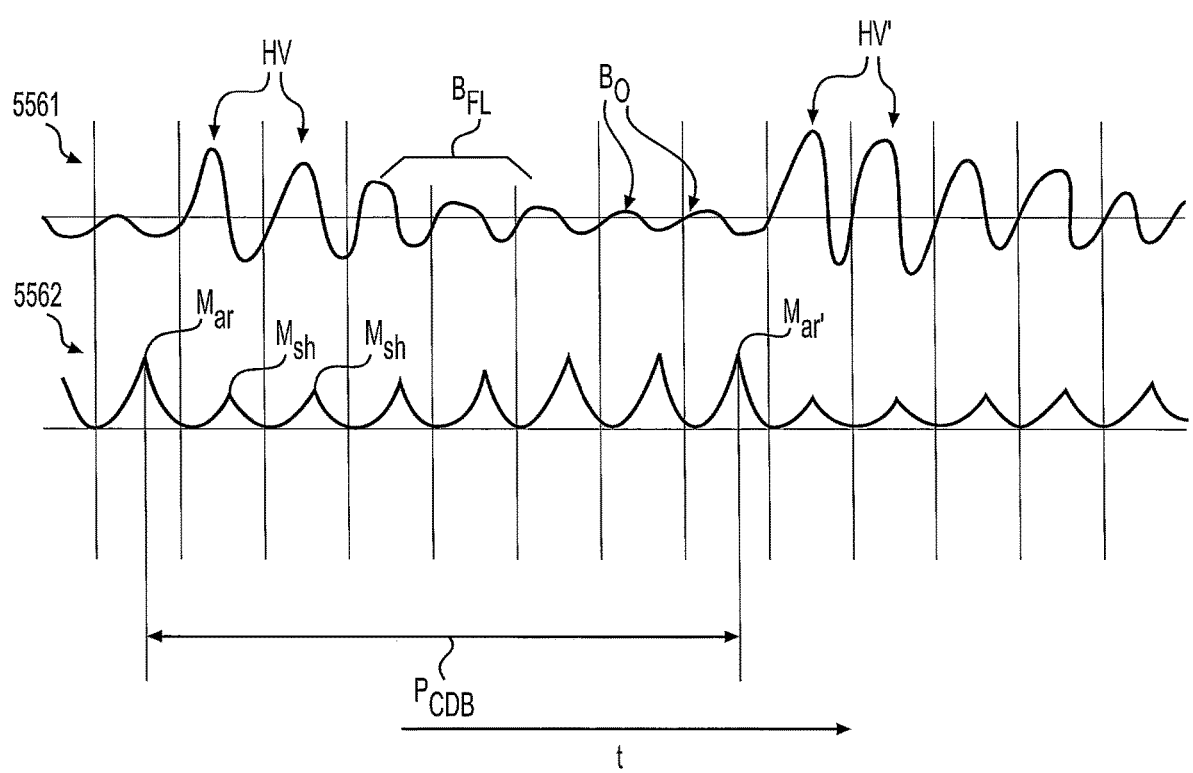

In a further exemplary embodiment illustrated in FIG. 15E, multiple individual respiratory cycles (from a peak M to a subsequent peak M) in waveform 5561 (airflow based, detected with an airflow sensor, for example) and waveform 5562 (chest movement based, detected with impedance, for example) can be analyzed over the same time period (t) to identify disordered breathing patterns indicative of an obstructed airway or an OSA event. Referring to FIGS. 14A and 15E, as the airway collapses to a greater degree with each successive breath, the impedance peaks M will over time progressively increase in magnitude until an arousal from sleep occurs at arousal peak $M_{ar}$, leading to a period of hyperventilation and then leading to hypoventilation (both indicated by HV) and reduced respiratory effort starting at shallow peaks $M_{sh}$. After this period of hyperventilation and hypoventilation HV, the disordered breathing pattern begins again with the presence of flow-limited breaths $B_{FL}$, and then obstructed breaths $B_O$, and then another period having a maximum impedance peak $M_{ar}$, followed by another period of hyperventilation and hypoventilation HV' and shallow breathing peaks $M_{sh}$. This trend or pattern of increasingly greater magnitudes in impedance peaks (the period of cyclic disordered breathing in FIG. 15E), observed over several respiratory waveforms, indicates the degradation of the airway over time and the presence of disordered breathing. Taken together, the cycle starting with arousal peak $M_{ar}$ and ending with the next occurrence of another arousal peak $M_{ar}$, can define a period of cyclic disordered breathing $P_{CDB}$. Blood oxygen saturation levels may also be measured. Blood oxygen saturation levels that fluctuate with approximately the same period $P_{CDB}$ may be indicative of disordered breathing corresponding to OSA. Similarly, EEG signal fluctuation at approximately the same frequency may also be indicative of disordered breathing corresponding to OSA. An observation or detection of a period of cyclic disordered breathing $P_{CDB}$ can be used to indicate a need for elevated therapy or can be used to increase a nerve stimulation therapy to provide greater levels of stimulation in response to the detected cycle or in response to future anticipated arousal peaks $M_{ar}$. Similarly, the time period associated with the $P_{CDB}$ can be analyzed with different therapies or titrations to identify whether changes to the therapy are effective or beneficial to the patient, with longer $P_{CDB}$ cycles indicating an improvement because greater time is realized between consecutive arousal peaks $M_{ar}$.

It should be appreciated that a plurality of respiratory cycles may be analyzed (FIG. 15F), with aspects of one or more of the respiratory cycles over a first time period being compared to aspects of one or more of the respiratory cycles over a second time period. Differences between the aspects of the first time period and the second time period, such as differences between the time periods of $P_{CDB}$ cycles of the first and second time periods, may be indicated by the comparison. Additionally, or alternatively, a breathing pattern may be identified over a first time period, which may be indicative of disordered breathing corresponding to OSA. Identifying repetitions of the breathing pattern in subsequent time periods may confirm the occurrence of the disordered breathing. Stated differently, identifying repetitions in subsequent time periods may increase the confidence in determining the disordered breathing. For example, if the breathing pattern repeats once, sequentially, the occurrence of the disordered breathing may be confirmed, increasing the confidence in determining the occurrence. A third repetition may progressively increase the confidence in or reliability of the determination of the disordered breathing.

Figure 15F:
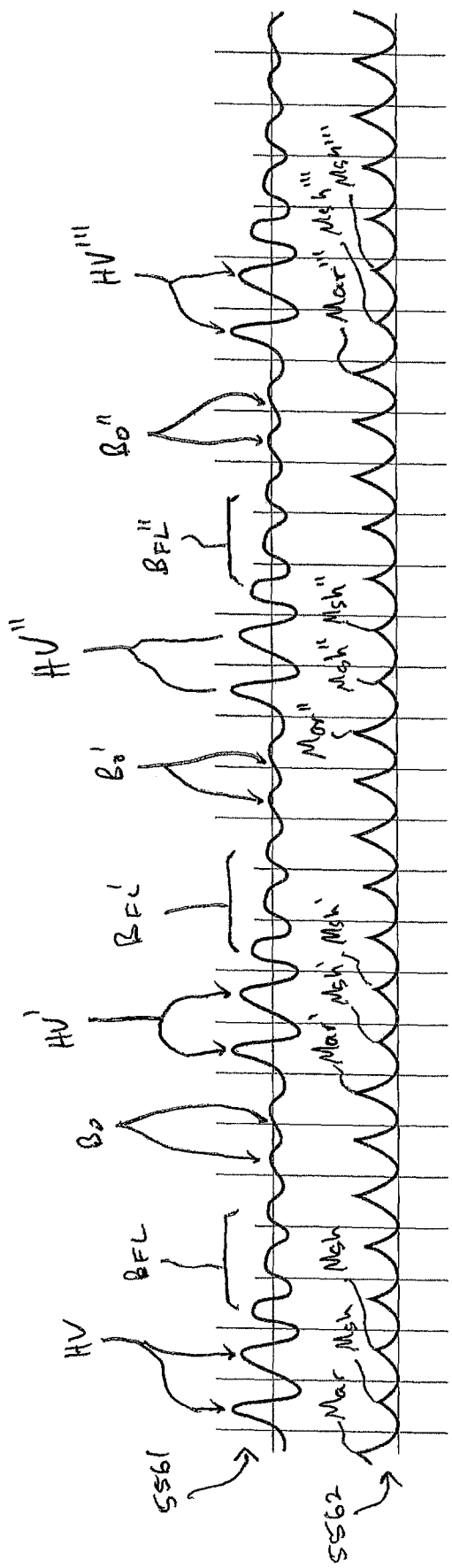

FIG. 15F may show a plurality of $P_{CDB}$ cycles. For example, FIG. 15F may show four of the $P_{CDB}$ cycles from FIG. 15E. Aspects of the curves 5561 and 5562 in FIG. 15F may be similar to aspects of the curves 5561 and 5562 in FIG. 15E, and have been identified with similar reference numbering and lettering, with hash markings to distinguish between different $P_{CDB}$ cycles. It should be appreciated that the $P_{CDB}$ cycles of FIG. 15E may be at the left side of FIG. 15F, with the right side of FIG. 15F showing $P_{CDB}$ cycles in the future (e.g., after the $P_{CDB}$ cycles of FIG. 15E). Alternatively, the $P_{CDB}$ cycles of FIG. 15E may be at the right side of FIG. 15F, with the left side of FIG. 15F showing $P_{CDB}$ cycles in the past (e.g., before the $P_{CDB}$ cycles of FIG. 15E).

In another exemplary embodiment, multiple respiratory waveforms can be observed over time. For example, the respiratory waveforms may be observed in parallel or in series. The respiratory waveforms may be used to identify variability between impedance peaks M or to identify variability in the time periods of individual respiratory cycles. This variability can be correlated with episodes of disordered breathing. For individuals exhibiting variability in impedance peaks or cycle time periods, a calibration can be performed directed at correlating the variability to the probability of a disordered breathing event. In further analysis, patterns in the variability can be identified to further distinguish OSA-related variations from normal variations in respiration during REM or other sleep stages.

In another exemplary embodiment, a first therapy, including a series of first stimulation pulses, may be timed to coincide with at least one of an output of a timer and a detection of a first feature of one of a plurality of respiratory cycles. The first therapy may include, for example, stimulation delivered at time N as a result of the analyses performed in correspondence with FIG. 14A. The first therapy may transition to a second therapy, the second therapy including a series of second stimulation pulses timed to coincide with a detection of a second feature of at least two of the plurality of respiratory cycles. The second therapy may include, for example, stimulation delivered as a result of the analyses performed in correspondence with FIGS. 15E and 15F. Alternatively, the second therapy may occur before the first therapy, with the second therapy transitioning to the first therapy.

With reference to the embodiments illustrated in FIGS. 15A-15F, for each embodiment the subject is a patient, the incoming respiration signal is detected from the body of the patient, and the outgoing stimulation signals is delivered to the body of the patient. However, the presence of the patient is not needed in order to perform the methods or use the devices and systems illustrated in the embodiments of FIGS. 1-15F. For example, instead of a patient, a simulated subject can be provided to generate any of the data that would have been obtainable from the patient when sensors are applied to the patient. In a similar fashion, the respiratory waveform or any other signal parameter can be simulated by a device capable of generating a suitable signal, such as a respiratory waveform simulator that can be, for example, a laptop generating a signal that is supplied to the devices or systems illustrated by FIGS. 1-15F. Likewise, the stimulation signal described in those embodiments can be received by a receiving device instead of the patient, so that the stimulation signal can be analyzed to determine whether it has the characteristics described in the embodiments of FIGS. 15A-15F.

With further reference to the embodiments illustrated in FIGS. 15A-15F, for each embodiment there is described a sensor or an incoming sensor signal that can be involve or implement a variety of sensors or signal forms. In particular, the sensor can include any sensor used in a PSG lab or in a home-based version of a PSB lab, and would include sensors capable of detecting EEG, EKG, $O_2$ saturation, nasal or mouth airflow, an airflow meter, a strip or mask interacting with the mouth or nose to measure airflow, an effort sensor configured to measure breathing effort, or a belt configured to measure the amount of effort required for breathing. Likewise, the signals used in the embodiments of FIGS. 15A-15F can be any signal generated from these various PSG-related devices or a derivative of such signals.

In addition to the above, it can be appreciated by a person of skill in the art that the delivery of a stimulation signal in any of the embodiments illustrated in FIGS. 15A-15F can be proceeded with an conditioning portion of the signal that can a ramping signal that gradually increases the stimulation to the levels described in these embodiments. For example, the initial portion can be in the form illustrated in FIG. 14B. The ramping signal can be inclined to start at a zero value or non-therapeutic value that rises to a therapeutic value. Further examples are described below.

As can be further appreciated, each of the methods described above and, in particular, the methods illustrated by FIGS. 15A-15F can be presented as a series of instructions set forth in labeling, software, or an algorithm associated with a nerve stimulation device or system.

Detection of Status and Stimulation Delivery and Adjustment

Features and patterns in the respiratory waveform 5500 (FIG. 14A) and the sensor signals defining the respiratory waveform, such as an impedance signal, can be used to determine whether the patient is asleep, the start of sleep, and the sleep stage. The identification of sleep status can be used to activate or deactivate a stimulation therapy, used to initiate a stimulation therapy, and used to select parameters of the stimulation therapy.

In an exemplary embodiment, patterns in the sensor signals, such as an impedance signal, can be used to identify sleep stage. A pattern showing highly variable periodicity with little or no movement artifacts can indicate REM sleep. Likewise, greater amplitude peaks M that remain fixed (have low variability) and do not cycle in a crescendo-decrescendo pattern can indicate slow-wave N3 sleep.

In another exemplary embodiment, the sensor signal used to generate the respiratory waveform 5500, such as an impedance signal, can be used to detect the onset of sleep. The detection of sleep onset can be used to initiate the delivery of hypoglossal nerve stimulation for a therapy session. For example, the onset of sleep can be detected by the development of a pattern of respiratory waveforms that have low variability in amplitude and time period as compared to an awake state or as compared to an OSA event state. An external signaling device can be used by the patient to indicate that sleep is planned, and timers or the counting of respiratory cycles can be employed to determine whether a period of low variability in the respiratory waveform amplitude and time period has been maintained sufficiently long enough to identify the onset of sleep. After a sufficiently long period of low variability is identified, the stimulation therapy can be initiated.

In still another exemplary embodiment, the sensor signals used to generate the respiratory waveform, such as an impedance signal, can be used to sense the sleep state and to optimize the stimulation therapy in response to the sensed sleep state. The optimization of the therapy can be supplemented with an external monitoring means such as an in-lab PSG or a home diagnostic system configured to communicate with the implanted neurostimulator to allow adjustment of the stimulation amplitude or electrode field configuration (field steering). It has been observed that deep sleep states, such as the REM sleep state, are typically less arousable states and therefore, less sensitive to high levels of stimulation therapy. When deep sleep states are detected, such as with the techniques described above, the stimulation therapy can be provided at a level that is greater than the level tolerated when the patient was awake, and at a level that is greater than the stimulation levels useable in other sleep states (because the stimulation levels in these other sleep states will arouse the patient). Likewise, field configurations that would not be tolerated in the awake state or not useable in non-deep-sleep states (because of the potential to wake the patient) can be implemented in when a deep sleep state is detected.

The detection methods described above, that identify disordered breathing events, can be used to adjust the stimulation therapy and to adjust the parameters of the stimulation therapy, and can be also used to create a record of the effectiveness of the stimulation therapy settings for future reference and for use in adjustments to the stimulation therapy.

In an exemplary embodiment, the effectiveness of the stimulation therapy can be improved by increasing the amplitude of the stimulation when a disordered breathing event is detected, and then subsequently decreasing the amplitude of the stimulation when no disordered breathing events are detected to save battery life and minimize potential arousals from sleep associated with high-amplitude stimulations. Over several such cycles of high amplitude followed by low amplitude stimulations, the increased amplitudes in this cycle can be progressively increased or decreased to identify the maximally-effective stimulation amplitude, i.e., the maximum stimulation amplitude at which further amplitude increase produces no benefit.

In another exemplary embodiment, the electrode configuration can be adjusted with field steering techniques to produce different stimulation electrical fields. The electrode configurations and electrical fields that can be implemented may be stored in a memory available to the neurostimulator, or pre-selected by an operator, and made useable during the stimulation therapy. When a disordered breathing event is detected, the neurostimulator can cycle through the available electrode configurations and electrical fields to determine which provide better efficacy, improved disruption of disordered breathing events, and less arousal from sleep. The best of the cycled configurations and fields can be implemented by the device in accordance with a protocol preset in the neurostimulator or selected by the operator or user, and the response of the patient to the stimulation can be recorded for further analysis to establish future stimulation therapies. As can be appreciated, the cycling of predefined or preselected electrode configurations and electrical fields can also be accomplished without input from a sensor or analysis of a respiratory waveform, with the cycling put into effect according to a schedule or in response to a parameter that is not a function of the respiratory cycle.

In yet another exemplary embodiment, the delivery of the stimulation waveform 5000 can be adjusted to improve efficacy and reduce power consumption. The stimulation waveform can be changed to a different stimulation waveform in a subsequent delivery of the stimulation waveform, to provide an isolated difference in therapy or to define a pattern or cycle of stimulation waveforms that provide a therapy not achieved with a single waveform. Various stimulation waveforms can be stored in a memory available to the neurostimulator, or pre-selected by an operator, and made useable during the stimulation therapy. When providing a stimulation therapy, the neurostimulator can provide stimulation using a single stimulation waveform A that is provided for each respiratory cycle, to provide a pattern that is A-A-A-A-A and so on. Alternatively, the neurostimulator can provide stimulation using a single stimulation waveform A that is provided at every other respiratory cycle with a series of non-stimulation respiratory cycles disposed between each stimulated respiratory cycle, or provide stimulation with two stimulation waveforms with one being the aforementioned stimulation waveform A and the other being a null stimulation waveform 0 that has zero or a non-therapeutic amplitude, to provide a pattern that is A-0-A-0 and so on. In another alternative, two or more stimulation waveforms (e.g., a stimulation waveform A and a stimulation waveform B) can be implemented and configured to alternate with each other in a pattern or in a cycle that is repeated, to provide a pattern that is A-B-A-B and so on. In an exemplary embodiment, stimulation waveform A may be a square waveform, and stimulation waveform B may be a triangular waveform or any other suitable waveform of a differing parameter. In a further example stimulation waveform A may have a first amplitude and stimulation waveform B may have a second amplitude different than the first amplitude. In yet another alternative, three waveforms (that may include the null waveform 0) can be implemented to provide a pattern that is A-B-0-A-B-0 and so on. As described above, the variation of the delivery of the stimulation waveform can be evaluated by analyzing the effect the stimulation has on the respiratory waveform. As also described above, the best of the stimulation waveform configurations can be implemented by the device in accordance with a protocol preset in the neurostimulator or selected by the operator or user, and the response of the patient to the stimulation can be recorded for further analysis to establish future stimulation therapies. As can be appreciated, the cycling of predefined or preselected stimulation waveform patterns can also be accomplished without input from a sensor or analysis of a respiratory waveform, with the cycling put into effect according to a schedule or in response to a parameter that is not a function of the respiratory cycle.

It is known that the severity of the OSA affecting an individual can change over time due to the progression of the OSA, changes to the underlying causes of the apnea, and the introduction of new factors affecting sleep quality. For example, over time a person suffering OSA may be affected by changes in age, diet, medications, and BMI and influenced by factors affecting sleep or respiration such as seasonal allergies, respiratory illness and colds, diseases or medications affecting sleep and breathing, dietary or medication changes, onset of menopause in women, anxiety, and insomnia. Each of these factors taken alone or together can lessen or worsen the apnea and the efficacy of some stimulation therapies. The above-described respiratory breathing monitoring and therapy administration and adjustment techniques can be employed to identify and react to changes in the patient's OSA condition over time. The identification of the changes can be achieved by scheduling regular re-optimizations of the stimulation therapy by, for example, using the aforementioned alternative-stimulation cycling techniques to re-evaluate the efficacy of the current and alternative stimulation therapies. In another approach, a history of comparable respiratory waveforms can be maintained or a parameter derived from historical respiratory waveforms that characterizes the waveform over a time period, such as the calculation of a range of median impedance amplitudes over a moving three-month window from which it can be determined that the window is progressively tightening, expanding, or moving to a higher or lower amplitude value or range of values to indicate a progression of the OSA disease state. Once changes are identified, the therapy can be adjusted to account for the changes and the progression of the OSA disease state. For example, the stimulation can be adjusted by identifying and implementing a new or modified stimulation therapy identified by, for example, the above-described cycling of alternative stimulation therapies. In another example, the stimulation system can report to the user or caretaker the reduced efficacy of the current therapy and/or the need for a re-optimization of the current therapy. In additional exemplary embodiments, when the stimulation system employs a stimulation therapy that allows for incremental increases in the stimulation amplitude and the increases are found to be implemented every night to a specific level, the stimulation system can be configured to adjust the amplitude baseline in expectation of the continued need for the increased amplitude in following sleep periods. In another exemplary embodiment, if the stimulation system is configured to determine and does determine that the bio-impedance respiration sensor is detecting that some levels of stimulation are potentially causing arousals from sleep or an increase in arousals from sleep, the stimulation can be adjusted to decrease amplitude or a signal can be provided to the user or caretaker recommending further evaluation or the reduction of stimulation levels.

It is known that sleep position can influence the likelihood of a person having a disordered breathing event. For example, the airways of some individuals with OSA are more collapsible when sleeping in the supine position. As a result, greater levels of stimulation may be needed to minimize obstructive breathing when the patient is sleeping in an OSA-aggravating position, such as the supine position. Sleep position can be detected with a bio-impedance respiration sensor, an implanted accelerometer, or an external sensor communicating with the implanted stimulation device. When an OSA-aggravating sleep position is detected, the stimulation therapy can be modified using the above-described methods to increase the stimulation up to a level at which arousal from sleep is expected or detected, or to a pre-set maximum level. In another exemplary embodiment, the above-described cycling of stimulation therapies can be performed when an OSA-aggravating sleep position is detected to identify a stimulation therapy that is more effective for certain sleep positions. In a similar manner, the position and movement of the stimulated tongue, stimulated with a hypoglossal nerve stimulator, can be evaluated for efficacy in regard to sleep position to identify an appropriate stimulation therapy and to identify an effective field steering technique suitable for the sleep position.

It has been observed that the time spent sleeping in the N3 and REM sleep stages is often insufficient for patients suffering OSA. The detection of the amount of time spent in these and other stages of sleep can be used to adjust therapy to promote longer periods of sleep in under-utilized sleep states. The implanted bio-impedance sensor or other sensors, for example, can be used to detect sleep state using the methods described above, and the stimulation therapy can be adjusted or cycled through several stimulation therapies to promote certain stages of sleep, the entry into desired sleep stages, and the extension of time in desired sleep stages. For example, by cycling through different or selected stimulation therapies when the patient is in an under-utilized sleep state, as described above, stimulation parameters can be identified that disrupt, promote, and have no effect on the evaluated sleep state. When it is determined that one or more stimulation parameters, or a change to one or more stimulation parameters, typically results in longer periods of REM sleep, for example, as compared to other stimulation parameters, those parameters can be correlated and used to affect the desired sleep state in future sleep periods. Also, stimulation waveforms can be selected and implemented that utilize the parameters identified as having a positive influence on the entry into or the maintenance of a desired sleep state. Likewise, stimulation waveforms can be selected and implemented that avoid or minimize parameters identified as having a negative influence on the maintenance of a desired sleep state or that cause the premature exit from a desired sleep state. As can be appreciated, the correlation between stimulation waveforms and sleep state can be a factor among other factors in the optimization of a patient's stimulation therapy, or in the selection of default settings for the stimulation therapy.

Patient Control of Stimulation

Clinical studies have suggested that patient control of stimulation parameters can promote positive outcomes for patients being treated for OSA with a neurostimulator device. Patient control can facilitate proper stimulation therapy levels during therapy titration and in regular use, and can facilitate the implementation of therapy adjustment in response to patient circumstances night to night. Patient control can include control of stimulation parameters, stimulation intensity, the ability to stop and start therapy, the ability to pause or delay therapy, adjustment of automatic start or stop times of the stimulation therapy, the lag time between the delivery of a therapy command and the start of therapy (to account for the time it takes the patient to fall asleep), duration of the stimulation therapy, and the ability to change stimulation waveforms or to cycle through different stimulation waveforms. Patient control of stimulation therapy can be through an interface device such as patient controller 40 illustrated in FIG. 1, and can include a display and a feedback device that is visual, auditory, or haptic, or a combination of these. Patient control can also be provided in a context established by the care provider, with the patient's options for adjustment of the stimulation therapy limited by constraints defined by the care provider or limited to pre-determined modes established by the care provider. The patient's control can also be subject to mode changes that reset the device to a predetermined safe mode or stimulation therapy starting point, or reduce stimulation in predetermined increments, when there is an indication that the stimulation therapy has been poorly adjusted by the patient. These indications of a poor adjustment of the stimulation therapy can include excessive patient control adjustments, excessive manual pause, and frequent patient arousals.

Figure 16:
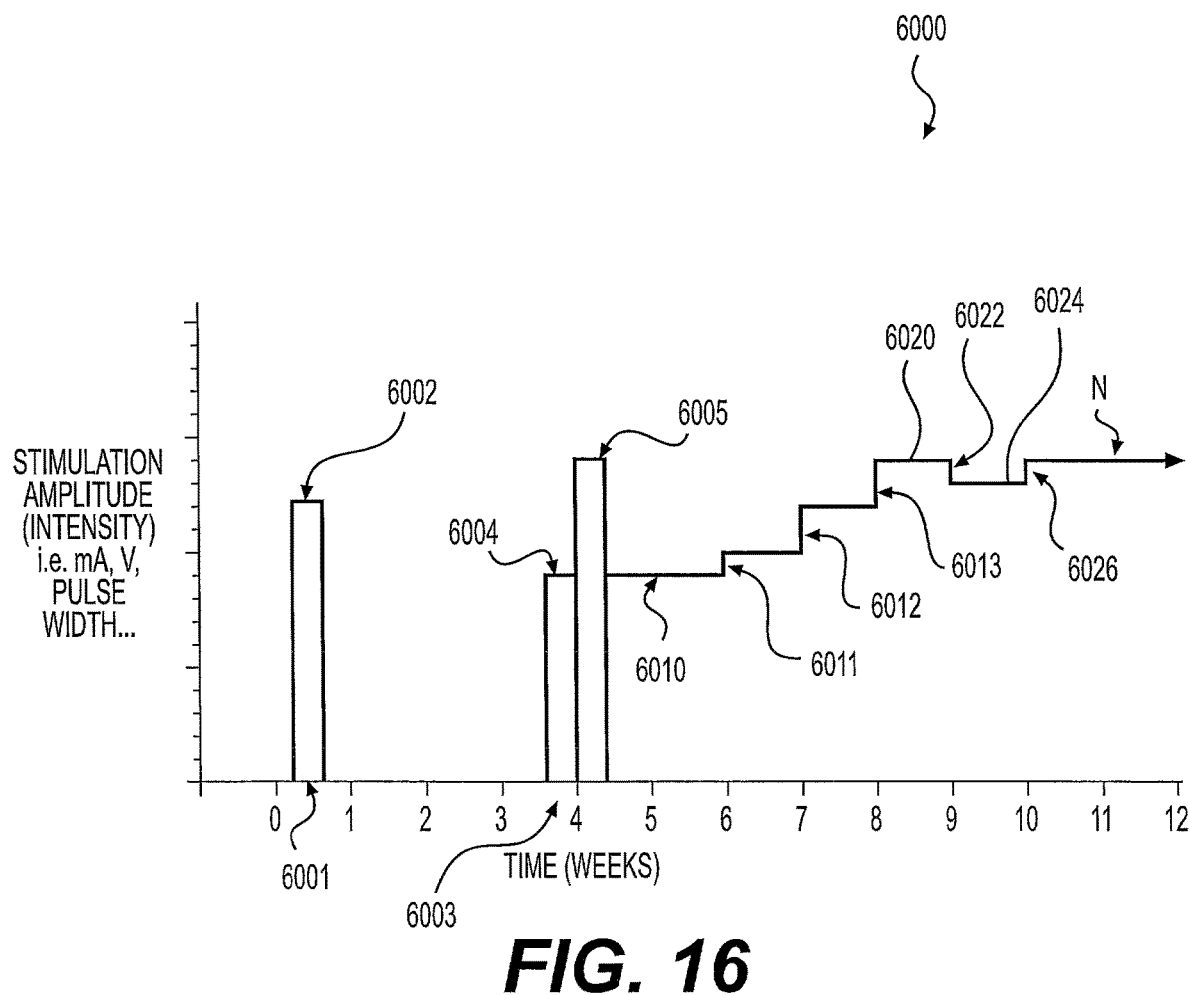
FIG. 16 illustrate an exemplary implementation of a stimulation therapy.

Referring to FIG. 16, it has been observed that the stimulation amplitude levels required to prevent disordered breathing during an initial PSG study (which may be used to define initial stimulation therapy target levels) may be at a stimulation level that is uncomfortable for the patient at the initial stage of therapy. It has also been observed that a patient receiving a stimulation therapy over time may later no longer be bothered by stimulation levels that were initially uncomfortable during the PSG or initial use of the neurostimulator, which may be the result of the stimulated muscles becoming stronger in response to the stimulation. Progressive increases in stimulation amplitudes and other related parameters as the patient acclimates to the sensation of therapy can assist with the initiation of stimulation therapy, and assist with the re-initiation of stimulation therapy after a significant pause or reduction in stimulation levels. By allowing the patient control of the stimulation therapy, the patient can determine when he or she is ready for a higher level of stimulation towards a target therapy level determined at the PSG. To simplify, and limit, the patient's control of the stimulation, the stimulation therapy and related parameters can be subject to programmed guidelines. Those programmed guidelines can be established by the care provider and can include, for example, a limit on the number of adjustments that the patient can make over a pre-determined time period, such as a limit on the number of incremental increases or decreases allowed each day so as to avoid severe changes in the stimulation therapy levels. In another example, the maximum stimulation levels available to the patient can be limited to guidelines or programmed by the caretaker to prevent drastic changes to stimulation therapy parameters over predefined time periods.

Again referring to FIG. 16, a therapy plan 6000 is shown in which the patient can incrementally increase stimulation levels or be subject to a predefined incremental increase in stimulation levels (of, e.g., stimulation amplitude, intensity, or pulse width) over a period of time (weeks) until reaching a normal therapy level (N). As illustrated in FIG. 16, an exemplary patient may receive the implanted neurostimulator in the first week of therapy 6001 and the use of the neurostimulator during surgery can provide a baseline stimulation level 6002 that achieves the opening of the airway. At weeks 3-5 (6003), the patient may undergo an evaluation or a PSG (at an awake comfort level determined in an office visit (6004) or at a night PSG amplitude needed for mitigation of OSA events (6005)) that determines that the patient's stimulation therapy comfort level is significantly less than a target level 6005 determined by a PSG. Further evaluation of the patient can determine that a target level 6005 is required to mitigate the occurrence of disordered breathing events and OSA. The patient may then be started on a stimulation therapy (at an initial level 6010) that is tolerable but insufficient to fully mitigate disordered breathing events. Over several weeks (weeks 4-9), the stimulation level can be incrementally increased manually (at 6011, 6012, and 6013) in response to patient commands as the patient learns to tolerate each stimulation level, or in accordance with an automated increase (6011, 6012, and 6013) that can be defined by the patient or physician. As illustrated at week 9 of FIG. 16, the patient may reach a point where the stimulation becomes intolerable when the neurostimulator is operating at the therapeutic stimulation level. For example, the patient's muscles may strengthen as therapy continues until reaching a stimulation level or point 6020 where the strengthened muscle contractions cause discomfort. In another example, the patient may be exposed to stress, diet, or drug related factors that reduce the patient's ability to tolerate the stimulation therapy. As illustrated in FIG. 16, the patient control allows the patient to incrementally decrease the stimulation level (at 6022) to regain a tolerable level 6024 of therapy, or to allow an automatic decrease in the stimulation level automatically in response to, for example, an excess number of arousals or therapy pauses during a sleep period. Likewise, when the patient believes that the therapeutic stimulation level 6024 is insufficient or becomes insufficient, patient control allows the stimulation level to be increased temporarily or permanently (at 6026). The level N after the increase 6026 may indicate normal therapy use by the patient, and may be substantially equal to the target level 6005. As described above, patient control can be limited by a context defined by the caretaker or in accordance with preprogrammed limitations built into the neurostimulator. Parameters subject to patient control can include stimulation amplitude (including current, voltage, pulse width, and frequency), duration of a pause in the stimulation therapy, rate of ramping after a pause, duration of a delay after a manual start of stimulation therapy, ramping rate after a manual start, the setting of core hours for the stimulation therapy amplitude, and the setting of a schedule for the core hours of stimulation therapy.

The way in which stimulation therapy sessions are started and stopped are significant factors affecting the efficacy of the therapy. The start of therapy can be based on a preset time after the patient indicates that sleep is planned, or according to a sleep schedule programmed into the neurostimulator. With patient control, the patient can adjust the timing so that additional time can be had when it is difficult to fall asleep, and schedules can be adjusted by patient control to account for a disrupted sleep schedule when travelling for example. Patient control can also provide control as to how a therapy starts or stops. The starting of the therapy can be automatic or manual depending on the patient's preference. Likewise, the cessation of therapy can be automatic when arousal is detected or when commanded by the patient. Patient control over therapy timing can also include control over the duration of a therapy delay and the rate of ramping at the end of a delay or pause. Patient control can also be provided over whether the neurostimulator will automatically suspend therapy if there is detection of an arousal from sleep (by the above-described respiratory waveform analysis or with the use of a motion detector, for example). Patient control can also be provided to control whether the stimulation amplitude can be increased during core hours and to what degree and duration the increase can be implemented. Patient control can also be provided to control as to whether an arousal from sleep will suspend or terminate a therapy, which can be useful when a patient forgets to shut off the therapy after awaking and the stimulation therapy resumes after the patient has left a home environment or to a location that does not provide access to the patient controller.

Stimulation Therapy Optimization

The stimulation system can be configured to automatically or semi-automatically adapt to optimize the stimulation therapy. In an exemplary embodiment, the amplitude can be adjusted to elicit a dose-metric airflow response. When obstructive breathing is detected, the stimulation amplitude may be increased automatically in an attempt to mitigate the OSA events. The nominal amplitude may be preferentially at a lower level to save battery life or prevent unwanted arousals from sleep. Increasing stimulation amplitude and the probability of an arousal is typically an acceptable risk trade-off to achieve resumption of unobstructed breathing. The following amplitude parameters can be adjusted: stimulation amplitude, stimulation intensity, current, voltage, pulse width, and frequency of pulse train. The signals used to indicate that stimulation amplitude may be increased or decreased to optimize therapy can include signals from a bio-impedance detector, which may identify disordered breathing and allow adjustments that cause the progressively incremental increase of stimulation levels until a pre-set maximum level is reached or until the disordered breathing is no longer detected. Another exemplary signal from a bio-impedance sensor can be used to identify the existence of arousals from sleep coincident with when stimulation is active without the detection of disordered breathing, which can be used to progressively decrease the stimulation amplitude until the arousals are no longer detected. In another exemplary embodiment, a signal from an implanted accelerometer may indicate the presence of disordered breathing or the presence of arousals, which can be used to increase or decrease the stimulation amplitude to mitigate arousals. A signal from a pause counter can count the number times the patient pauses or reduces a high level of stimulation which can be used to decrease the therapy levels if the behavior continues for a set number of nights. Conversely, the lack of pause detection, combined with detection of disordered breathing may be used to increase the stimulation amplitude. In another exemplary embodiment, an external home diagnostic sensing (PSG) signal can be telemetered to the implanted device to allow the determination as to whether the stimulation amplitude should be increased or decreased. This can be accomplished by having the PSG signals fed into a bed-side unit designed to do further processing of the signals and then telemetering the signal to the implanted system. Examples of signals from a PSG diagnostic system can include: airflow, motion detection, snore sensors, electroencephalogram (EEG), electrocardiogram (ECG), electrooculogram (EOG), Effort (Belts) and other typical PSG signals.

In an exemplary embodiment, the hypoglossal nerve stimulation system can maintain a log of the number of pauses in sequence and provide a determination that the patient is not able to fall asleep before the resumption of stimulation with the programmed pause duration or the programmed rate of ramping (as stimulation is resumed after a pause). The system (and the neurostimulator) can be configured to automatically increase the duration of the pauses or increase the length of the ramp to compensate. This may continue to be increased until a pre-set value(s) is reached or until the system no longer detects a series of pauses by the patient. Conversely, if the implanted bio-impedance sensor, an accelerometer, or an external PSG sensor detect the presence of sleep before the completion of a pause period, the pause period can then be automatically shortened or the therapy automatically resumed. This is desirable since increasing the amount of time stimulation is delivered during sleep will reduce the number of obstructive events and improve the patient's OSA therapy. Similarly, the system can provide an automatic adjustment of the duration of a pause to automatically increase the amount of time stimulation is delivered by progressively decreasing the duration of the delay.

In another exemplary embodiment, the start and stop times of certain core hours (programmed to provide a greater amplitude during predetermined times during a sleep period) can be adjusted to increase the amount of the sleep period covered by this higher amplitude setting when the start time is advanced with no arousals from sleep detected. Similarly, the stop time of the core hours can be extended progressively, provided no arousals from sleep are detected as a result. Conversely, if arousals are detected after the initiation of the core hours, the start time of core hours may be progressively delayed until arousals are not detected. Stop times of core hours may also be foreshortened if arousals are detected prior to the normal stop time for the elevated core hours amplitude.

As can be appreciated, and as described above, a normal stimulation delivery algorithm can include a stimulation period delivered with each breath, primarily covering inspiration (in an A-A-A-A pattern). The stimulation pattern can be manually adjusted by the patient (within pre-set limitations by the physician or by programming), by the physician, or automatically by the neurostimulator if it is determined that a desired level of effectiveness is not being achieved. Some exemplary stimulation patterns or algorithms can include an A-0-A-0 pattern, an A-B-A-B pattern, a A-B-0-A-B-0 pattern, and a variety of others. It is believed that the insertion of some non-stimulated breaths into sequences of stimulated breaths may help to trigger the patient's own physiological response to flow limitation. It is further believed that this may increase the inherent tone of the muscles responsible for patency that would add to the tone created by the functional stimulation from the implanted system. This may include the same muscles stimulated by the functional stimulation such as the genioglossus or other muscles such as the pharyngeal dilators.

Screening Methods

Figure 17B:
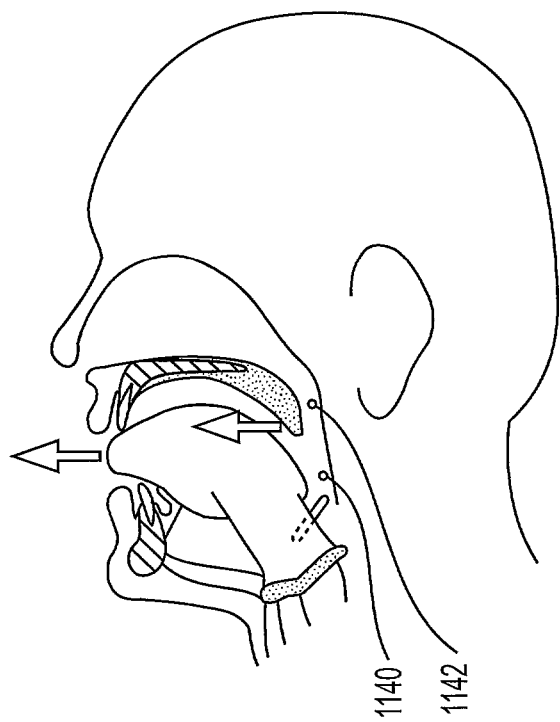
FIGS. 17A and 17B are schematic illustrations showing simplified structures of the upper airway in a lateral dissection with the palate and mandible shown in the medial sagittal section.
Figure 17A:
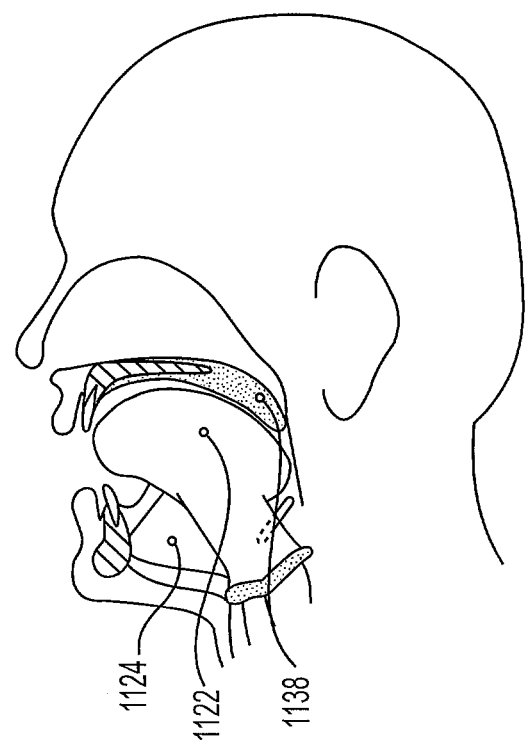
Figure 18B:
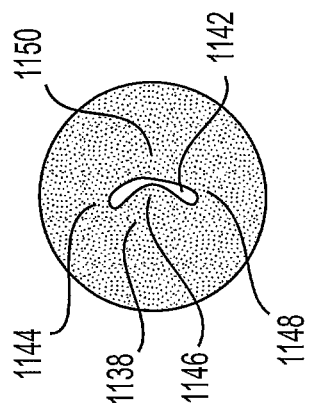
FIGS. 18B and 18C are views of the upper airway from the endoscope shown in FIG. 18A while the tongue is in a resting awake state (FIG. 18B) and during a tongue protrusion maneuver (FIG. 18C).
Figure 18C:
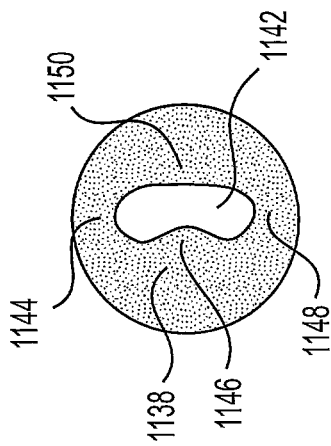
Figure 18A:
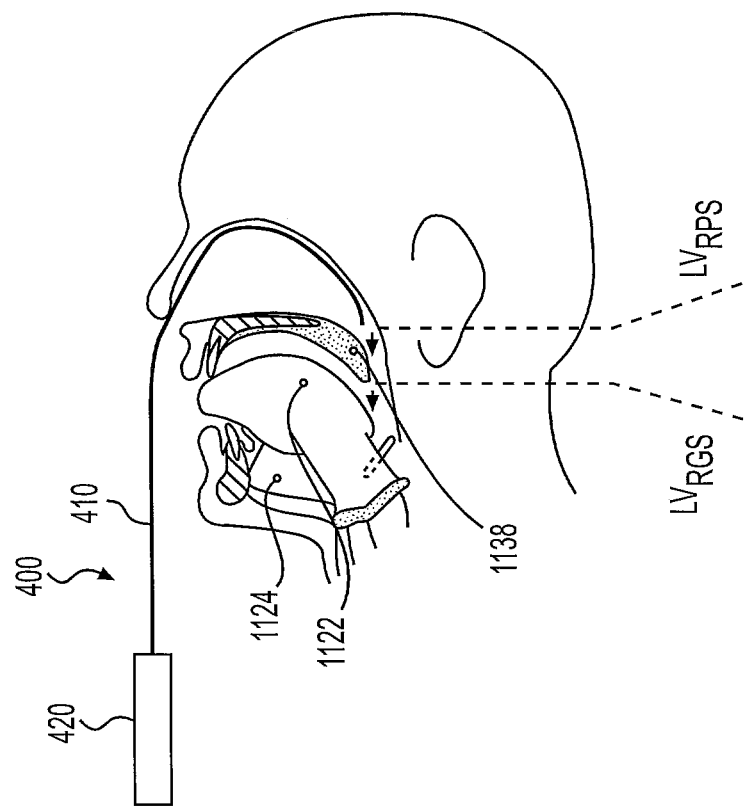
FIG. 18A is a schematic illustration showing an endoscope inserted into the airway.

Patients with obstructive sleep apnea have repeated episodes of complete (apnea) or partial (hypopnea) upper airway collapse during sleep. Aspects of patient anatomy are illustrated in FIGS. 17A, 17B, and 18A-18C. FIG. 17A shows the genioglossus 1124, tongue 1122, and soft palate 113. FIG. 17B shows the retro-glossal space 1140 and the retro-palatal space 1142. FIG. 18A also identifies a level $LV_{RGS}$ to visualize the retro-glossal space 1140, and a level $LV_{RPS}$ to visualize the retro-palatal space 1142. FIGS. 18B and 18C illustrate views from the level $LV_{RPS}$. The uvula bulge 1146 is also illustrated in FIGS. 18B and 18C.

The upper airway is generally defined by four walls: the posterior pharyngeal wall 1150, the right and left lateral pharyngeal walls 1144 and 1148, and anteriorly, the soft palate 1138 and the tongue 1122. The posterior pharyngeal wall 1150 is relatively fixed to the spinal column. Thus, collapse of the upper airway generally involves, depending on the level and mode of collapse, the tongue 1122, the soft palate 1138 and/or the lateral walls 1144 and 1148, or any combination thereof. In addition, or alternatively, collapse may involve the nasopharynx and/or hypopharynx (not shown).

The present disclosure offers a method to stimulate various upper airway structures and to observe and assess the effects thereof. The method generally involves causing the tongue 1122 to protrude while observing the response of the upper airway using an imaging technique. In general, the desired response is an increase in airway size. An adequate increase in airway size during the tongue protrusion maneuver is indicative of likely therapeutic success with HGNS. If an adequate increase in airway size is observed during the maneuver, a HGNS device may be implanted in the patient with a higher confidence of a successful outcome.

With reference to FIG. 18A, a naso-endoscope 400 or any other suitable imaging or visualization device, may be used to visually observe the upper airway while the patient is awake in the supine position. Alternatively, the observation may be made while the patient is in a seated or semi-recumbent position. A conventional naso-endoscope 400 including a fiber optic shaft 410 and a hand piece 420 may be used. Hand piece 420 may include a light source and a viewing window, and/or facilitate connection to ancillary imaging equipment (e.g., light source, camera, monitor, recorder, etc.). The patient may be asked to volitionally protrude his/her tongue 1122 straight and to its maximal extent with the mouth open and the lips loosely touching the tongue. Alternatively, the tongue protrusion may be performed sub-maximally, which may limit muscle contraction to the genioglossus 1124 without recruiting other musculature. Also alternatively, the tongue protrusion may be performed by asking the patient to point the tip of the tongue 1122 to one side or the other, which may more closely mimic unilateral hypoglossal nerve stimulation. The distal end of the endoscope 400 may be positioned superior to the soft palate 1138 and substantially parallel with the posterior pharyngeal wall 1150 to visualize the retro-palatal space 1142. The distal end of the endoscope 400 may be positioned inferior to the soft palate 1138, superior to the tongue base and substantially parallel with the posterior pharyngeal wall 1150 to visualize the retro-glossal space 1140. An example of the view of the retro-palatal upper airway space 1142 with the tongue 1122 in a relaxed (nominal) position is shown in FIG. 18B, and the same view with the tongue 1122 protruded is shown in FIG. 18C. As can be seen by comparing the views in FIGS. 18B and 18C, tongue protrusion can result in an increase in airway size, including area, circumference, anterior-posterior dimension, and lateral dimension. The increase in airway size at the level of the tongue 1122 and palate 1138 may be most discernable by an increase in anterior-posterior (AP) dimension between the posterior pharyngeal wall and the posterior side of the tongue base (retro-glossal) and soft palate 1138 (retro-palatal), respectively. Since the posterior pharyngeal wall 1150 is fixed relative to the spinal column, the increase in AP dimension involves anterior displacement of the tongue 1122 and soft palate 1138, respectively. The increase in airway size may also be discernable by an increase in lateral dimension between the right and left lateral pharyngeal walls 1144 and 1148.

During the tongue protrusion maneuver, observing an adequate increase in size of the retro-glossal airway 1140 is predictive of HGNS efficacy in patients with isolated tongue base collapse. However, as mentioned above, the soft palate 1138 contributes to upper airway collapse in the majority of OSA patients, thus also observing an increase in size of the retro-palatal airway 1142 during the tongue protrusion maneuver is predictive of HGNS efficacy in patients with isolated soft palate collapse and combined tongue 1122 plus soft palate 1138 collapse.

By way of example, not limitation, the following procedure may be followed to conduct the assessment and tongue protrusion maneuver. With the patient awake in the supine position, a nasal endoscope 400, or other suitable device, may be inserted into the pharynx via one of the nares to allow visualization of the upper airway. Video and still images may be captured at both the retro-palatal and retro-glossal levels $LV_{RPS}$ and $LV_{RGS}$ to document the effect of different maneuvers on anatomic structures of the upper airway (tongue 1122, palate 1138, epiglottis, pharyngeal walls 1144, 1148, and 1150, etc.). When imaging the retro-palatal level $LV_{RPS}$, the endoscope 400 may be placed such that all four walls (soft palate 1138, posterior wall 1150, and the two lateral walls 1144 and 1148) of the pharynx are visible before, during and after maneuvers. Similarly, when imaging the retro-glossal level $LV_{RGS}$, the endoscope 400 may be placed such that all four walls (tongue base, posterior wall 1150, and the two lateral walls 1144 and 1148) of the pharynx are visible before, during and after maneuvers. The endoscope 400 may be placed such that it runs generally parallel to the posterior wall 1150 and provides a symmetric field of view. This may be achieved by initially placing the distal end of the endoscope 400 near the level of the epiglottis and subsequently pulling back to the desired level. The patient then performs a series of maneuvers, including a tongue protrusion maneuver while breathing through their nose. The tongue protrusion maneuvers involves voluntary maximal straight tongue protrusion with lips loosely touching the tongue 1122, with the mouth completely open, and/or with the teeth clenched closed. Other maneuvers such as a Mueller maneuver (inspiratory efforts against a closed airway) may be performed as well. Each maneuver is held for ≥2 seconds, and performed several times while data (images and measurements) are gathered.

Alternative non-volitional tongue protrusion maneuvers include, for example, manually gripping and pulling the tongue 1122 anteriorly (e.g., by the physician), using a tongue retaining device (e.g., as used for the treatment of OSA), both of which are non-invasive. Another alternative is to stretch the palatoglossal arch by pushing the tongue 1122 down (depress tongue), by pushing the arch laterally outward, or by pulling the arch anteriorly (all palatoglossal maneuvers) using a tongue depressor or similar device. The palatoglossal maneuver may be used in place of or in combination with the tongue protrusion maneuver, and the entire description herein with respect to the tongue protrusion maneuver is applicable to the palatoglossal maneuver. Other alternative non-volitional tongue protrusion maneuvers include, for example, sub-mental stimulation and intramuscular stimulation (using fine wire electrodes, for example), both of which are relatively more invasive, but have the benefit of more selectively activating the genioglossus muscle alone to more closely mimic HGNS, as compared to volitional tongue protrusion which may recruit more than the genioglossus muscle 1124.

Figure 18D:
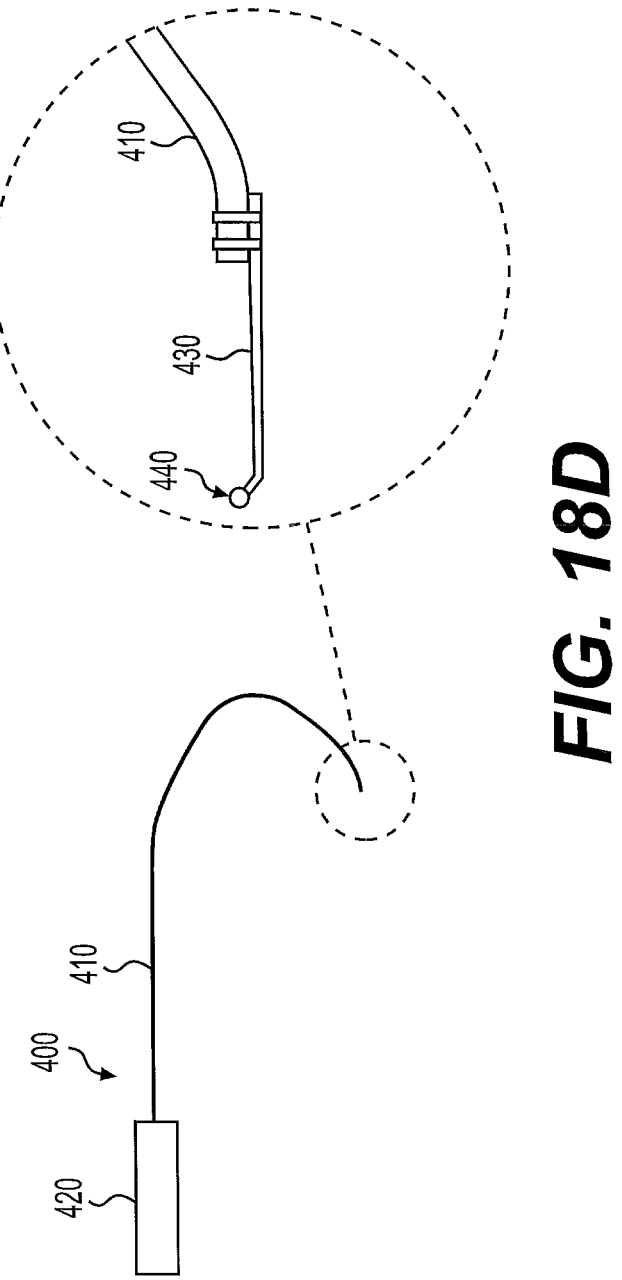
FIG. 18D is a schematic illustration of a modified endoscope.

Although naso-endoscopy is perhaps the most practical imaging technique to employ to assess the response of the upper airway to the tongue protrusion maneuver, other imaging techniques may be used as well. For example, x-ray imaging, fluoroscopy, x-ray computed tomography (CT), and optical coherence tomography (OCT) are suitable alternatives. These alternatives may provide more quantitative measurements by using a reference marker of known dimension in the field of view. Alternatively, improvements may be made to conventional naso-endoscopes to facilitate more quantitative measurements. For example, with reference to FIG. 18D, conventional naso-endoscope 400 includes a fiber optic shaft 410 and a hand piece 420. The distal end of the shaft 410 may be improved by including an attached extension 430 having a tip 440. The extension 430 positions the tip 440 into the field of view and may be approximated to the upper airway structure being visualized. The tip 440 may have a known dimension (e.g., diameter of 1 French or 3 mm), such that quantitative measurements of upper airway structures may be made by comparison. Other devices to make quantitative measurements may be employed, such as a laser pointer of know beam diameter projected onto the upper airway structure of interest. As an alternative, a catheter (e.g., nasogastric, nasoesophageal or nasopharyngeal catheter) may be inserted into the nasopharynx such that it resides in the field of view of the endoscope to serve as a quantitative reference of known dimension (e.g., diameter).

As mentioned above, the upper airway assessment during a tongue protrusion maneuver may be used as a screening tool wherein the patient is treated with the desired therapy (e.g., HGNS) only if the increase in size of the upper airway meets a predefined criterion. To this end, the response of the upper airway may be measured using a qualitative scale such as a visual analog scale of 0-10, wherein 0 represents a closed airway and 10 represents a completely open or patent airway. The airway size may be scored with the tongue at rest and during the tongue protrusion maneuver. The patient may be treated if the difference between the two scores meets a threshold, if the score during the maneuver meets a threshold, or if both the difference between the scores and the score during the maneuver meet thresholds (e.g., 5 on a scale of 0-10).

Alternatively, the response of the upper airway may be measured using a quantitative scale such as: a pixel count of captured images which may be representative of cross-sectional area; a linear dimension such as anterior-posterior and/or lateral; or a measure of circumference. Here again, the airway size may be measured (e.g., pixel count, AP length (i.e., the distance between the anterior and the posterior walls of the upper airway), and/or lateral width) with the tongue at rest and during the tongue protrusion maneuver. The patient may be treated if the difference between the two measures meets a threshold, if the measure during the maneuver meets a threshold, or if both the difference in measures and the measure during the maneuver meet thresholds.

In each case, the threshold may be a percentage increase in size (e.g., difference in AP length=50%), an absolute value (e.g., difference of AP length=0.5 cm), or a relative value. The relative value may be with reference to an anatomical landmark such as the width of the superior aspect of the epiglottis (e.g., difference in AP length=50% of epiglottal width).

Other response criteria observed during the tongue protrusion maneuver, in addition to an increase in airway size, may be used as well. For example, movement of the hyoid bone may be observed visually, by palpation or by x-ray. Movement of the hyoid bone in an anterior direction and/or inferior direction during the tongue protrusion maneuver may be predictive of therapeutic success with HGNS.

Optionally, it may be desirable to observe the response of the airway at the level of collapse. The level of collapse may be determined during sleep or simulated sleep (e.g. sedation) using known techniques such as drug induced sleep endoscopy (DISE), or may be determined by examination of the airway structures using known techniques such as naso-endoscopy. In some embodiments, the airway may be observed using imaging and visualization methods that do not require subjecting the patient to drug induced sleep. Stated differently, portions of the upper airway may be observed while the patient is awake or asleep, regardless of whether such sleep is drug induced or natural. In non-drug induced imaging methods, the upper airway may be visualized or otherwise monitored via e.g., magnetic imaging resonance. Further, flow sensors may be utilized to observe or otherwise monitor the patency of the upper airway. The airway may collapse at the level of the tongue base (i.e., retro-glossal), at the level of the palate (i.e. retro-palatal), or both levels. In some cases, airway collapse may occur in portions of the airway further away from the soft palate and towards the epiglottis. Such portions may include the oropharynx and/or hypopharynx. Because most OSA patients have palatal involvement in airway collapse, it may not be necessary to determine the level of collapse. In this case, collapse may be assumed to occur at least at the level of the palate, and therefore an adequate response (e.g., increase in airway size) in the retro-palatal space during the tongue protrusion maneuver would be indicative of likely therapeutic success with HGNS.

Typically, candidates for HGNS therapy are those who (1) do not experience palatal complete concentric collapse (CCC), in which the circular airway at the level of the soft palate uniformly moves radially inward toward the center of the airway; and (2) do experience anterior-posterior collapse (APC) of the upper airway, in which the anterior wall moves towards the posterior wall, such as due to posterior movement of the tongue while the patient sleeps. Wall collapse, however, may occur in configurations other than APC which may nevertheless render a patient a candidate for HGNS treatment. For example, HGNS may be used to treat patients, provided they do not experience palatal CCC, in whom at least one wall of the airway moves towards a central axis of the airway. Thus, candidates for HGNS therapy include those who experience lateral-lateral collapse (LLC), in which at least one first lateral wall moves towards at least one second lateral wall. LLC may occur independently, in which at least one lateral wall moves inwardly, or jointly, in which multiple lateral walls move inwardly, for example.

Candidates also include those who experience a predetermined ratio of APC and LLC. For example, HGNS patients include those who experience a 1:1 ratio of APC and LLC, in which, for example, the patient experiences 50% APC and 50% LLC. Further, HGNS patients may include those individuals that experience a 2:1 ratio of APC and LLC. For example, an anterior wall may move inwardly twice as much as a lateral wall. Patients that experience LLC where two lateral wall movements move inwardly by approximately the same amount as anterior wall (or the posterior wall) may also experience a 2:1 ratio, since the movement of both lateral walls may combine to collectively constrict or otherwise reduce the patency of the patient's airway.

As disclosed above, HGNS may be used to treat patients intolerant of CPAP, provided they do not experience palatal CCC. Complete concentric collapse at other levels, however, may also exclude patients from HGNS treatment. For example, as alluded to above, airway constriction may occur along the upper airway moving away from the soft palate towards the epiglottis. Patients who experience CCC at the hypopharynx and/or velopharynx levels may be excluded from HGNS treatment. Moreover, collapse at the palatal, hypopharynx, and/or velopharynx level below CCC may exclude patients from HGNS treatment.

The observation methods disclosed herein may be used to observe any of the types of wall movement disclosed herein. For example, these observation methods may be used to observe CCC, anterior-posterior movement, lateral-lateral movement, and any combination thereof, including ratios of APC to LLC. Moreover, these observation methods may be used to observe movement at various levels, including the palatal, hypopharynx, and/or velopharynx levels.

Screening criteria to select individuals who are more likely to respond to HGNS may include DISE-identified APC of the upper airway as well as movement of the lateral walls along with anterior-posterior movement, provided that the lateral movement does not exceed: (i) the anterior-posterior movement; (ii) 50% of the anterior-posterior movement; or (iii) other % of the anterior-posterior movement. As another example, screening criteria may include DISE-identified CCC combined with awake endoscopy demonstrating anterior-posterior movement with tongue protrusion.

Once an INS is implanted into a patient, parameters, such as, e.g., stimulation parameters, may be adjusted by the patient or via automatic settings programmed into the device to increase the effectiveness of the treatment and patient comfort. For example, the INS may include a library of settings which the patient may adjust or selectively choose, wherein each setting includes a set of parameters established by the patient's physician and programmed into the device. The set of parameters for each setting option in the library may include, for instance: voltage, current, pulse width, field steering options, frequency of stimulation, stimulation waveform type, timing of stimulation relative to respiration, pattern of stimulation, and/or any of the combination of parameters mentioned above with reference to cycling. Additional parameters may include adjusting initiating or triggering of stimulation. For example, a patient or provider may selectively choose to offset stimulation relative to, e.g., the beginning of inspiration. Stated differently, stimulation may be started a predetermined time period (e.g., 300 ms) prior to or after the initiation of inspiration or a prediction of inspiration. The list of library setting options may be selected automatically by the implanted device based on feedback of body position, disordered breathing, and other indications of effectiveness such as number of pauses, body movement, and arousals from sleep.

The pattern of stimulation may be chosen, for example, from A-A-A-A (e.g., a continuous pulse train) and A-O-A-O-A (e.g., an on, off, on, off, etc. stimulation pulse patent). In another embodiment, the pattern of stimulation may include, for example, A-A'-A-A'. In such an example, "A" may be a first pulse having a first amplitude and "A'" may be a second pulse having a second amplitude different than the first amplitude. In another embodiment, the pattern of stimulation may include, for example, A-B-A-B. In such an example, "A" may include a first waveform, such as, for example, a square waveform, and "B" may include a second waveform different from the second waveform, such as, e.g., a triangular waveform. In one embodiment, the INS device is provided with four selection options for the patient to adjust: amplitude, pulse width, frequency, and a fourth variable, wherein the fourth variable is chosen from one of the set of parameters listed above. In addition, the disclosed treatment system may be provided with an option to selectively activate or otherwise energize one or more desired electrode cuffs of a plurality of electrode cuffs, which may be implanted on differing upper airway nerves or on various portions/branches of a single upper airway nerve (e.g., the hypoglossal nerve). In such embodiments, the patient, via patient controller 40, may be able to selectively choose which electrode cuffs they wish to energize. In embodiments where multiple electrode cuffs are implanted at multiple stimulation sites, stimulation may be performed independently of any feedback, such as, e.g., respiration sensing.

From the foregoing, it will be apparent to those skilled in the art that the present disclosure provides, in exemplary non-limiting embodiments, devices and methods for nerve stimulation for OSA therapy. Further, those skilled in the art will recognize that the present disclosure may be manifested in a variety of forms other than the specific embodiments described and contemplated herein. Accordingly, departures in form and detail may be made without departing from the scope and spirit of the present disclosure as described in the appended claims.

I claim:

1. A method of providing a sleep apnea nerve stimulation therapy to a subject, the method comprising:
   detecting a respiratory waveform of the subject with a sensor configured for coupling to the subject, the respiratory waveform including a plurality of respiratory cycles each corresponding to at least one of a breath or an attempted breath of the subject;
   identifying a breathing pattern within the respiratory waveform over a period of time, the breathing pattern comprising a repeating pattern of a plurality of respiratory cycles followed by at least one respiratory cycle corresponding to a disordered breathing event;
   comparing an inspiratory duration of an inspiratory period of the at least one respiratory cycle to a total duration of the at least one respiratory cycle;
   determining, based on the comparison between the inspiratory duration and the total duration, that the inspiratory duration exceeds a threshold percentage of the total duration to support an identification of the disordered breathing event; and
   upon determining that the inspiratory duration exceeds the threshold percentage of the total duration, generating a series of stimulation pulses based on the breathing pattern with an implantable nerve stimulator configured for coupling to a hypoglossal nerve of the subject, the series of stimulation pulses coordinated with the breathing pattern.

2. The method of claim 1 wherein the generating of the series of stimulation pulses coordinated with the breathing pattern includes the generating of a first stimulation pulse during the plurality of respiratory cycles and the generating of a second stimulation pulse during the at least one respiratory cycle corresponding to the disordered breathing event.

3. The method of claim 2 wherein the first stimulation pulse is at a first amplitude and the second stimulation pulse is at a second amplitude that is greater than the first amplitude.

4. The method of claim 1 further comprising:
   receiving a command to initiate the nerve stimulation therapy and commencing an initial period when no stimulation is provided so as to allow the subject to fall asleep.

5. The method of claim 1 wherein the breathing pattern is determined from a detection of at least one of a signal peak, a signal minimum, an expiration detection, or an inspiration detection.

6. The method of claim 1 wherein the breathing pattern includes a trend defined by at least one of the plurality of respiratory cycles, a plurality of peak magnitudes of the plurality of respiratory cycles, a plurality of minima magnitudes of the plurality of respiratory cycles, a plurality of expiration detections of the plurality of respiratory cycles, or a plurality of inspiration detections of the plurality of respiratory cycles.

7. The method of claim 1, wherein comparing the portions of the breathing pattern within the respiratory waveform to support the identification of the disordered breathing event comprises comparing a first inspiratory period to a subsequent second inspiratory period to determine that the second inspiratory period indicates the disordered breathing event.

8. The method of claim 7, wherein the determination that the second inspiratory period indicates the disordered breathing event is based on the second inspiratory period being longer than the first inspiratory period.

* * * * *